US011634773B2

(12) United States Patent
Swanton et al.

(10) Patent No.: US 11,634,773 B2
(45) Date of Patent: Apr. 25, 2023

(54) ANALYSIS OF HLA ALLELES IN TUMOURS AND THE USES THEREOF

(71) Applicants: THE FRANCIS CRICK INSTITUTE LIMITED, London (GB); UNIVERSITY COLLEGE LONDON, London (GB); CANCER RESEARCH TECHNOLOGY LIMITED, London (GB)

(72) Inventors: Charles Swanton, London (GB); Nicholas McGranahan, London (GB); Rachel Rosenthal, London (GB)

(73) Assignees: THE FRANCIS CRICK INSTITUTE LIMITED, London (GB); UNIVERSITY COLLEGE LONDON, London (GB); CANCER RESEARCH TECHNOLOGY LIMITED, London (GB)

( * ) Notice: Subject to any disclaimer, the term of this patent is extended or adjusted under 35 U.S.C. 154(b) by 452 days.

(21) Appl. No.: 16/628,067

(22) PCT Filed: Jul. 13, 2018

(86) PCT No.: PCT/GB2018/052004
§ 371 (c)(1),
(2) Date: Jan. 2, 2020

(87) PCT Pub. No.: WO2019/012296
PCT Pub. Date: Jan. 17, 2019

(65) Prior Publication Data
US 2021/0147934 A1    May 20, 2021

(30) Foreign Application Priority Data

Jul. 14, 2017 (GB) .................................. 1711349
Oct. 2, 2017 (GB) .................................. 1716079

(51) Int. Cl.
| | | |
|---|---|---|
| C12Q 1/6881 | (2018.01) | |
| C12Q 1/6869 | (2018.01) | |
| A61K 39/00 | (2006.01) | |
| C12Q 1/6886 | (2018.01) | |
| C07K 14/74 | (2006.01) | |
| C07K 16/28 | (2006.01) | |

(52) U.S. Cl.
CPC ........ *C12Q 1/6881* (2013.01); *A61K 39/0011* (2013.01); *C07K 14/70539* (2013.01); *C07K 16/2833* (2013.01); *C12Q 1/6869* (2013.01); *C12Q 1/6886* (2013.01); A61K 2039/5158 (2013.01); C12Q 2535/101 (2013.01); C12Q 2537/165 (2013.01)

(58) Field of Classification Search
CPC ........ A61K 39/0011; A61K 2039/5158; C07K 14/0539; C07K 16/2833; C12Q 2537/165

USPC ........................................................ 435/6.14
See application file for complete search history.

(56) References Cited

U.S. PATENT DOCUMENTS

| 11,098,121 B2 | 8/2021 | McGranahan et al. |
|---|---|---|
| 2014/0120622 A1 | 5/2014 | Gregory et al. |
| 2015/0110754 A1 | 4/2015 | Bai et al. |
| 2016/0131657 A1 | 5/2016 | Xing et al. |
| 2018/0064793 A1 | 3/2018 | McGranahan et al. |
| 2020/0000903 A1 | 1/2020 | McGranahan et al. |
| 2020/0000904 A1 | 1/2020 | McGranahan et al. |
| 2021/0147942 A1 | 5/2021 | Swanton et al. |

FOREIGN PATENT DOCUMENTS

| WO | WO-94/29348 A2 | 12/1994 | |
|---|---|---|---|
| WO | WO-2015/085147 A1 | 6/2015 | |
| WO | WO-2017/042394 A1 | 3/2017 | |
| WO | WO-2017/106638 A1 | 6/2017 | |
| WO | WO-2017/205678 A1 | 11/2017 | |
| WO | WO-2018/005276 A1 | 1/2018 | |
| WO | WO-2018195357 A1 * | 10/2018 | ............. A61K 35/17 |

OTHER PUBLICATIONS

Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Byers, T. (CA Cancer Journal, 1999, 49: 353-361).*
Abbosh C et al., Phylogenetic ctDNA analysis depicts early-stage lung cancer evolution, Nature. Apr. 26, 2017;545(7655):446-451.
Alexandrov et al. (2013). Signatures of mutational processes in human cancer. Nature 500, 415-421.
Anagnostou, Evolution of Neoantigen Landscape during Immune Checkpoint Blockade in Non-small cell lung cancer, Cancer Discovery, Mar. 2017, vol. 7, pp. 264-276.
Andreatta et al., (2016). Gapped sequence alignment using artificial neural networks: application to the MHC class I system. Bioinformatics 32, 511-517.
Ares et al., Methods for processing high-throughput RNA sequencing data, Cold Spring Harbor Protocol, Nov. 3, 2014, vol. (11) pp. 1139-1148.
Boa et al., Review of Current Methods, Applications, and Data Management for the Bioinformatics Analysis of Whole Exome Sequencing, Cancer Informatics. 2014;13(Suppl 2):67-82.

(Continued)

*Primary Examiner* — Yan Xiao
(74) *Attorney, Agent, or Firm* — Marshall, Gerstein & Borun LLP

(57) ABSTRACT

The present invention relates to a method for determining whether an HLA allele is lost in a tumour in a subject, wherein said method comprises the step of determining the specific copy number of said HLA allele in said tumour. The invention also relates to a method for treating cancer in a subject, comprising targeting a neoantigen which is predicted to be presented by an HLA molecule encoded by an HLA allele which has been determined not to have been lost in a tumour in said subject.

12 Claims, 25 Drawing Sheets

(56) References Cited

OTHER PUBLICATIONS

Bodanszky, Peptide Chemistry, A Practical Textbook, 2nd edition, Springer-Verlag, Berlin (1993).
Brastianos et al., Genomic characterization of brain metastases reveals branched evolution and potential therapeutic targets, Cancer Discov. Nov. 2015; 5(11): 1164-1177.
Brown et al., (2014). Neo-antigens predicted by tumour genome meta-analysis correlate with increased patient survival. Genome research 24, 743-750.
Butterfield, Cancer vaccines, BMJ. 2015 22;350:h988.
Cabrera, Analysis of HLA class I alterations in tumors: choosing a strategy based on known patterns of underlying molecular mechanisms, Tissue Antigens, 2007, vol. 69, suppl 1, pp. 264-268.
Campbell et al. (2016). Distinct patterns of somatic genome alterations in lung adenocarcinomas and squamous cell carcinomas. Nature genetics 48, 607-616.
Campoli et al., (2008). HLA antigen changes in malignant cells: epigenetic mechanisms and biologic significance. Oncogene 27, 5869-5885.
Carter et al. (2012). Absolute quantification of somatic DNA alterations in human cancer. Nature biotechnology 30, 413-421.
Carter et al., Molecular analysis of circulating tumor cells identifies distinct copy-number profiles in patients with chemosensitive and chemo refractory small-cell lung cancer, Nat Med. Jan. 2017;23(1):114-119. Epub Nov. 21, 2016.
Clackson et al., Making antibody fragments using phage display libraries, Nature. 352:624-628 (1991).
Creighton (1983) Proteins Structures and Molecular Principles, WH Freeman and Co, New York NY.
Davoli et al., (Jan. 2017). Tumour aneuploidy correlates with markers of immune evasion and with reduced response to immunotherapy. Science, vol. 355, eaaf8399.
Del Campo et al. (2014). Immune escape of cancer cells with beta2-microglobulin loss over the course of metastatic melanoma. Int J Cancer 134, 102-113.
Donia et al., Characterization and comparison of 'standard' and 'young' tumour-infiltrating lymphocytes for adaptive cell therapy at a Danish translational research institution, Scand. J. Immunol., 75(2):157-167 (2012).
Donia et al., Simplified protocol for clinical-grade tumor-infiltrating lymphocyte manufacturing with use of the Wave bioreactor, Cytotherapy, 16(8):1117-20 (2014).
Dudley et al., CD8+ enriched "young" tumor infiltrating lymphocytes can mediate regression of metastic melanoma, Clin Cancer Res, 16(24): 6122-6131 (2010).
Dudley et al., Generation of tumor-infiltrating lymphocyte cultures for use in adoptive transfer therapy for melanoma patients, J. Immunother. 2003; 26(4): 332-342.
European Genome-phenome Archive of human data consented for biomedical research; https://ega-archive.org (2020).
Favero et al., Sequenza: Allele-Specific Copy Number and Mutation Profiles From Tumor Sequencing Data, Ann Oncol, 2015, 26(1):64-70.
Forget et al., Activation and propagation of tumor-infiltrating lymphocytes on clinical-grade designer artificial antigen-presenting cells for adoptive immunotherapy of melanoma, J Immunother. Nov.-Dec. 2014;37(9):448-60.
Ha et al. (2014) TITAN: Inference of Copy Number Architectures in Clonal Cell Populations From Tumor Whole-Genome Sequence Data, Genome Res Nov. 2014;24(11):1881-1893.
Hanahan et al., (2011). Hallmarks of cancer: the next generation. Cell 144, pp. 646-674.
Herbst et al, Predictive Correlates of Response to the anti-PD-L1 Antibody MPDL3280A in Cancer Patients, 2014, Nature 515 (7528) pp. 563-567.
Hicklin et al., (1999). HLA class I antigen downregulation in human cancers: T-cell immunotherapy revives an old story. Mol Med Today 5, 178-186.
Hiraki, High frequency of allele-specific down-regulation of HLA class I expression in lung cancer cell lines, Anticancer Research, 2004, vol. 24, pp. 1525-1528.
Hoof et al., (2009). NetMHCpan, a method for MHC class I binding prediction beyond humans. Immunogenetics 61, 1-13.
Huang, HLAreporter: a tool for HLA typing from next generation sequencing data, Genome Medicine, 2015, vol. 7, article No. 25.
Hundal et al (2016) Cancer Immunogenomics: Computational Neoantigen Identification and Vaccine Design, Cold Spring Harb Symp Quant Biol., 81:105-111.
Hundal et al, pVAC-Seq: A genome-guided in silico approach to identifying tumor neoantigens, Genome Medicine, 2016, vol. 8, article 11.
International Application No. PCT/GB2018/052004, International Search Report and Written Opinion, dated Nov. 28, 2018.
Jamal-Hanjani et al. Tracking the Evolution of Non-Small-Cell Lung Cancer. N Engl J Med. Jun. 1, 2017 col. 376 No. 22 pp. 2109-2121.
Ka, HLAscan:genotyping of the HLA region using next-generation sequencing data, BMC Bioinformatics, May 2017, vol. 18, article No. 258.
Kammermeier et al., Targeted gene panel sequencing in children with very early onset inflammatory bowel disease-evaluation and prospective analysis, J. Med. Genet., 2014, 51 (11):748-755.
Koboldt et al. VarScan 2: somatic mutation and copy number alteration discovery in cancer by exome sequencing. Genome research. 2012;22(3):568-76.
Kohler et al., Continuous cultures of fused cells secreting antibody of predefined specificy, Nature, 256:495 (1975).
Koopman, Multiple genetic alterations cause frequence and hetergeneous huan histocompatibility leukocyte antigen class I loss in cervical cancer, Journal of Experimental Medicine, 2000, vol. 191, pp. 961-975.
Landau D A et al., Evolution and Impact of subclonal mutations in chronic lymphocytic leukemia, Cell., Feb. 14, 2013, 152(4), pp. 714-726.
Langmead et al., (2012). Fast gapped-read alignment with Bowtie 2. Nat Methods 9, 357-359.
Lawrence et al., (2014). Discovery and saturation analysis of cancer genes across 21 tumour types. Nature 505, 495-501.
Li, A statistical framework for SNP calling, mutation discovery, association mapping and population genetical parameter estimation from sequencing data, Bioinformatics, 2011, 27, 2987-2993.
Li et al. (2016). Comprehensive analyses of tumour immunity: implications for cancer immunotherapy. Genome biology 17, 174.
Li et al. The Sequence Alignment/Map format and SAMtools. Bioinformatics. 2009;25(16):2078-9.
Li H, Durbin R. Fast and accurate short read alignment with Burrows-Wheeler transform. Bioinformatics. 2009;25(14):1754-60.
Lundegaard et al., Accurate approximation method for prediction of class I MHC affinities for peptides of length 8, 10 and 11 using prediction tools trained on 9mers, Bioinformatics. Jun. 1, 2008;24(11):1397-8.
Lundegaard et al., NetMHC-3.0: accurate web accessible predictions of human, mouse and monkey MHC class I affinities for peptides of length 8-11, Nucleic Acids Res. 2008:W509-12.2008.
Mardis E R, Next Generation Sequencing Platforms, Annu Rev Anal Chem, 2013, vol. 6, pp. 287-303.
Marks et al., By-passing immunization. Human antibodies from V-gene libraries displayed on phage, J. Mol. Biol., 1991, vol. 222 pp. 581-597.
Martin et al., (2013). Immunogenetics of HIV disease. Immunological reviews 254, 245-264.
McGranahan et al., Allele-specific HLA Loss and Immune Escape in Lung Cancer Evolution, Cell, Nov. 30, 2017, 171: 1259-1271.
McGranahan N et al., Clonal neoantigens elicit T cell immunoreactivity, Science, 2016, vol. 351, pp. 1463-1469.
Mehta et al., (2008). Association of antigen processing machinery and HLA class I defects with clinicopathological outcome in cervical carcinoma. Cancer Immunol Immunother, 57, 197-206.
Meyerson et al., Advances in understanding cancer genomes through second-generation sequencing, Nat. Rev. Genet., 11(10):685-96 (2010).

(56) References Cited

OTHER PUBLICATIONS

Moretta et al., (2014). Human natural killer cells: origin, receptors, function, and clinical applications. Int Arch Allergy Immunol 164, 253-264.
Nielsen et al., (2003). Reliable prediction of T-cell epitopes using neural networks with novel sequence representations, Protein Sci May 2003;12(5):1007-17.
Nielsen et al., NetMHCpan-3.0; improved prediction of binding to MHC class I molecules integrating information from multiple receptor and peptide length datasets, Genome Medicine, (2016) 8:33.
Nielsen,M. and Lund,O. (2009) NN-align. An artificial neural network-based alignment algorithm for MHC class II peptide binding prediction. BMC Bioinformatics, 10, 296.
Obenaus et al., Identification of human T-cell receptors with optimal affinity to cancer antigens using antigen-negative humanized mice, Nat Biotechnol., 2015, 33(4):402-7.
Ott et al., An Immunogenic Personal Neoantigen Vaccine for Patients With Melanoma, Nature, 547(7662):217-21 (Jul. 13, 2017).
Palucka et al., Dendritic-cell-based therapeutic cancer vaccines. Immunity. (2013) 39:38-48.
Perkel, Biocompare, May 8, 2014 ; Build Your Own Gene Panels with These Custom NGS Targeting Tools, downloaded from the Internet at: <https://www.biocompare.com/Editorial-Articles/161194-Build-Your-Own-Gene-Panels-with-These-Custom-NGS-Targeting-Tools/>.
Piha-Paul et al. T-cell inflamed phenotype gene expression signatures to predict clinical benefit from pembrolizumab across multiple tumor types. J Clin Oncol. 2016; 34(suppl; abstr 1536).
Ribas et al . . . Association of response to programmed death receptor 1 (PD-1) blockade with pembrolizumab (MK-3475) with an interferon-inflammatory immune gene signature. J. Clin. Oncol. 2015;33:3001. [Abstract Only].
Rimmer et al . . . (2014). Integrating mapping-, assembly- and haplotype-based approaches for calling variants in clinical sequencing applications. Nature genetics 46, 912-918.
Rizvi NA, Hellmann MD, Snyder A, Kvistborg P, Makarov V, Havel JJ, et al. Cancer immunology. Mutational landscape determines sensitivity to PD-1 blockade in non-small cell lung cancer. Science. 2015;348(6230):124-8.
Roberge et al., A strategy for a convergent synthesis of N-linked glycopeptides on a solid support, (1995) Science 269:202-204.
Rooney et al., Infusion of cytotoxic T cells for the prevention and treatment of Epstein-Barr virus-induced lymphoma in allogeneic transplant recipients, Blood. Sep. 1, 1998 ;92(5):1549-55.
Rooney et al., (2015). Molecular and genetic properties of tumours associated with local immune cytolytic activity. Cell 160, 48-61.
Rosenberg et al., Durable complete responses in heavily pretreated patients with metastatic melanoma using T-cell transfer immunotherapy, 2011, Clin Cancer Res:17(13):4550-7.
Rosenthal et al., (2016). deconstructSigs: delineating mutational processes in single tumours distinguishes DNA repair deficiencies and patterns of carcinoma evolution. Genome biology vol. 17, 31.
Sahin et al. (Jul. 13, 2017). Personalized RNA mutanome vaccines mobilize poly-specific therapeutic immunity against cancer. Nature. 547, pp. 222-226.

Schrörs et al., HLA class I loss in metachronous metastases prevents continuous T cell recognition of mutated neoantigens in a human melanoma model, ONCOTARGET, (Apr. 25, 2017), vol. 8, No. 17, doi:10.18632/oncotarget.16048, pp. 28312-28327.
Schumacher et al., (2015). Neoantigens in cancer immunotherapy. Science New York, NY 348, 69-74.
Shen et al. (2016). FACETS: allele-specific copy number and clonal heterogeneity analysis tool for high-throughput DNA sequencing. Nucleic Acids Res 44, e131.
Shen et al., An effective and effecient peptide binding prediction approach for a broad set of HLA-D DR molecules based on ordered weighted averaging of binding packet profiles, Proteome Sci. Nov. 7, 2013;11 (Suppl 1):S15.
Shiina et al., The HLA genomic loci map: expression,interaction, diversity and disease, Journal of Human Genetics (2009) 54, 15-39.
Shukla et al. (2015). Comprehensive analysis of cancer-associated somatic mutations in class I HLA genes. Nature biotechnology 33, 1152-1158.
Snyder et al. Genetic basis for clinical response to CTLA-4 blockade in melanoma. N Engl J Med. 2014;371(23):2189-99.
Spranger et al., (2013). Up-regulation of PD-L1 , I DO, and T(regs) in the melanoma tumour microenvironment is driven by CD8(+) T cells. Sci Transl Med 5, 200ra116.
Szolek et al., (2014). OptiType: precision HLA typing from next-generation sequencing data. Bioinformatics 30, 3310-3316.
The Cancer Genome Atlas Program, National Institutes of Health, National Cancer Institute, downloaded from the Internet at: <https://www.cancer.gov/about-nci/organization/ccg/research/structural-genomics/tcga) (2006).
Tran et al. (2016). T-Cell Transfer Therapy Targeting Mutant KRAS in Cancer. The New England Journal of Medicine, vol. 375, pp. 2255-2262.
Tumeh et al, PD-1 blockade induces responses by inhibiting adaptive immune resistance, Nature, Nov. 27, 2014;515(7528):568-712.
Van Allen et al. Genomic correlates of response to CTLA-4 blockade in metastatic melanoma. Science. 2015;350(6257):207-11.
Van Loo et al. (2010). Allele-specific copy number analysis of tumours. Proceedings of the National Academy of Sciences of the United States of America 107, 16910-16915.
Warren et al., (2012) Derivation of HLA types from shotgun sequence datasets, Genome Medicine vol. 4(12), 95.
Xing R et al., Copy number variations of HLA-I and activation of NKp30 pathway determine the sensitivity of gastric cancer cells to the cytotoxicity of natural killer cells, ONCOGENE (2015), vol. 35, No. 20, doi:10.1038/onc.2015.324, ISSN 0950-9232, pp. 2584-2591.
Yap K L et al., Whole-Exome Sequencing of Muscle-Invasive Bladder Cancer Identifies Recurrent Mutations of UNC5C and Prognostic Importance of DNA Repair Gene Mutations on Survival, Clinical Cancer Research, 2014, 20:6605.
Ye et al., Engineered artificial antigen presenting cells facilitate direct and efficient expansion of tumor infiltrating lymphocytes, J Transl Med. Aug. 9, 2011;9:131.
Yoshihama et al., (2016). NLRC5/MHC class I transactivator is a target for immune evasion in cancer. Proceedings of the National Academy of Sciences of the United States of America 113, 5999-6004.

\* cited by examiner

G

H

ANALYSIS OF HLA ALLELES IN TUMOURS AND THE USES THEREOF

CROSS-REFERENCE TO RELATED APPLICATIONS

This application is a U.S. National Phase of International Patent Application No. PCT/GB2018/052004, filed on Jul. 13, 2018, which claims priority benefit of United Kingdom Patent Application Nos. 1716079.7, filed on Oct. 2, 2017, and 1711349.9, filed on Jul. 14, 2017.

FIELD OF THE INVENTION

The present invention relates to a method for determining whether an HLA allele is lost in a tumour in a subject, wherein said method comprises the step of determining the specific copy number of said HLA allele in said tumour. The invention also relates to a method for treating cancer in a subject, comprising targeting a neoantigen which is predicted to be presented by an HLA molecule encoded by an HLA allele which has been determined not to have been lost in a tumour in said subject.

BACKGROUND

Immune evasion represents a hallmark of cancer. Cancer cells adopt a variety of mechanisms to evade the immune system in order to avoid T-cell recognition. Cancer immunotherapies aim to counteract this immune evasion by shifting the balance in favour of immune activation, enabling cancer cell elimination. However, only a subset of patients benefit from immunotherapies, emphasizing the need to identify the genomic and molecular determinants underpinning immune evasion.

SUMMARY OF THE INVENTION

An important aspect of immunity is the human leukocyte antigen (HLA) system. HLA genes encode proteins that present antigens to the immune system.

Down-regulation of these HLA genes may result in reduced antigen presentation and thus facilitate immune evasion. HLA down-regulation, characterized by immunohistochemistry, has been found to be prevalent across a range of cancer types and has also been linked to poor outcome. Loss of either the maternal or paternal HLA haplotypes may also impact upon the efficacy of immunotherapy.

However, the impact of loss of HLA haplotypes on anti-tumour immunity, clonal expansions and neo-antigen prediction has not been systematically explored as the polymorphic nature of the HLA locus prevents alignments of sequencing reads to the human reference genome and inference of copy number. This polymorphic nature of the HLA locus represents a hurdle to sequence-based methods of determining specific HLA loss. Indeed, previous methods used in the past have employed antibodies to detect HLA type, see for example Hiraki et al. (Anticancer Research 24:1525-1528, 2004), wherein allele-specific HLA class I expression was analysed using a panel of monoclonal antibodies. Such methods are clearly labour intensive and costly, and not effective for use on a large scale or in clinics.

The present inventors have developed a method that overcomes the limitations inherent to current sequence-based methods that are unable to determine specific HLA copy number profiles. The present invention allows determination of which particular HLA allele may have been lost.

The present invention therefore provides an important contribution to the art, in that it facilitates a simple, quick, convenient and accurate determination of HLA specific copy number loss which could be used routinely and in a clinical setting. The present invention is less labour intensive and more cost effective than laboratory-based methods, and provides the additional advantage that historic sequencing information from a patient's tumour can be used, so that patients do not have to undergo a second biopsy.

Thus, prior to the present invention, it has not been possible to analyse the prevalence and complexity of HLA loss in the cancer context. Existing methods do not enable inference of haplotype specific copy number of the HLA locus in a tumour. When designing therapies which target neoantigens in the cancer setting, it is important to know with a high degree of certainty whether an HLA allele has been lost or not, in order to target neoantigens that are actually presented to the immune system. Previous methods do not enable such determination.

The present invention now provides an accurate method for determining whether an HLA allele is lost or not in a tumour. Crucially, the method allows specific determination of which HLA allele is subject to loss at each HLA gene. The method enables accurate determination of the HLA allele profile within a tumour, which facilitates the design of improved therapies that target neoantigens in cancer.

It is important to be able to determine the copy number of specific HLA alleles in order to design therapies that target neoantigens predicted to be presented by the specific HLA molecules encoded by the HLA alleles that are present. It is important to know which specific HLA allele type is lost, but also which specific HLA allele type is present in the tumour, in order that therapies can be designed to target neoantigens presented by an HLA molecule encoded by that specific HLA allele that is present. The present invention provides an improved method for determining copy number loss of specific HLA alleles in a subject.

Methods known in the art, such as Polysolver, only determine functional HLA loss by mutation, and do not assess copy number loss. It is advantageous, for example when designing therapies, to determine copy number loss rather than loss of function by mutation, as loss of function by mutation occurs in only a very small percentage of tumours, whereas copy number loss occurs in a much larger (40%) of tumours (for example see FIG. 4 herein, and also McGranahan et al. Cell 171:1259-1271 2017 and Shukla et al. Nature Biotechnology 33:1152-1158 2015).

The invention also provides a method for treating cancer in a subject comprising targeting a neoantigen which is predicted to be presented by an HLA molecule encoded by an HLA allele which has been determined not to have been lost in a tumour.

DETAILED DESCRIPTION

Figure 1:
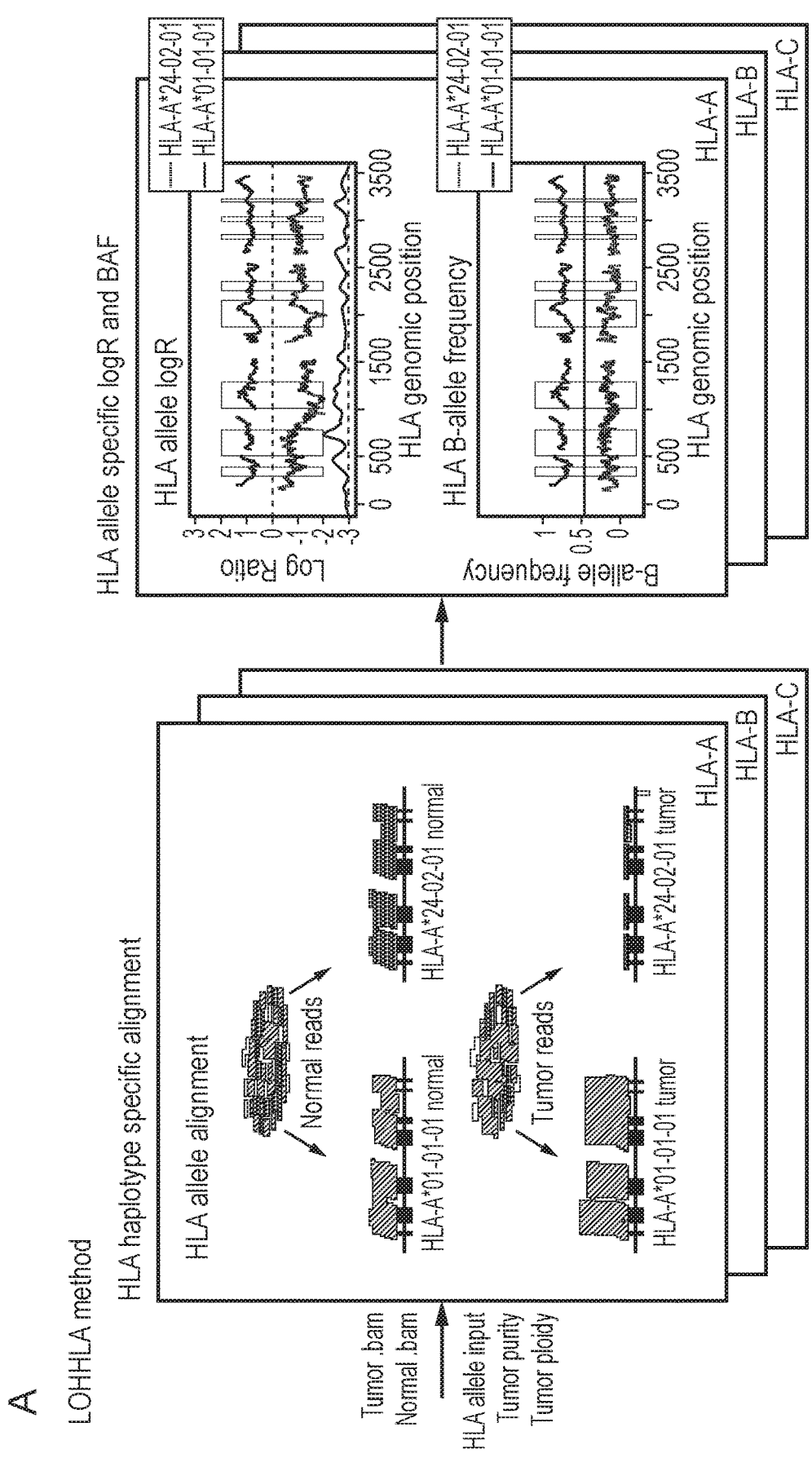
FIG. 1: Outline and validation of LOHHLA for inference of HLA class I allele specific copy number in tumours. A) Schematic of the LOHHLA algorithm. B) Comparison of minor allele copy number for ASCAT and LOHHLA. C) Venn diagram illustrating LOHHLA and ASCAT comparison for inference of allelic imbalance at HLA locus. D) Venn diagram illustrating LOHHLA and ASCAT comparison for inference of LOH at HLA locus.
Figure 1:
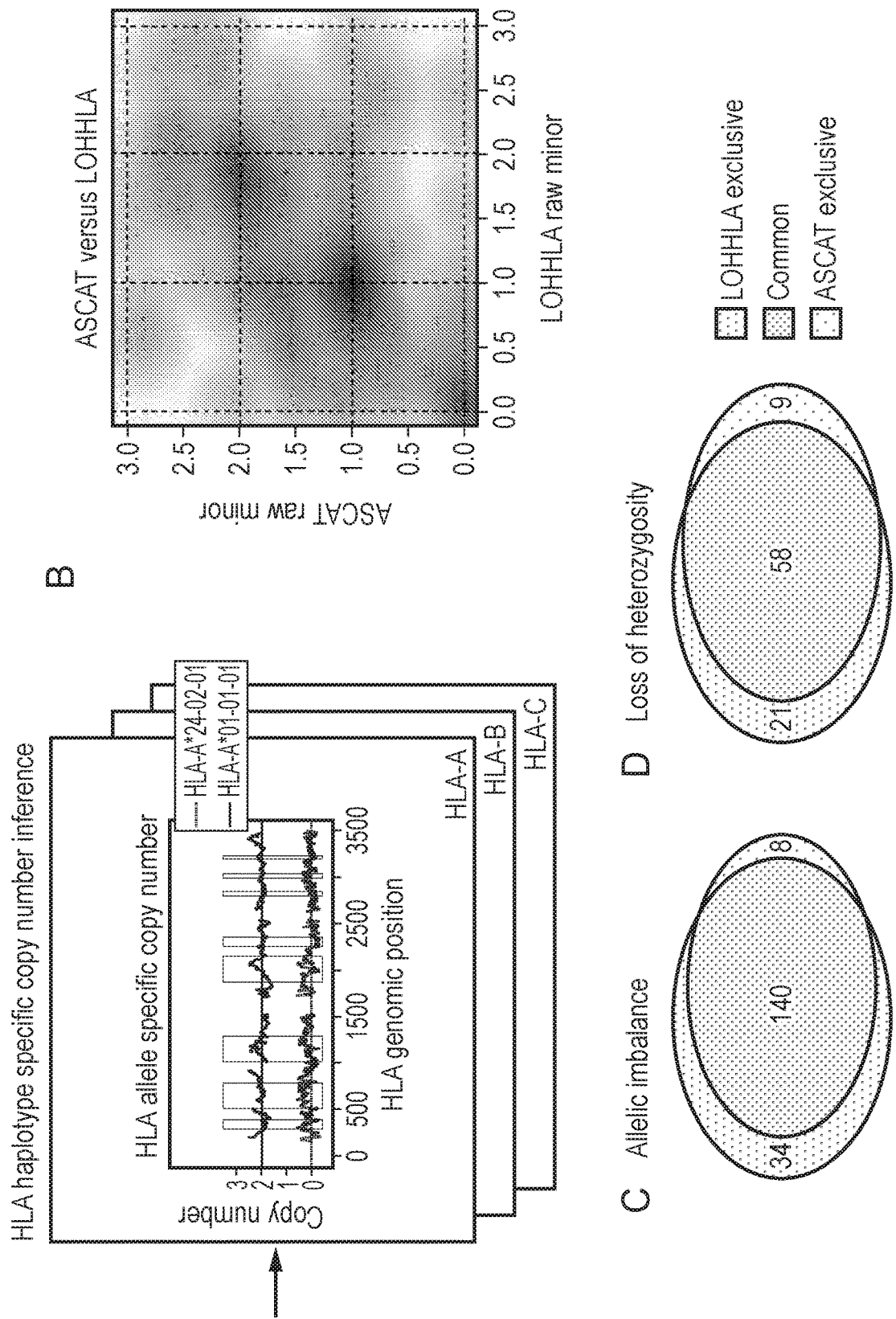

The present invention provides a method for determining whether an HLA allele is lost in a tumour. Knowledge of HLA expression can inform design of therapies targeting particular antigens, such as neoantigens as described herein, which are predicted to be presented by an HLA molecule encoded by an HLA allele which has not been lost, i.e. to avoid designing therapies targeting neoantigens that will not be presented to the immune system, and will not elicit an immune response to the tumour.

Method for Determining Whether an HLA Allele is Lost in a Tumour

In one aspect the invention provides a method for determining whether an HLA allele is lost in a tumour, wherein said method comprises the step of determining the specific copy number of said HLA allele in a sample from said tumour. As discussed herein, the present invention enables an effective method of determining the copy number of specific HLA alleles in a tumour, and this represents an important step in the method.

The method may be carried out on sequence information from a tumour sample from a subject. In one aspect the method may be carried out on HLA sequence information from a tumour sample from a subject.

By "loss" as used herein is meant copy number loss or deletion of the HLA allele, rather than loss of function due to mutation.

Determination of the HLA allele specific copy number is important for generating a higher level of certainty regarding HLA allele loss in a tumour, as opposed to, for example, analysing only the ratio or allelic imbalance of HLA alleles in a tumour. The present invention is predicated on the fact that, in view of the surprising prevalence and complexity of HLA loss in tumours, it is important to determine the HLA allele specific copy number in order to design therapies that are more likely to target neoantigens that are presented to the immune system. The method according to the present invention enables for the first time, the analysis of HLA allele specific copy number in a tumour and hence accurate determination of whether a particular HLA allele has been lost.

In one aspect the method according to the invention may comprise one or more of the following steps:
  (i) aligning HLA allele sequence information from a tumour sample from a subject with an HLA allele reference sequence which is based on said subject's HLA type;
  (ii) determining mismatch positions in homologous HLA alleles, and determining mismatch coverage for each HLA allele;
  (iii) determining the ratio and allele frequency of each HLA allele based on mismatches and coverage determined in step (ii);
  (iv) determining the copy number of each HLA allele in the tumour sample based on the ratio and allele frequency determined in step (iii).

One skilled in the art will be aware of ways of carrying out such steps.

For example, the sequence information referred to in step (i) may be obtained by standard nucleic acid sequencing methods. We refer, for example, to Mardis, 2013 Annu. Rev. Anal. Chem. 6:287-303.

Methods for HLA type determination are also known in the art, for example as described in Shukla, 2016 Nature Biotechnology 33, 1152-1158; Szolek, 2014 Bioinformatics 30, 3310-3316; and Warren, 2012 Genome Medicine 4, 95.

The HLA profile of an individual may be determined by HLA-serotyping and/or HLA gene sequencing. HLA-phenotyping with single specific primer-PCR (SSP-PCR) is an alternative strategy for determining the HLA profile of an individual. The HLA profile of an individual may be determined by sequencing of the HLA locus and processing, for example using the Optitype prediction algorithm to determine the HLA type.

In one aspect, step (i) may be carried out according to the method as set out in Example 1, i.e. encompassing the first and second bioinformatics steps. Thus, step (i) above may encompass extracting HLA reads and creating HLA allele specific BAM files.

Step (ii) may be performed using the Smith-Waterman algorithm, or the Biostrings R package.

Step (iii) may be performed using methods known in the art, for example as described in Li 2009 Bioinformatics 25, 2078-2079, and Li 2011 Bioinformatics 27, 2987-2993 (SAMtools). By "coverage" is meant the number of times the sequence has been determined. This is a standard term in the technical field of the invention and will be understood by one skilled in the art.

Step (iv) may be performed using methods known in art to infer specific copy number status by taking into account tumour purity and/or ploidy, for example by ASCAT (Van Loo 2010, PNAS 107, 16910-16915), FACETs (Shen 2016, Nucleic Acids Res 44, e131). By "tumour purity" is meant the proportion of cancer cells relative to other cells in the sample that have been sequenced. By "tumour ploidy" is meant the number of genome copies (or chromosome sets) a cell has.

Determination of the HLA allele specific copy number enables determination of whether the HLA allele has been lost in the tumour.

A method according to the invention allows inference of HLA haplotype specific copy number of the HLA locus, and thus which specific HLA haplotype may be subject to loss in a tumour.

In one aspect the method may be carried out as described in the Examples herein.

Sample

As referred to herein a "germline" sample refers to non-tumour sample, such as a blood sample, tissue sample or peripheral blood mononuclear cells from the subject.

In one aspect the sample may be a blood sample. The sample may contain a blood fraction (e.g. a serum sample or a plasma sample) or may be whole blood. Techniques for collecting samples from a subject are well known in the art.

As referred to herein, a "tumour sample" refers to a sample deriving or obtained from a tumour. The tumour may be a solid tumour or a non-solid or haematological tumour.

Isolation of biopsies and samples from tumours is common practice in the art and may be performed according to any suitable method, and such methods will be known to one skilled in the art.

The tumour sample may be a primary tumour sample, tumour-associated lymph node sample or sample from a metastatic site from the subject.

In certain embodiments the sample is a tumour-associated body fluid or tissue.

Suitably, the sample may be circulating tumour DNA, circulating tumour cells or exosomes comprising tumour DNA. The circulating tumour DNA, circulating tumour cells or exosomes comprising tumour DNA may be isolated from a blood sample obtained from the subject using methods which are known in the art.

Tumour samples and non-cancerous tissue samples can be obtained according to any method known in the art. For example, tumour and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor. ctDNA and circulating tumour cells may be isolated from blood samples according to e.g. *Nature.* 2017 Apr. 26; 545(7655):446-451 or *Nat Med.* 2017 January; 23(1):114-119.

DNA and/or RNA suitable for downstream sequencing can be isolated from a sample using methods which are known in the art. For example DNA and/or RNA isolation may be performed using phenol-based extraction. Phenol-based reagents contain a combination of denaturants and RNase inhibitors for cell and tissue disruption and subsequent separation of DNA or RNA from contaminants. For example, extraction procedures such as those using DNA-zol™, TRIZOL™ or TRI REAGENT™ may be used. DNA and/or RNA may further be isolated using solid phase extraction methods (e.g. spin columns) such as PureLink™ Genomic DNA Mini Kit or QIAGEN RNeasy™ methods. Isolated RNA may be converted to cDNA for downstream sequencing using methods which are known in the art (RT-PCR).

In one aspect more than one sample is obtained and analysed, for example 2, 3, 4, 5, 6, 7, 8, 9, or 10 samples.

In one aspect, it may be necessary to test a sample from both the primary tumour site and one or more metastatic sites. In one aspect the sample from the primary tumour site may not be representative of the cancer cells at a metastatic site. As such, the methods and uses of the invention as described herein may involve determination of HLA loss at both the primary and metastatic sites of a tumour.

HLA and Neoantigen Presentation

The human leukocyte antigen (HLA) system is a gene complex encoding the major histocompatibility complex (MHC) proteins in humans. These cell-surface proteins regulate the immune system in humans. The HLA gene complex resides on a 3 Mbp stretch within chromosome 6p21. HLA genes are highly polymorphic, which means that they have many different alleles, allowing them to fine-tune the adaptive immune system. At each HLA locus there may be thousands of possible alleles, for example as described in Shiina et al. Journal of Human Genetics (2009) 54, 15-39.

As used herein, the term "HLA allele" is intended to refer to any allele at the HLA locus.

HLAs corresponding to MHC class I (A, B, and C) present peptides from inside the cell. These peptides are produced from digested proteins that are broken down in the proteasomes. In general, the peptides are small polymers, about 8-11 amino acids in length. Foreign antigens presented by MHC class I attract killer T-cells that destroy cells.

In one aspect the present invention relates to HLA class I, in that peptides from within cancerous cells may be presented on the cell's surface by MHC class I proteins.

In one aspect of the invention as described herein the HLA is a class I HLA. In one aspect the HLA is HLA-A. In one aspect the HLA is HLA-B. In one aspect the HLA is HLA-C. In one aspect the HLA is a class I HLA selected from HLA-A, HLA-B and HLA-C.

HLA class I also includes HLA-E, HLA-F and HLA-G.

HLAs corresponding to MHC class II (DP, DM, DOA, DOB, DQ, and DR) present antigens from outside of the cell to T-lymphocytes. MHC class II molecules are normally found on antigen-presenting cells such as dendritic cells, mononuclear phagocytes, some endothelial cells, thymic epithelial cells, and B cells. These cells are important in initiating immune responses. These molecules may also be induced on other cells by interferon γ.

In one aspect the HLA may be a class II HLA, for example selected from HLA-DP, HLA-DM, HLA-DOA, HLA-DOB, HLA-DQ, and HLA-DR. In one aspect the HLA is HLA-DP. In one aspect the HLA is HLA-DM. In one aspect the HLA is HLA-DOA. In one aspect the HLA is HLA-DOB. In one aspect the HLA is HLA-DQ. In one aspect the HLA is HLA-DR.

Methods for HLA typing are known in the art, for example Polysolver or OptiType as mentioned herein.

Antigens that are presented by the HLA system may be neoantigens. A neoantigen is a newly formed antigen that has not been previously presented to the immune system. A neoantigen is a tumour-specific antigen which arises as a consequence of a mutation within a cancer cell. Thus, a neoantigen is not expressed by healthy (i.e. non-tumour cells). A neoantigen may be processed to generate distinct peptides which can be recognised by T cells when presented in the context of MHC molecules. As described herein, neoantigens may be used as the basis for cancer therapies.

Methods for identifying or predicting neoantigens are known in the art, for example as described in Nielsen, 2016; Hoof, 2009; and Hundal, 2016.

The binding of a neoantigen to a particular MHC molecule (encoded by a particular HLA allele) may be predicted using methods which are known in the art. Examples of methods for predicting MHC binding include those described by Lundegaard et al. (Nucleic Acids Res. 2008: W509-12.2008 & Bioinformatics. 2008 Jun. 1; 24(11):1397-8) and Shen et al. (Proteome Sci. 2013 Nov. 7; 11(Suppl 1):S15). In the present Examples, MHC binding of neoantigens is predicted using the netMHC and netMHCpan algorithms.

The predicted binding affinity of the MHC molecule to a neoantigen peptide sequence may be below 500 nM. By "high affinity" may mean 0 to 50 nM binding affinity. In other embodiments the neoantigen peptide may be predicted to bind the MHC molecule with an intermediate affinity of 50 to 150 nM binding affinity, or low affinity of 150 to 500 nM binding affinity.

A neoantigen that has been predicted to bind to a particular MHC molecule is thereby predicted to be presented by said MHC molecule on the cell surface.

In one aspect the invention provides a method for determining whether a neoantigen is predicted to be presented by a tumour comprising the steps of:
 (i) identifying a neoantigen in a tumour; and
 (ii) determining whether said neoantigen is predicted to be presented by an HLA molecule encoded by an HLA allele that has not been lost in said tumour.

The second step may be carried out by a method according to the invention as described herein.

In one aspect the invention provides a method for identifying a target neoantigen for cancer therapy, comprising the steps of:
 (i) identifying a neoantigen in a tumour;
 (ii) determining whether said neoantigen is predicted to be presented by an HLA molecule encoded by an HLA allele that has been lost in said tumour; and
 (iii) discounting neoantigens as targets which are predicted to be presented by an HLA molecule encoded by an HLA allele that has been lost in said tumour.

In one aspect is provided a method for identifying a target neoantigen for cancer therapy, comprising the steps of:
 (i) determining whether a tumour neoantigen is predicted to be presented by an HLA molecule encoded by an HLA allele that has been lost in said tumour; and
 (ii) discounting neoantigens as targets which are predicted to be presented by an HLA molecule encoded by an HLA allele that has been lost in said tumour.

It is possible that neoantigens may be predicted to bind to more than one HLA allele, wherein one HLA allele may be lost in a tumour, but the other HLA allele is not lost in a tumour. In that case, the neoantigen may still be a target for cancer therapy and need not be discounted.

As such, the methods above may comprise a step of discounting neoantigens as targets which are predicted to only be presented by HLA alleles that have been lost in said tumour. Neoantigens may be retained as targets if they are predicted to be presented by at least one HLA allele that is not lost in a tumour.

In one aspect is provided a method for identifying a target neoantigen for cancer therapy, comprising the steps of:
 (i) determining whether a tumour neoantigen is predicted to be presented by an HLA molecule encoded by an HLA allele that has been lost in said tumour; and
 (ii) discounting neoantigens as targets which are predicted to be presented only by HLA alleles that have been lost in said tumour, wherein neoantigens that are predicted to be presented by at least one HLA molecule encoded by an HLA allele that has not been lost in a tumour are not discounted as a target.

Alternatively put, neoantigens may be identified as a target for cancer therapy if they are predicted to be presented by at least one HLA molecule encoded by an HLA allele that is not lost in a tumour.

Target neoantigens identified according to the methods herein may be a target for any of the methods of treatment and corresponding uses according to the invention as described herein.

In one aspect of the methods herein, the HLA allele that has not been lost (or which has been lost in the case where neoantigens are discounted) has been determined not to have been lost in at least one sample from a tumour. In one aspect said HLA has been determined not to have been lost in 2, 3, 4, 5, 6, 7, 8, 9 or 10 samples from said tumour.

Targeting Neoantigens

According to the present invention, neoantigens that are predicted to be presented by an HLA molecule encoded by an HLA allele which has been determined not to have been lost in a tumour may represent a target for therapeutic or prophylactic intervention in the treatment or prevention of cancer in a subject.

References herein to "neoantigens" are intended to include also peptides derived from neoantigens.

The methods of the invention may be used in vitro or in vivo, for example either for in situ treatment or for ex vivo treatment followed by the administration of the treated cells to the subject.

By "targeting a neoantigen" is meant that a therapeutic or prophylactic intervention is based on such a neoantigen.

This is discussed in further detail below, but in brief may comprise an active immunotherapy approach, such as administering an immunogenic composition or vaccine comprising a neoantigen to a subject. Alternatively, a passive immunotherapy approach may be taken, for example adoptive T cell transfer or B cell transfer, wherein a T or B cell or T and B cells which recognise a neoantigen are isolated from tumours, or other bodily tissues (including but not limited to lymph node, blood or ascites), expanded ex vivo or in vitro and readministered to a subject.

In a further alternative an antibody which recognises a neoantigen may be administered to a subject. One skilled in the art will appreciate that if the neoantigen is a cell surface antigen, an antibody as referred to herein will recognise the neoantigen. Where the neoantigen is an intracellular antigen, the antibody will recognise the neoantigen peptide:MHC complex. As referred to here in, an antibody which "recognises" a neoantigen encompasses both of these possibilities.

As such, in one aspect the invention is directed to a method of treating or preventing cancer in a subject, comprising administering to said subject:
(i) a neoantigen that is predicted to be presented by an HLA molecule encoded by an HLA allele which has been determined not to have been lost in a tumour;
(ii) an immune cell which recognises a neoantigen that is predicted to be presented by an HLA molecule encoded by an HLA allele which has been determined not to have been lost in a tumour; or
(iii) an antibody which recognises a neoantigen that is predicted to be presented by an HLA molecule encoded by an HLA allele which has been determined not to have been lost in a tumour.

In another aspect the invention provides a neoantigen that is predicted to be presented by an HLA molecule encoded by an HLA allele which has been determined not to have been lost in a tumour for use in the treatment or prevention of cancer in a subject. Alternatively put, the invention provides the use of a neoantigen that is predicted to be presented by an HLA molecule encoded by an HLA allele which has been determined not to have been lost in a tumour in the manufacture of a medicament for use in the treatment or prevention of cancer in a subject. In a further alternative the invention provides the use of a neoantigen that is predicted to be presented by an HLA molecule encoded by an HLA allele which has been determined not to have been lost in a tumour in treating or preventing cancer in a subject.

In a further aspect the invention provides an immune cell, preferably a T cell which recognises a neoantigen that is predicted to be presented by an HLA molecule encoded by an HLA allele which has been determined not to have been lost in a tumour for use in the treatment or prevention of cancer in a subject. Alternatively put, the invention provides the use of an immune cell, preferably a T cell, which recognises a neoantigen that is predicted to be presented by an HLA molecule encoded by an HLA allele which has been determined not to have been lost in a tumour in the manufacture of a medicament for use in the treatment or prevention of cancer in a subject. In a further alternative the invention provides the use of an immune cell, preferably a T cell, which recognises a neoantigen that is predicted to be presented by an HLA molecule encoded by an HLA allele which has been determined not to have been lost in a tumour in treating or preventing cancer in a subject.

References to "an immune cell" are intended to encompass cells of the immune system, for example T cells, NK cells, NKT cells, B cells and dendritic cells. In a preferred embodiment the immune cell is a T cell, as discussed herein.

In a further aspect the invention provides an antibody which recognises a neoantigen that is predicted to be presented by an HLA molecule encoded by an HLA allele which has been determined not to have been lost in a tumour for use in the treatment or prevention of cancer in a subject. Alternatively put, the invention provides the use of an antibody which recognises a neoantigen that is predicted to be presented by an HLA molecule encoded by an HLA allele which has been determined not to have been lost in a tumour in the manufacture of a medicament for use in the treatment or prevention of cancer in a subject. In a further alternative the invention provides the use of an antibody which recognises a neoantigen that is predicted to be presented by an HLA molecule encoded by an HLA allele which has been determined not to have been lost in a tumour in treating or preventing cancer in a subject.

In one aspect the specific HLA allele is or has been determined to have been lost by a sequence-based method. By "sequence-based method" is meant a method involving genetic sequence information, i.e. providing genetic sequence information, for example by massively parallel sequencing, deep sequencing, high-throughput sequencing, Next Generation Sequencing (NGS), second-generation sequencing or any suitable methods known in the art.

In one aspect the specific HLA allele is or has been determined to have been lost by a sequence-based method carried out on HLA allele sequence information from said subject. The method may be a method according to the invention as described herein.

Neoantigens

A "neo-antigen" is a tumour-specific antigen which arises as a consequence of a mutation within a cancer cell. Thus, a neo-antigen is not expressed by healthy cells in a subject.

The neo-antigen described herein may be caused by any non-silent mutation which alters a protein expressed by a cancer cell compared to the non-mutated protein expressed by a wild-type, healthy cell. For example, the mutated protein may be a translocation or fusion.

A "mutation" refers to a difference in a nucleotide sequence (e.g. DNA or RNA) in a tumour cell compared to a healthy cell from the same individual. The difference in the nucleotide sequence can result in the expression of a protein which is not expressed by a healthy cell from the same individual.

For example, the mutation may be a single nucleotide variant (SNV), multiple nucleotide variants, a deletion mutation, an insertion mutation, a translocation, a missense mutation or a splice site mutation resulting in a change in the amino acid sequence (coding mutation).

The mutations may be identified by Exome sequencing, RNA-seq, whole genome sequencing and/or targeted gene panel sequencing and or routine Sanger sequencing of single genes. Suitable methods are known in the art.

Descriptions of Exome sequencing and RNA-seq are provided by Boa et al. (Cancer Informatics. 2014; 13(Suppl 2):67-82) and Ares et al. (Cold Spring Harb Protoc. 2014 Nov. 3; 2014(11):1139-48); respectively. Descriptions of targeted gene panel sequencing can be found in, for example, Kammermeier et al. (J Med Genet. 2014 November; 51(11):748-55) and Yap K L et al. (Clin Cancer Res. 2014. 20:6605). See also Meyerson et al., Nat. Rev. Genetics, 2010 and Mardis, Annu Rev Anal Chem, 2013. Targeted gene sequencing panels are also commercially available (e.g. as summarised by Biocompare ((http://www.biocompare.com/Editorial-Articles/161194-Build-Your-Own-Gene-Panels-with-These-Custom-NGS-Targeting-Tools/)).

Sequence alignment to identify nucleotide differences (e.g. SNVs) in DNA and/or RNA from a tumour sample compared to DNA and/or RNA from a non-tumour sample may be performed using methods which are known in the art. For example, nucleotide differences compared to a reference sample may be performed using the method described by Koboldt et al. (Genome Res. 2012; 22: 568-576). The reference sample may be the germline DNA and/or RNA sequence.

In one aspect the neoantigen may be a clonal neoantigen.

A "clonal" neoantigen is a neoantigen which is expressed effectively throughout a tumour and encoded within essentially every tumour cell. A "sub-clonal" neoantigen' is a neoantigen which is expressed in a subset or a proportion of cells or regions in a tumour.

'Present throughout a tumour', 'expressed effectively throughout a tumour' and 'encoded within essentially every tumour cell' may mean that the clonal neoantigen is expressed in all regions of the tumour from which samples are analysed.

It will be appreciated that a determination that a mutation is 'encoded within essentially every tumour cell' refers to a statistical calculation and is therefore subject to statistical analysis and thresholds.

Likewise, a determination that a clonal neoantigen is 'expressed effectively throughout a tumour' refers to a statistical calculation and is therefore subject to statistical analysis and thresholds.

Expressed effectively in essentially every tumour cell, or essentially all tumour cells, means that the mutation is present in all tumour cells analysed in a sample, as determined using appropriate statistical methods.

By way of the example, the cancer cell fraction (CCF), describing the proportion of cancer cells that harbour a mutation may be used to determine whether mutations are clonal or sub-clonal. For example, the cancer cell fraction may be determined by integrating variant allele frequencies with copy numbers and purity estimates as described by Landau et al. (Cell. 2013 Feb. 14; 152(4):714-26).

Suitably, CCF values may be calculated for all mutations identified within each and every tumour region analysed. If only one region is used (i.e. only a single sample), only one set of CCF values will be obtained. This will provide information as to which mutations are present in all tumour cells within that tumour region, and will thereby provide an indication if the mutation is clonal or sub-clonal.

As stated, determining a clonal mutation is subject to statistical analysis and threshold. As such, a mutation may be identified as clonal if it is determined to have a CCF 95% confidence interval >=0.75, for example 0.80, 0.85, 0.90, 0.95, 1.00 or >1.00. Conversely, a mutation may be identified as sub-clonal if it is determined to have a CCF 95% confidence interval <=0.75, for example 0.70, 0.65, 0.60, 0.55, 0.50, 0.45, 0.40, 0.35, 0.30, 0.25, 0.20, 0.15, 0.10, 0.05, 0.01 in any sample analysed.

It will be appreciated that the accuracy of a method for identifying clonal mutations is increased by identifying clonal mutations for more than one sample isolated from the tumour.

In one embodiment the methods may involve identifying a plurality i.e. more than one clonal neo-antigen.

In one embodiment the number of clonal neo-antigens is 2-1000. For example, the number of clonal neo-antigens may be 2, 3, 4, 5, 6, 7, 8, 9, 10, 20, 50, 100, 150, 200, 250, 300, 350, 400, 450, 500, 550, 600, 650, 700, 750, 800, 850, 900, 950 or 1000, for example the number of clonal neo-antigens may be from 2 to 100.

In one aspect, the methods as described herein may provide a plurality or population, i.e. more than one, of T cells wherein the plurality of T cells comprises a T cell which recognises a clonal neo-antigen and a T cell which recognises a different clonal neo-antigen. As such, the method provides a plurality of T cells which recognise different clonal neo-antigens.

In a preferred embodiment the number of clonal neo-antigens recognised by the plurality of T cells is 2-1000. For example, the number of clonal neo-antigens recognised may be 2, 3, 4, 5, 6, 7, 8, 9, 10, 20, 50, 100, 150, 200, 250, 300, 350, 400, 450, 500, 550, 600, 650, 700, 750, 800, 850, 900, 950 or 1000, for example the number of clonal neo-antigens recognised may be from 2 to 100.

In one aspect a plurality of T cells recognises the same clonal neo-antigen.

In one aspect the neoantigen may be a sub-clonal neoantigen as described herein.

As described above, a clonal neoantigen is one which is encoded within essentially every tumour cell, that is the mutation encoding the neoantigen is present within essentially every tumour cell. However, as described herein, a clonal neoantigen may be predicted to be presented by an HLA molecule encoded by an HLA allele which is lost in a tumour. In which case, the clonal neoantigen may not actually be presented on essentially every tumour cell. As such, the presentation of the neoantigen may not be clonal, i.e. it is not presented within essentially every tumour cell.

In one aspect of the invention as described herein the neoantigen is predicted to be presented within essentially every tumour cell (i.e. the presentation of the neoantigen is clonal).

In one aspect the neoantigen is predicted to be not presented within essentially every tumour cell, that is to say the presentation of the neoantigen is sub-clonal. As such, a clonal neoantigen may be presented sub-clonally.

Whether a neoantigen is presented clonally or sub-clonally may be determined using the methods described above in respect of clonal mutation determination, i.e. the CCF fraction may alternatively describe the proportion of cancer cells that present a specific neoantigen may be used to determine whether presentation of the neoantigen is clonal or sub-clonal.

As stated, determining a clonal presentation is subject to statistical analysis and threshold. As such, presentation may be identified as clonal if it is determined to have a CCF 95% confidence interval >=0.75, for example 0.80, 0.85, 0.90, 0.95, 1.00 or >1.00. Conversely, presentation may be identified as sub-clonal if it is determined to have a CCF 95% confidence interval <=0.75, for example 0.70, 0.65, 0.60, 0.55, 0.50, 0.45, 0.40, 0.35, 0.30, 0.25, 0.20, 0.15, 0.10, 0.05, 0.01 in any sample analysed.

In one aspect the neoantigen may be the result of an indel mutation (an indel neoantigen).

An "indel mutation" as referred to herein refers to an insertion and/or deletion of bases in a nucleotide sequence (e.g. DNA or RNA) of an organism. Typically, the indel mutation occurs in the DNA, preferably the genomic DNA, of an organism. Suitably, the indel mutation occurs in the genomic DNA of a tumour cell in the subject. Suitably, the indel may be an insertion mutation. Suitably, the indel may be a deletion mutation.

Suitably, the indel may be from 1 to 100 bases, for example 1 to 90, 1 to 50, 1 to 23 or 1 to 10 bases.

In one aspect, the indel mutation may be a frameshift indel mutation. A frameshift indel mutation is a change in the reading frame of the nucleotide sequence caused by an insertion or deletion of one or more nucleotides. Such frameshift indel mutations may generate a novel open-reading frame which is typically highly distinct from the polypeptide encoded by the non-mutated DNA/RNA in a corresponding healthy cell in the subject.

Frameshift mutations typically introduce premature termination codons (PTCs) into the open reading frame and the resultant mRNAs are targeted for nonsense mediated decay (NMD).

In one aspect, indel frameshift mutations may be, or may not be, targeted for NMD.

In one aspect the indel neoantigen is a clonal neoantigen. That is, the indel mutation generates a clonal indel neoantigen. The clonal indel neoantigen may be a frameshift, that is a clonal frameshift indel neoantigen.

In one aspect the indel is a non-frameshift indel.

Neoantigen Peptides

The term "neoantigen" as used herein is intended to encompass any part of a neoantigen that is immunogenic. This may include peptides derived from a neoantigen. An "antigenic" molecule as referred to herein is a molecule which itself, or a part thereof, is capable of stimulating an immune response, when presented to the immune system or immune cells in an appropriate manner.

Neoantigen peptides may be synthesised using methods which are known in the art.

The term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

The peptide may be made using chemical methods (Peptide Chemistry, A practical Textbook. Mikos Bodansky, Springer-Verlag, Berlin). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from the polypeptide which is or comprises the neoantigen. The composition of a peptide may be confirmed by amino acid analysis or sequencing (e.g., the Edman degradation procedure).

The neoantigen peptide may comprise the cancer cell specific mutation (e.g. the non-silent amino acid substitution encoded by a single nucleotide variant (SNV)) at any residue position within the peptide. By way of example, a peptide which is capable of binding to an MHC class I molecule is typically 7 to 13 amino acids in length. As such, the amino acid substitution may be present at position 1, 2, 3, 4, 5, 6, 7, 8, 9, 10, 11, 12 or 13 in a peptide comprising thirteen amino acids.

In a further aspect, longer peptides, for example 21-31 mers, may be used, and the mutation may be at any position, for example at the centre of the peptide, e.g. at positions 13, 14, 15 or 16 can also be used to stimulate both CD4 and CD8 cells to recognise neoantigens.

T Cell and T Cell Population

As discussed herein, the present invention encompasses therapeutic utilities of a T cell which recognises a neoantigen that is predicted to be presented by an HLA molecule encoded by an HLA allele which has been determined not to have been lost in a tumour, and also for methods for providing such a T cell or population thereof.

The invention encompasses a method for providing a T cell which is specific to a neoantigen that is predicted to be presented by an HLA molecule encoded by an HLA allele which has been determined not to have been lost in a tumour, wherein said method comprises the following steps:

i) identifying a neoantigen that is predicted to be presented by an HLA molecule encoded by an HLA allele that has been determined not to have been lost in a tumour; and iv) providing a T cell or population of T cells which recognises said neoantigen.

In one aspect determination of HLA loss may be performed by a method according to the invention as described herein.

In one aspect of the invention as described herein mutations may be determined in a plurality of samples isolated from the tumour.

The T cell population may be expanded in order to increase the number of T cells which recognise or target a neoantigen that is predicted to be presented by an HLA molecule encoded by an HLA allele which has been determined not to have been lost in a tumour. Expansion of T cells may be performed using methods which are known in the art.

For example, T cells may be expanded by ex vivo culture in conditions which are known to provide mitogenic stimuli for T cells. By way of example, the T cells may be cultured with cytokines such as IL-2 or with mitogenic antibodies such as anti-CD3 and/or CD28. The T cells may be co-cultured with antigen-presenting cells (APCs), which may have been irradiated. The APCs may be dendritic cells or B cells. The dendritic cells may have been pulsed with peptides containing the identified neoantigen as single stimulants or as pools of stimulating neoantigen peptides. Expansion of T cells may be performed using methods which are known in the art, including for example the use of artificial antigen presenting cells (aAPCs), which provide additional co-stimulatory signals, and autologous PBMCs which present appropriate peptides. Autologous PBMCs may be pulsed with peptides containing neoantigens as discussed herein as single stimulants, or alternatively as pools of stimulating neoantigens.

In one aspect the invention provides a method for expanding a T cell population for use in the treatment of cancer in a subject, wherein the T cell population targets a neo-antigen that is predicted to be presented by an HLA molecule encoded by an HLA allele which has been determined not to have been lost in a tumour, the method comprising the steps of:

a) providing a T cell population comprising a T cell which is capable of specifically recognising said neo-antigen; and b) co-culturing the T cell population with a composition comprising the neo-antigen.

In one aspect expansion may be performed by co-culture of a T cell with a neoantigen and an antigen presenting cell. The antigen presenting cell may be a dendritic cell. The neo-antigen may be a clonal neo-antigen. The expansion may be a selective expansion of T cells which are specific for the neoantigen.

The invention provides a method for producing a composition comprising an antigen presenting cell and a neo-antigen or a neo-antigen peptide wherein said neoantigen or neoantigen peptide is one that is predicted to be presented by an HLA molecule encoded by an HLA allele which has been determined not to have been lost in a tumour. The neoantigen may be identified according to methods of the present invention. In one embodiment said method comprises the following steps:
 (a) identifying a neo-antigen which is predicted to be presented by an HLA molecule encoded by an HLA allele that has been determined not to have been lost in a tumour; and
 b) producing a composition comprising said neo-antigen or neo-antigen peptide and an antigen presenting cell.

The invention also provides a composition comprising an antigen presenting cell, e.g. a dendritic cell, and a neo-antigen or neo-antigen peptide wherein said neoantigen or neoantigen peptide is one that is predicted to be presented by an HLA molecule encoded by an HLA allele which has been determined not to have been lost in a tumour.

The composition may be produced according to a method as described herein. The composition may also be used in the methods of the invention described herein, for example in methods of producing a T cell or T cell population or composition as discussed herein Compositions as described herein may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

In one aspect, expansion may involve culturing the T cell population with IL-2 or an anti-CD3 and/or an CD28 antibody.

In one aspect of the invention as described herein the T cell population is isolated from the patient to be treated, for example from a tumour sample obtained from said patient.

The T cell population may comprise tumour infiltrating lymphocytes (TILs).

A T cell composition is provided in which said T cell population is enriched with an increased number of T cells which target neo-antigens that are predicted to be presented by an HLA molecule encoded by an HLA allele which has been determined not to have been lost in a tumour compared with the initial T cell population isolated from the subject.

Also provided is a T cell composition useful for the treatment of a cancer in a subject which comprises T cells selectively expanded to target neo-antigens characteristic of the subject's cancer wherein said neoantigens are predicted to be presented by an HLA molecule encoded by an HLA allele which has been determined not to have been lost in a tumour.

A T cell composition as described herein may be enriched with T cells which are specific to neo-antigens that are predicted to be presented by an HLA molecule encoded by an HLA allele which has been determined not to have been lost in a tumour.

In a T cell composition as described herein the expanded population of neo-antigen-reactive T cells may have a higher activity than the population of T cells which have not been expanded, as measured by the response of the T cell population to restimulation with a neo-antigen peptide. Activity may be measured by cytokine production, and wherein a higher activity is a 5-10 fold or greater increase in activity.

A T cell, T cell population or T cell composition as described herein may be obtained or obtainable by any of the methods as described herein.

A T cell, T cell population or T cell composition as described herein may be used in the treatment of cancer.

The invention encompasses a method for treating cancer in a subject comprising administering a T cell composition as described herein to the subject. The invention also encompasses a T cell composition as described herein for use in the manufacture of a medicament for the treatment of cancer.

The method may comprise the following steps:
 (i) isolation of a T cell population from a sample from the subject;
 (ii) expansion of the T cell population which targets a neo-antigen that is predicted to be presented by an HLA molecule encoded by an HLA allele which has been determined not to have been lost in a tumour; and
 (iii) administering the T cell population from (ii) to the subject.

The method may comprise the following steps:
 (i) isolation of a T cell from a sample from the subject;
 (ii) engineering the T cell to express a CAR or TCR which recognises said neo-antigen as described herein to provide a T cell population which targets the neo-antigen; and
 (iii) administering the T cell population from (ii) to the subject.

In one aspect said T cells are selectively expanded using a plurality of neo-antigens, wherein each of said peptides comprises a different mutation. Said plurality may be from 2 to 250, from 3 to 200, from 4 to 150, or from 5 to 100 neo-antigens, for example from 5 to 75 or from 10 to 50 neo-antigens.

A method of the invention may comprise firstly identifying a neoantigen that is predicted to be presented by an HLA molecule encoded by an HLA allele which has been determined not to have been lost in a tumour, and then expanding a T cell population to target the neoantigen.

Thus, in one aspect the invention provides a method for providing a T cell population which targets a neoantigen that is predicted to be presented by an HLA molecule encoded by an HLA allele which has been determined not to have been lost in a tumour, said method comprising the steps of:
 (a) identifying a neoantigen that is predicted to be presented by an HLA molecule encoded by an HLA allele which has been determined not to have been lost in a tumour: and
 (b) expanding a population of T cells to provide a T cell population that targets the neoantigen.

Neoantigens may be determined in a plurality of samples isolated from said tumour.

Following expansion, the resulting T cell population is enriched with an increased number of T cells which target neoantigens that are predicted to be presented by an HLA molecule encoded by an HLA allele which has been determined not to have been lost in a tumour (for example, compared with the sample isolated from the subject).

Thus, in one aspect the invention provides a T cell which recognises a neoantigen that is predicted to be presented by an HLA molecule encoded by an HLA allele which has been determined not to have been lost in a tumour. In a further aspect the invention relates to a population of T cells which recognise a neoantigen that is predicted to be presented by an HLA molecule encoded by an HLA allele which has been determined not to have been lost in a tumour or a population of T cells as described herein.

In a preferred embodiment the invention provides a plurality or population, i.e. more than one, of T cells wherein the plurality of T cells comprises a T cell which recognises a neoantigen that is predicted to be presented by an HLA molecule encoded by an HLA allele which has been determined not to have been lost in a tumour, and a T cell which recognises a different neoantigen that may be presented by an HLA which has been determined not to have been lost in a tumour. As such, the invention provides a plurality of T cells which recognise different neoantigens. Different T cells in the plurality or population may have different TCRs which recognise the same neoantigen.

In a preferred embodiment the number of neoantigens recognised by the plurality of T cells is 2-1000. For example, the number of neoantigens recognised may be 2, 3, 4, 5, 6, 7, 8, 9, 10, 20, 50, 100, 150, 200, 250, 300, 350, 400, 450, 500, 550, 600, 650, 700, 750, 800, 850, 900, 950 or 1000, preferably 2 to 100. There may be a plurality of T cells with different TCRs but which recognise the same neoantigen.

The T cell population may be all or primarily composed of CD8+ T cells, or all or primarily composed of a mixture of CD8+ T cells and CD4+ T cells or all or primarily composed of CD4+ T cells.

In particular embodiments, the T cell population is generated from T cells isolated from a subject with a tumour.

For example, the T cell population may be generated from T cells in a sample isolated from a subject with a tumour. The sample may be a tumour sample, a peripheral blood sample or a sample from other tissues of the subject.

In a particular embodiment the T cell population is generated from a sample from the tumour in which the neo-antigen is identified. In other words, the T cell population is isolated from a sample derived from the tumour of a patient to be treated.

In one embodiment the T cell population comprises tumour infiltrating lymphocytes (TILs).

T cells may be isolated using methods which are well known in the art. For example, T cells may be purified from single cell suspensions generated from samples on the basis of expression of CD3, CD4 or CD8. T cells may be enriched from samples by passage through a Ficoll-paque gradient.

The present invention also provides a method for providing a T cell population which targets a neoantigen in a tumour from a subject which comprises the steps of:
i) isolating a T cell or population of T cells from a sample isolated from the subject; and
ii) expanding the T cell or population of T cells to increase the number or relative proportion of T cells that target neoantigens that are predicted to be presented by an HLA molecule encoded by an HLA allele which has been determined not to have been lost in a tumour.

The T cell population that is produced in accordance with the present invention will have an increased number or proportion of T cells that target one or more neoantigens that are predicted to be presented by an HLA molecule encoded by an HLA allele which has been determined not to have been lost in a tumour. For example, the T cell population of the invention will have an increased number of T cells that target a neoantigen that is predicted to be presented by an HLA molecule encoded by an HLA allele which has been determined not to have been lost in a tumour compared with the T cells in the sample isolated from the subject.

That is to say, the composition of the T cell population will differ from that of a "native" T cell population (i.e. a population that has not undergone the expansion steps discussed herein), in that the percentage or proportion of T cells that target a neoantigen that is predicted to be presented by an HLA molecule encoded by an HLA allele which has been determined not to have been lost in a tumour will be increased. The ratio of T cells in the population that target neoantigens that are predicted to be presented by an HLA molecule encoded by an HLA allele which has been determined not to have been lost in a tumour, to T cells that do not target such neoantigens will be higher in favour of the T cells that target neoantigens that are predicted to be presented by an HLA which has been determined not to have been lost in a tumour.

The T cell population according to the invention may have at least about 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100% T cells that target a neoantigen that is predicted to be presented by an HLA molecule encoded by an HLA allele which has been determined not to have been lost in a tumour. For example, the T cell population may have about 0.2%-5%, 5%-10%, 10-20%, 20-30%, 30-40%, 40-50%, 50-70% or 70-100% T cells that target a neoantigen that is predicted to be presented by an HLA molecule encoded by an HLA allele which has been determined not to have been lost in a tumour. In one aspect the T cell population has at least about 1, 2, 3, 4 or 5% T cells that target a neoantigen that is predicted to be presented by an HLA molecule encoded by an HLA allele which has been determined not to have been lost in a tumour, for example at least about 2% or at least 2% T cells that target a neoantigen that is predicted to be presented by an HLA molecule encoded by an HLA allele which has been determined not to have been lost in a tumour.

Alternatively put, the T cell population may have not more than about 5, 10, 15, 20, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8% T cells that do not target a neo-antigen that may be presented by an HLA molecule encoded by an HLA allele which has been determined not to have been lost in a tumour. For example, the T cell population may have not more than about 95%-99.8%, 90%-95%, 80-90%, 70-80%, 60-70%, 50-60%, 30-50% or 0-30% T cells that do not target a neo-antigen that may be presented by an HLA molecule encoded by an HLA allele which has been determined not to have been lost in a tumour. In one aspect the T cell population has not more than about 99, 98, 97, 96 or 95% T cells that do not target a neo-antigen that is predicted to be presented by an HLA molecule encoded by an HLA allele which has been determined not to have been lost in a tumour, for example not more than about 98% or 95% T cells that do not target a neo-antigen that is predicted to be presented by an HLA molecule encoded by an HLA allele which has been determined not to have been lost in a tumour.

An expanded population neoantigen-reactive T cells may have a higher activity than a population of T cells not expanded, for example, using a neoantigen peptide. Reference to "activity" may represent the response of the T cell population to restimulation with a neoantigen peptide, e.g. a peptide corresponding to the peptide used for expansion, or a mix of neoantigen peptides. Suitable methods for assaying the response are known in the art. For example, cytokine production may be measured (e.g. IL2 or IFNγ production may be measured). The reference to a "higher activity" includes, for example, a 1-5, 5-10, 10-20, 20-50, 50-100, 100-500, 500-1000-fold increase in activity. In one aspect the activity may be more than 1000-fold higher.

The population of T cells may comprise $CD8^+$ T cells, $CD4^+$ T cells or $CD8^+$ and $CD4^+$ T cells.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumour cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated, which prevents autoimmune diseases.

A T cell as described herein may be an engineered T cell.

The neoantigen specific T cell described herein may express a chimeric antigen receptor (CAR) or a T cell receptor (TCR) which specifically binds a neoantigen or a neoantigen peptide, or an affinity-enhanced T cell receptor (TCR) which specifically binds a neoantigen or a neoantigen peptide (as discussed further hereinbelow). For example, the T cell may express a chimeric antigen receptor (CAR) or a T cell receptor (TCR) which specifically binds to a neo-antigen or a neo-antigen peptide (for example an affinity enhanced T cell receptor (TCR) which specifically binds to a neo-antigen or a neo-antigen peptide).

CARs are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules use single-chain variable fragments (scFv) derived from monoclonal antibodies to recognize a target antigen. The scFv is fused via a spacer and a transmembrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Methods for generating TCRs and affinity enhanced TCRs are known in the art. Affinity enhanced TCRs are TCRs with enhanced affinity for a peptide-MHC complex (including e.g. the isolation of TCR genes that encode TCRs from patient samples (e.g. patient peripheral blood or TILs) and the improvement of TCR affinity for a peptide-MHC complex via modification of TCR sequences (e.g. by in vitro mutagenesis and selection of enhanced affinity (or affinity matured) TCRs). Methods of introducing such TCR genes into T cells are known in the art. Methods of identifying optimal-affinity TCRs involving the immunisation of antigen-negative humanised transgenic mice which have a diverse human TCR repertoire (e.g. TCR/MHC humanised mice such as ABabDII mice) with antigen, and isolation of antigen-specific TCRs from such immunised transgenic mice are also known in the art (see e.g. Obenaus M et al., Nat Biotechnol. 33(4):402-7, 2015.

T cells may bear high affinity TCRs, and hence affinity enhancement may not be necessary. High affinity TCRs may be isolated from T cells from a subject and may not require affinity enhancement.

Candidate T cell clones capable of binding a neo-antigen peptide as described herein may be identified using MHC multimers comprising the neo-antigen peptide, for example.

Identified TCRs and/or CARs which specifically target a neo-antigen peptide or neo-antigen may be expressed in autologous T cells from a subject using methods which are known in the art, for example by introducing DNA or RNA coding for the TCR or CAR by one of many means including transduction with a viral vector, transfection with DNA or RNA.

The invention encompasses a T cell as described herein, for example an engineered T cell.

In certain aspects according to the invention as described herein the T cell or T cell population is reinfused into a subject, for example following T cell isolation and expansion as described herein. Suitable methods to achieve this will be known to one skilled in the art. For example, methods for generating, selecting and expanding T cells are known in the art, see e.g. Dudley J Immunother. 2003; 26(4): 332-342, and Rosenberg et al. 2011 Clin Cancer Res:17(13): 4550-7. Methods for reinfusing T cells are described in Dudley et al. Clin Cancer Res. 2010 Dec. 15; 16(24): 6122-6131, and Rooney et al. Blood. 1998 Sep. 1; 92(5): 1549-55. The T cell, T cell population or T cell composition according to the invention can be used in the treatment or prevention of cancer according the invention as described herein.

In one aspect the present invention relates to a method for treating cancer in a subject which comprises administering a T cell or T cell population according to the invention to the subject.

The method may comprise the following steps:

(i) isolation of a T cell-containing sample from the subject;

(ii) expansion of a T cell population which targets an neoantigen as defined herein; and (iii) administering the cells from (ii) to the subject.

In one aspect the T cell may be engineered to express a CAR or affinity-enhanced TCR as described herein.

The invention also provides a method of treating a patient who has cancer comprising administering to said patient a T cell or T cell population as defined herein.

The neoantigen, T cell or T cell population may have been identified or produced according to any of the aspects of the invention as described herein.

The expansion may be ex vivo or in vitro, and may be performed by methods known in the art.

The invention also provides a composition comprising an antigen presenting cell, and a neoantigen or neoantigen peptide as described herein.

In one aspect the antigen presenting cells have been pulsed or loaded with said peptide.

The invention also provides a T cell composition which comprises a population of neo-antigen-specific T cells as described herein, wherein said population of neo-antigen-specific T cells are produced by co-culturing T cells with antigen presenting cells which present neo-antigen peptides.

Compositions as described herein may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

In one aspect the antigen presenting cell is a dendritic cell. In one aspect the antigen presenting cell is irradiated. In one aspect the antigen presenting cell is a cell capable of presenting the relevant peptide, for example in the correct HLA context. Such a cell may be an autologous activated PBMC expressing an autologous HLA molecule, or a nonautologous cell expressing an array of matched HLAs. In one aspect the artificial antigen presenting cell is irradiated.

T cells may also be enriched by initial stimulation of TILs with neoantigens in the presence or absence of exogenous APCs followed by polyclonal stimulation and expansion with cytokines such as IL-2 or with mitogenic antibodies such as anti-CD3 and/or CD28. Such methods are known in the art. For example, see Forget et al. J Immunother. 2014 November-December; 37(9):448-60, Donia et al. Cytotherapy. 2014 August; 16(8):1117-20, Donia et al. Scand J Immunol. 2012 February; 75(2):157-67 and Ye et al. J Transl Med. 2011 Aug. 9; 9:131.

MHC Multimers

Identification of neoantigen-specific T cells in a mixed starting population of T cells may be performed using methods which are known in the art. For example, such T cells may be identified using MHC multimers comprising an neo-antigen peptide as described herein.

MHC multimers are oligomeric forms of MHC molecules, designed to identify and isolate T-cells with high affinity to specific antigens amid a large group of unrelated T-cells. Multimers may be used to display antigens bound to class I MHC, class II MHC, or nonclassical molecules (e.g. CD1d).

The most commonly used MHC multimers are tetramers. These are typically produced by biotinylating soluble MHC monomers, which are typically produced recombinantly in eukaryotic or bacterial cells. These monomers then bind to a backbone, such as streptavidin or avidin, creating a tetravalent structure. These backbones are conjugated with fluorochromes to subsequently isolate bound T-cells via flow cytometry, for example.

The invention provides an MHC multimer comprising an neo-antigen peptide, wherein said neo-antigen may be presented by an HLA which has been determined not to have been lost in a tumour.

MHC multimers according to the invention may be used in methods for identifying, isolating, expanding or otherwise producing a T cell, T cell population or composition as described herein. Neo-antigen peptides may be synthesised using methods which are known in the art.

Composition

The present invention further provides a composition which comprises a neoantigen or peptide, neoantigen specific T cell, or an antibody which recognises an neoantigen, wherein said neo-antigen may be presented by an HLA molecule encoded by an HLA allele which has been determined not to have been lost in a tumour.

Compositions as described herein may be a pharmaceutical composition additionally comprising a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Antibody

In one aspect of the invention an antibody which recognises a neoantigen that is predicted to be presented by an HLA molecule encoded by an HLA allele which has been determined not to have been lost in a tumour is provided.

Once a suitable neoantigen has been identified, for example by a method according to the invention, methods known in the art can be used to generate an antibody.

"Antibody" (Ab) includes monoclonal antibodies, polyclonal antibodies, multispecific antibodies (e.g., bispecific antibodies), and antibody fragments that exhibit the desired biological activity. The term "immunoglobulin" (Ig) may be used interchangeably with "antibody".

An "antibody fragment" comprises a portion of an intact antibody, preferably the antigen binding or variable region of the intact antibody. Examples of antibody fragments include Fab, Fab', F(ab')2, and Fv fragments; linear antibodies; single-chain antibody molecules; and multispecific antibodies formed from antibody fragments.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

The antibody may be a human antibody. A "human antibody" refers to an antibody naturally existing in humans, a functional fragment thereof, or a humanized antibody, i.e., a genetically engineered antibody a portion of which (e.g., Fc region) derives from a naturally-occurring human antibody. A "humanized antibody" is generally considered to be a human antibody that has one or more amino acid residues introduced into it from a source that is non-human. These non-human amino acid residues are often referred to as "import" residues, which are typically taken from an "import" variable domain, by substituting import hypervariable region sequences for the corresponding sequences of a human antibody. Accordingly, such "humanized" antibodies are chimeric antibodies wherein substantially less than an intact human variable domain has been substituted by the corresponding sequence from a non-human species. Furthermore, chimeric antibodies may comprise residues that are not found in the recipient antibody or in the donor antibody. These modifications are made to further refine antibody performance.

In a preferred aspect the antibody is a monoclonal antibody. As used herein, "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. Monoclonal antibodies may be prepared by the hybridoma methodology (Kohler et al., Nature, 256:495 (1975)), or may be made using recombinant DNA methods in bacterial, eukaryotic animal or plant cells. Monoclonal antibodies may also be isolated from phage antibody libraries using the techniques described in Clackson et al., Nature, 352:624-628 (1991) and Marks et al., J. Mol. Biol., 222:581-597 (1991), for example.

Monoclonal antibodies may also be produced by recombinant DNA methods that are known in the art. DNA encoding suitable monoclonal antibodies may be isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the same biological activity.

Antibody fragments may also include insertions, deletions, substitutions, or other selected modifications of particular regions or specific amino acids residues, provided the binding activity of the fragment is not significantly altered or impaired compared to the non-modified antibody or antibody fragment.

These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods will be known to one skilled in the art and can include site-specific mutagenesis of the nucleic acid encoding the antibody fragment.

Antibodies may be humanized antibodies or human antibodies. Humanized forms of non-human (e.g., murine) antibodies are chimeric immunoglobulins, immunoglobulin chains or fragments thereof (such as Fv, Fab, Fab' or other antigen-binding sub-sequences of antibodies) which contain minimal sequence derived from non-human immunoglobulin.

Humanized antibodies include human immunoglobulins (recipient antibody) in which residues from a complementary determining region (CDR) of the recipient antibody are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may comprise at least a portion of an immunoglobulin constant region (Fc), typically that of a human immunoglobulin.

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. As such, "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) may be used to produce a full repertoire of human antibodies in the absence of endogenous immunoglobulin production. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

"Synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

Immunogenic Composition

The present invention provides an immunogenic composition, or vaccine, comprising a neoantigen or neoantigen peptide that may be presented by an HLA which has been determined not to have been lost in a tumour. The immunogenic composition or vaccine may be used in any method of treating or preventing cancer according to the invention. As such, the invention encompasses a method of treating or preventing cancer in a subject comprising administering to the subject an immunogenic composition or vaccine according to the invention.

By "immunogenic composition" is meant a composition that is capable of inducing an immune response in a subject. The immunogenic composition may be a vaccine composition. By "vaccine composition" is meant a composition that is capable of inducing an immune response in a subject that has a therapeutic or prophylactic effect on the condition to be treated.

The immunogenic composition or vaccine may comprise more than one neoantigen or neoantigen peptide.

In one aspect the immunogenic composition or vaccine may comprise more than one different neoantigen or neoantigen peptide, for example 2, 3, 4, 5, 6, 7, 8, 9 or 10 different neoantigens or neoantigen peptides. The neo-antigen may also be in the form of a protein.

In one embodiment the immunogenic composition or vaccine may comprise a polypeptide which comprises an neo-antigen as defined herein. In one embodiment of the invention the immunogenic composition or vaccine may comprise more than one different polypeptide each comprising a neo-antigen, for example 2, 3, 4, 5, 6, 7, 8, 9 or 10 different polypeptides.

The immunogenic composition or vaccine may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion. See, for example, Butterfield, B M J. 2015 22; 350 for a discussion of cancer vaccines.

In particular, the immunogenic composition or vaccine may additionally comprise an adjuvant. Examples of adjuvants include but are not limited to aluminium salts, oil emulsions and bacterial components (e.g. LPS and liposomes). In one embodiment the adjuvant may be poly ICLC, which is a synthetic complex of carboxymethylcellulose, polyinosinic-polycytidylic acid, and poly-L-lysine double-stranded RNA.

Suitable doses of peptides may be determined by one skilled in the art. The dose may depend on the peptide which is to be used. For in vivo use of a peptide an in vivo dose of 0.1-4000 µg, e.g. 0.1-2000 µg, 0.1-1000 µg or 0.1-500 µg, for example 0.1-100 µg, may be employed.

The immunogenic composition or vaccine according to the invention as discussed herein may lead to generation of an immune response in the subject. An "immune response" which may be generated may be humoral and/or cell-mediated immunity, for example the stimulation of antibody production, or the stimulation of cytotoxic or killer cells, which may recognise and destroy (or otherwise eliminate) cells expressing antigens corresponding to the antigens in the vaccine on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8+ T cells and helper CD4+ T Cells. The extent of an immune response may be assessed by markers of an immune response, e.g. secreted molecules such as IL-2 or IFNy or the production of antigen specific T cells.

In addition, a neo-antigen may be delivered in the form of a cell, such as an antigen presenting cell, for example a dendritic cell. The antigen presenting cell such as a dendritic cell may be pulsed or loaded with the neo-antigen or neo-antigen peptide or genetically modified (via DNA or RNA transfer) to express one, two or more neo-antigens or neo-antigen peptides (see e.g. Butterfield 2015 supra; Palucka 2013 supra), for example 2, 3, 4, 5, 6, 7, 8, 9 or 10 neo-antigens or neo-antigen peptides. Methods of preparing dendritic cell immunogenic compositions or vaccines are known in the art.

Alternatively, DNA or RNA encoding one or more neo-antigen, or peptide or protein derived therefrom as defined herein may be used in the immunogenic composition or vaccine, for example by direct injection to a subject. For example, DNA or RNA encoding 2, 3, 4, 5, 6, 7, 8, 9 or 10 neo-antigens, or peptide or protein derived therefrom. The one or more neo-antigen or neo-antigen peptide may be delivered via a bacterial or viral vector containing DNA or RNA sequences which encode one or more neo-antigens or neo-antigen peptides.

Immunogenic compositions or vaccines as described herein may be administered in any suitable way. For example, they may be delivered by any suitable delivery mechanism as known in the art. The composition may involve the use of a vector delivery system, or a vector delivery system may not be necessary. Vectors may be viral or bacterial. Suitable viral vectors may be derived from retroviruses adenoviruses, lentiviruses or pox viruses. Liposomes may be used as a delivery system. *Listeria* vaccines or electroporation may also be used.

Cell-based immunogenic compositions or vaccines may be prepared ex vivo and then administered to the subject.

The invention further provides a cell expressing a neoantigen as defined herein, or a part thereof, on its surface, or a population thereof, which cell is obtainable (or obtained) by any of the methods herein. Such a cell may be used for treating or preventing cancer.

The invention therefore further provides a cell expressing an neo-antigen as defined herein or neo-antigen peptide on its surface (or intracellularly), or a population of such cells, which cell or population is obtainable (or obtained) by methods as defined herein. In a preferred embodiment the cell is an antigen presenting cell such as a dendritic cell.

For in vivo administration of cells as described herein, any mode of administration of the cell population which is common or standard in the art may be used, e.g. injection or infusion, by an appropriate route. In one aspect $1 \times 10^4$ to $1 \times 10^8$ cells are administered per kg of subject (e.g. $1.4 \times 10^4$ to $2.8 \times 10^6$ per kg in human). In one aspect about or not more than $10^7$ cells per kg of subject are administered. Thus, for example, in a human, a dose of $0.1\text{-}20 \times 10^7$ cells per kg of subject may be administered in a dose, i.e. per dose, for example as a dose of T cells or a vaccination dose. In one aspect, between $1 \times 10^4$ to $1 \times 10^5$ cells, between $1 \times 10^5$ to $1 \times 10^6$ cells, between $1 \times 10^6$ to $1 \times 10^7$ cells or between $1 \times 10^7$ to $1 \times 10^8$ cells per kg of subject are administered. For vaccination applications, $1\text{-}20 \times 10^6$ cells per dose may be used. The dose can be repeated at later times if necessary.

The immunogenic composition or vaccine according to the invention may be used in the treatment of cancer.

The invention also provides a method for treating cancer in a subject comprising administering an immunogenic composition or vaccine as described herein to said subject. The method may additionally comprise the step of identifying a subject who has cancer.

In a further aspect the invention provides a method for producing an immunogenic composition or vaccine comprising an neo-antigen peptide or neo-antigen, wherein said neo-antigen may be presented by an HLA molecule encoded by an HLA allele that has been determined not to have been lost in a tumour, said method comprising the steps of:

(a) identifying a neo-antigen that is predicted to be presented by an HLA molecule encoded by an HLA allele that has been determined not to have been lost in a tumour; and (b) producing an immunogenic composition or vaccine with said neo-antigen peptide or neo-antigen protein.

In one aspect of the invention producing the vaccine involves preparing a dendritic cell vaccine, wherein said dendritic cell presents a neoantigen or neoantigen peptide as defined herein.

A neo-antigen protein may also be used in the immunogenic compositions or vaccines and methods relating to vaccination according to the invention.

In a further aspect the invention provides a method for producing an immunogenic composition or vaccine comprising a DNA or RNA molecule encoding a neo-antigen peptide or neo-antigen, said method comprising the steps of:

(a) identifying a neo-antigen that is predicted to be presented by an HLA molecule encoded by an HLA allele that has been determined not to have been lost in a tumour; and (b) producing a DNA or RNA molecule encoding the neo-antigen peptide or neo-antigen; and (c) producing an immunogenic composition or vaccine with said DNA or RNA molecule.

The immunogenic composition or vaccine may be delivered by suitable methods as described hereinbefore.

In one aspect the vaccination is therapeutic vaccination. In this aspect the immunogenic composition or vaccine is administered to a subject who has cancer to treat the cancer.

In a further aspect the vaccination is prophylactic vaccination. In this aspect the immunogenic composition or vaccine is administered to a subject who may be at risk of developing cancer.

In one aspect the immunogenic composition or vaccine is administered to a subject who has previously had cancer and in whom there is a risk of the cancer recurring.

An immunogenic composition or vaccine may also be in the form of DNA or RNA coding for one or several of the neo-antigenic peptides or proteins and delivered by additional methods including but not limited to viral vectors, antigen presenting cells and electroporation.

Subject

In a preferred embodiment of the present invention, the subject is a mammal, preferably a cat, dog, horse, donkey, sheep, pig, goat, cow, mouse, rat, rabbit or guinea pig, but most preferably the subject is a human.

As defined herein "treatment" refers to reducing, alleviating or eliminating one or more symptoms of the disease which is being treated, relative to the symptoms prior to treatment.

"Prevention" (or prophylaxis) refers to delaying or preventing the onset of the symptoms of the disease. Prevention may be absolute (such that no disease occurs) or may be effective only in some individuals or for a limited amount of time.

Cancer

Suitably, the cancer may be ovarian cancer, breast cancer, endometrial cancer, kidney cancer (renal cell), lung cancer (small cell, non-small cell and mesothelioma), brain cancer (gliomas, astrocytomas, glioblastomas), melanoma, merkel cell carcinoma, clear cell renal cell carcinoma (ccRCC), lymphoma, small bowel cancers (duodenal and jejunal), leukemia, pancreatic cancer, hepatobiliary tumours, germ cell cancers, prostate cancer, head and neck cancers, thyroid cancer and sarcomas.

In one aspect the cancer is lung cancer. In one aspect the lung cancer is lung adenocarcinoma. In one aspect the cancer is lung squamous-cell carcinoma.

In one aspect the cancer is melanoma.

In one aspect the cancer may be selected from melanoma, merkel cell carcinoma, renal cancer, non-small cell lung cancer (NSCLC), urothelial carcinoma of the bladder (BLAC) and head and neck squamous cell carcinoma (HNSC) and microsatellite instability (MSI)-high cancers.

In one aspect the cancer may be non-small cell lung cancer (NSCLC).

In one aspect the cancer may be an MSI-high cancer.

In one aspect the cancer may have a mutation in a DNA-repair pathway.

In one embodiment the cancer may have a mutation in a DNA-repair pathway.

In one embodiment the cancer may be an MSI-high cancer.

Treatment using the compositions and methods of the present invention may also encompass targeting circulating tumour cells and/or metastases derived from the tumour.

As discussed herein, metastatic tumour cells may have a different antigenic profile to cells at the primary tumour site. In any of the aspects of the invention as described herein, neoantigens may be targeted that are predicted to be presented by an HLA molecule encoded by an HLA allele which has been determined not to have been lost in a tumour, at both the primary site and one or more metastatic site.

In one aspect different neoantigens may be targeted at the primary site compared with a metastatic site, depending on which neoantigens are predicted to be presented at the primary site and metastatic site. Treatment according to the present invention may encompass treatment of both the primary site and metastatic sites.

Treatment according to the present invention targeting one or more neo-antigens may help prevent the evolution of therapy resistant tumour cells which may occur with standard approaches.

Combination with Other Cancer Treatments

The methods and uses for treating cancer according to the present invention may be performed in combination with additional cancer therapies. In particular, the T cell compositions according to the present invention may be administered in combination with immune checkpoint intervention, co-stimulatory antibodies, chemotherapy and/or radiotherapy, targeted therapy or monoclonal antibody therapy.

Immune checkpoint molecules include both inhibitory and activatory molecules, and interventions may apply to either or both types of molecule. Immune checkpoint inhibitors include, but are not limited to, PD-1 inhibitors, PD-L1 inhibitors, Lag-3 inhibitors, Tim-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR. In a preferred embodiment the checkpoint inhibitor is a CTLA-4 inhibitor.

Examples of suitable immune checkpoint interventions which prevent, reduce or minimize the inhibition of immune cell activity include pembrolizumab, nivolumab, atezolizumab, durvalumab, avelumab, tremelimumab and ipilimumab.

Figure 13:
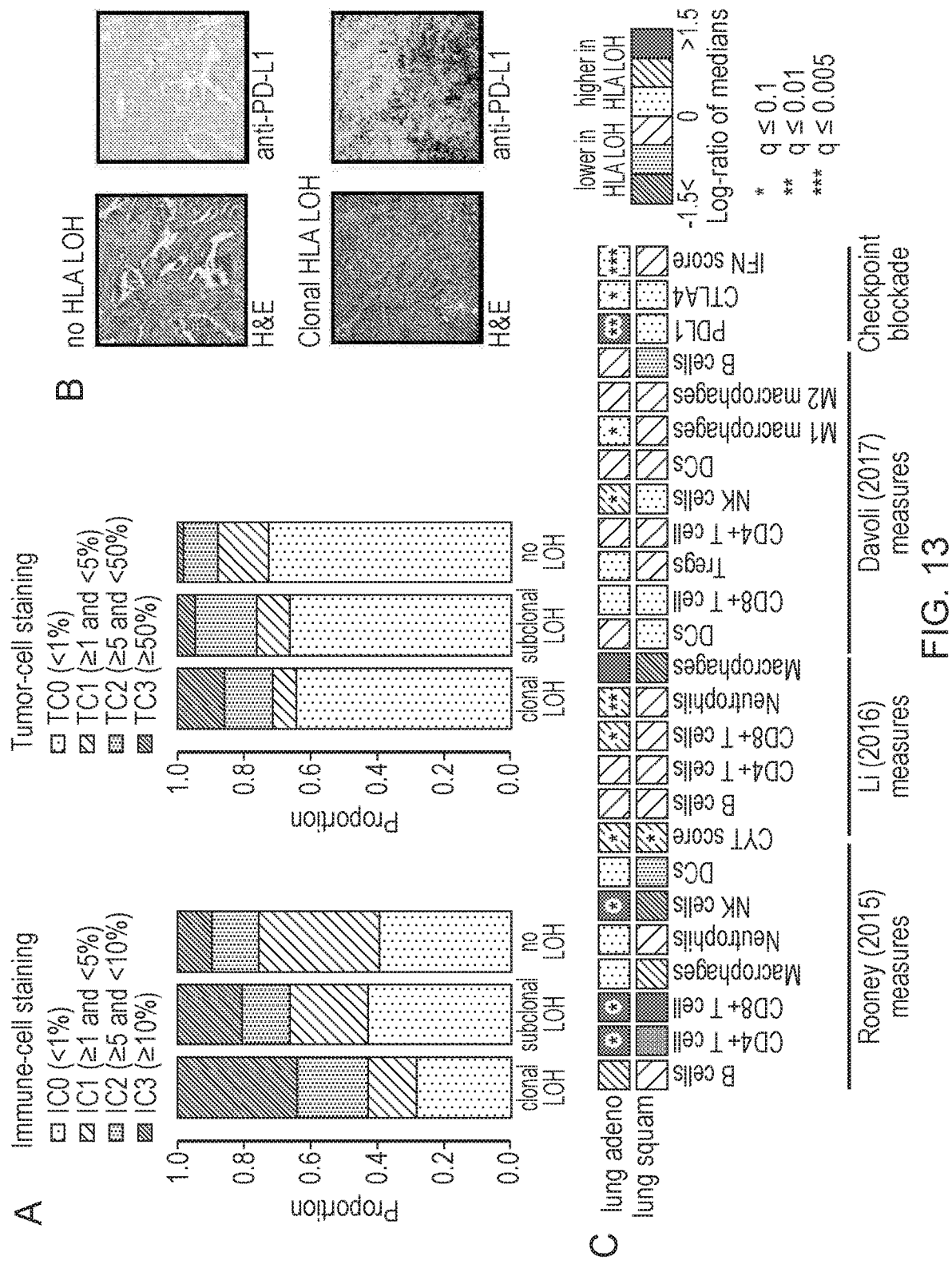
FIG. 13: A) anti-PD-L1 staining on FFPE diagnostic blocks from tumours with clonal HLA LOH, subclonal HLA LOH and no observed HLA LOH. Immune-cell based staining and tumour-cell staining is depicted. (B) Staining from two representative tumours, one without HLA LOH and one with clonal HLA LOH is shown. (C) The log-ratio of medians between tumours containing an HLA LOH event at all loci and those without any HLA LOH event is shown for published immune microenvironment measures and signatures. Increase of an immune measure with HLA LOH is shown in red, and a decrease is shown in blue. FDR (q) values comparing the distribution of immune measures between the HLA LOH groups are indicated by asterisks (*). See also Table S1.

In one aspect the microenvironment of the tumour may show increased immune activation. FIG. 13 shows upregulation of T-cells, NK cells, PDL1 and CLTA4 in the tumour microenvironment.

For example, in one aspect the level of PDL1 may be increased in the tumour microenvironment (see e.g. FIG. 13). As such, in one aspect the methods and uses for treating cancer according to the present invention may be performed in combination with PDL1 intervention, for example with a PD-L1 inhibitor, or a PD-1 inhibitor. In one aspect the methods and uses for treating cancer according to the present invention may be performed in combination with atezolizumab, durvalumab or avelumab. In one aspect the intervention the methods and uses for treating cancer according to the present invention may be performed in combination with pembrolizumab or nivolumab.

In one aspect the level of CTLA-4 may be increased in the tumour microenvironment. As such, in one aspect the methods and uses for treating cancer according to the present invention may be performed in combination with CTLA-4 intervention, for example with CTLA-4 inhibitor. In one aspect the methods and uses for treating cancer according to the present invention may be performed in combination with tremelimumab or ipilimumab.

In one aspect the cancer may be lung adenocarcinoma.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, anthracyclines, epothilones, nitrosoureas, ethylenimines/methylmelamine, alkyl sulfonates, alkylating agents, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin, oxaliplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

'In combination' may refer to administration of the additional therapy before, at the same time as or after administration of the T cell composition according to the present invention.

In addition or as an alternative to the combination with checkpoint blockade, the T cell composition of the present invention may also be genetically modified to render them resistant to immune-checkpoints using gene-editing technologies including but not limited to TALEN and Crispr/Cas. Such methods are known in the art, see e.g. US20140120622. Gene editing technologies may be used to prevent the expression of immune checkpoints expressed by T cells including but not limited to PD-1, Lag-3, Tim-3, TIGIT, BTLA CTLA-4 and combinations of these. The T cell as discussed here may be modified by any of these methods.

The T cell according to the present invention may also be genetically modified to express molecules increasing homing into tumours and or to deliver inflammatory mediators into the tumour microenvironment, including but not limited to cytokines, soluble immune-regulatory receptors and/or ligands.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be described, by way of example only, with reference to the following Examples.

EXAMPLES

Example 1

Method Details

LOHHLA (Loss of Heterozygosity in Human Leukocyte Antigen) Algorithm

As input, LOHHLA requires a tumour and germline BAM, patient-specific HLA calls, predicted by an HLA inference tool (e.g. POLYSOLVER (Shukla, 2015) or Optitype (Szolek 2014)), the HLA fasta file location, purity and ploidy estimates, predicted by a copy number tools (e.g. ASCAT (Van Loo, 2015) or FACETS (Shen, 2016)).

To call HLA LOH, LOHHLA relies upon four computational steps:

Step 1: Extract HLA Reads

Firstly, tumour and germline reads that map to the HLA region of the genome (chr6:29909037-29913661, chr6:31321649-31324964, and chr6:31236526-31239869) as well as chromosome 6 contigs (chr6_cox_hap2, chr6_dbb_hap3, chr6_mann_hap4, chr6_mcf_hap5, chr6_qbl_hap6, chr6_ssto_hap7) are extracted using samtools view. Unpaired mates from this step are removed and the output is converted to FASTQ format.

Step 2: Create HLA Allele Specific BAM Files

For each of the patient's heterozygous HLA alleles, a patient-specific reference fasta is created. The FASTQ files generated in the previous step are used to generate HLA specific BAM files, using mapping parameters that allow for reads to map to multiple HLA alleles, using similar mapping parameters to those previously published (Shukla, 2015). Post-alignment filtering was performed such that reads whose mates mapped to a different allele were discarded, as well as any reads that contained more than one insertion, deletion, or mismatch event compared to the reference HLA allele. For each filtered tumour/germline HLA allele-specific BAM file, coverage was calculated using samtools mpileup.

Step 3: Determine Coverage at Mismatch Positions Between Homologous HLA Alleles

For each HLA locus, a local pairwise alignment was performed between the two homologous HLA alleles using the R Biostrings package. From the pairwise alignment, all of the mismatch positions between the two homologues were extracted. The HLA-specific coverage calculated in Step 2 was used to determine differences in coverage at each of the mismatch positions. An additional file was generated containing the coverage at every mismatch position, counting each read only once, as to avoid over-counting reads that spanned more than one mismatch position.

Step 4: Obtain HLA Specific Log R and BAF

Log R across each HLA gene was obtained by binning the coverage across both homologous alleles at 150 base pair intervals, for both tumour and normal. For each bin, the tumour/normal coverage ratio was multiplied by the multiplication factor, M, corresponding to number of unique mapped reads in the germline, divided by the number of unique mapped reads in the tumour region.

The BAF was calculated at each polymorphic site, and simply reflected the coverage of HLA allele 1 divided by the coverage of HLA allele 1+coverage of HLA allele 2.

Step 5: Determine HLA Haplotype Specific Copy Number

At each polymorphic site, an estimate of the major and minor allele copy number was obtained using the following equations, with the log R value from the corresponding bin in which the polymorphic site was found to reside utilized and the BAF of the polymorphic site.

$$\text{Allele } 1 = \frac{\rho - 1 + BAF \times 2^{\frac{\log R}{\gamma}} \times (2(1-\rho) + \rho \times \varphi)}{\rho}$$

$$\text{Allele } 2 = \frac{\rho - 1 - 2(BAF - 1)^{\frac{\log R}{\gamma}} \times (2(1-\rho) + \rho \times \varphi)}{\rho}$$

where $\rho$=tumour purity; $\gamma$=normalizing constant, 1 for exome sequencing data, see ASCAT for further details; and $\varphi$=tumour ploidy. $\rho$ and $\varphi$ were estimated using ASCAT (van Loo, 2010), as described below.

For each bin, the median Allele 1 and Allele 2 copy number was then determined. To estimate copy number of Allele 1, the median value across bins was calculated. Likewise, to estimate the copy number of Allele 2, the median value across bins was calculated.

A copy number <0.5, was classified as subject to loss. In addition, to avoid over-calling LOH, we calculated a p-value relating to allelic imbalance for each HLA gene. This p-value corresponded to the difference in log R values at mismatch sites between the two HLA homologues, adjusted to count each sequencing read if it spanned more than one mismatch site. Allelic imbalance was determined if P<0.01 using the paired Student's t-Test between the two distributions.

TRACERx 100 Cohort

TRACERx samples considered were obtained from {Jamal-Hanjani, 2017 #11854}. Four patients were excluded due to homozygosity at all three HLA loci or too few mismatch positions between HLA alleles. Lung adenocarcinoma and lung squamous cell carcinoma tumours were considered for downstream analyses. Seven tumours were classified as having a separate histology. Of these one carcinosarcoma showed HLA LOH and three adenosquamous carcinomas, one carcinosarcoma, one large cell carcinoma, and one large cell neuroendocrine tumour did not.

Copy Number Estimation Using ASCAT

ASCAT copy number was estimated as previously described (Jamal-Hanjani, 2017). Given that it was not possible to directly infer the copy number of the HLA alleles using ASCAT, the segment overlapping the HLA locus was used, or alternatively, the closest segment.

TRACERx Mutation Data

TRACERx mutation tables were obtained from (Jamal-Hanjani, 2017).

Comparison of ASCAT and LOHHLA

In order to compare ASCAT and LOHHLA we treated each tumour region as a separate sample, and ran it through the LOHHLA pipeline with default settings.

To assess the predicting copy number state for the HLA locus, we determined the copy number state of the genomic segment overlapping with the HLA locus. If no genomic segment was found to overlap with the HLA locus, the closest segment was selected.

To compare our allelic imbalance estimates, we considered a tumour region to be concordant if ASCAT predicted allelic imbalance across the locus and at least one HLA gene using LOHHLA was found to harbor allelic imbalance. Likewise, for LOH, we considered ASCAT and LOHHLA estimates to be concordant if ASCAT predicted a minor allele of 0 and this was also predicted for at least one HLA gene.

Conversely, allelic imbalance estimates were classified as discordant if allelic imbalance was predicted in any HLA gene using LOHHA and not with ASCAT. Similarly, for LOH was classified as discordant if any HLA gene using LOHHLA was classified as exhibiting a minor allele of 0 and no LOH was identified using ASCAT.

Fragment Analysis Validation of LOHHLA Results

Allelic imbalance was validated using four polymorphic Sequence-Tagged Site (STR) markers located on the short arm of chromosome 6, close to the HLA locus—(D6S2852, D6S2872, D6S248 and D6S1022). 20 ng of patient germline and tumour region DNA was amplified using the PCR. The PCR comprised of 35 cycles of denaturing at 95 C for 45 seconds, followed by an annealing temperature of 55 C for 45 seconds and then a PCR extension at 720 C for 45 seconds. PCR products were separated on the ABI 3730xl DNA analyzer. Fragment length and area under the curve of each allele was determined using the Applied Biosystems software GeneMapper v5. When two separate alleles were identified for a particular marker, the fragments could be analyzed for allelic imbalance using the formula (At/Bt)/(An/Bn). The output of this formula was defined as the normalized allelic ratio.

HLA Type, HLA Mutations, and Predicted Neo-Antigen Binders

The 4-digit HLA type for each sample was inferred using POLYSOLVER (POLYmorphic loci reSOLVER), which uses a normal tissue BAM file as input and employs a Bayesian classifier to determine genotype (Shukla, 2015). HLA mutations in each tumour region were also assessed using POLYSOLVER.

Novel 9-11mer peptides that could arise from identified non-silent mutations present in the sample (Jamal-Hanjani, 2017) were determined. The predicted IC50 binding affinities and rank percentage scores, representing the rank of the predicted affinity compared to a set of 400,000 random natural peptides, were calculated for all peptides binding to each of the patient's HLA alleles using netMHCpan-2.8 and netMHC-4.0 (Andreatta 2016; Nielsen 2003; Hoof 2009; Nielsen 2009). Putative neoantigen binders were those peptides with a predicted binding affinity <500 nM or rank percentage score <2%.

Mapping HLA LOH to Phylogenetic Trees and Identification of Parallel Evolution

LOH events detected in every tumour region tested were considered to be clonal events and mapped to the trunk of the phylogenetic tree. For heterogeneous LOH events, the regional copy number of the HLA allele lost was used in conjunction with the patient tree structure and subclone cancer cell fractions in a quadratic programming approach, using the R package quadprog, to determine the best placement of the LOH event.

This was achieved by solving a quadratic programming equation:

$$\min(-d^{\wedge}Tb+\tfrac{1}{2}b^{\wedge}TDb)$$

with the constraints:

$$A^{\wedge}Tb{>}{=}b\text{vec}$$

The LOH event was tested at each branch. For each possibility, the phylogenetic tree was broken into two, one containing all clones after the LOH event and the other consisting of the remainder of the tree. A 2×n matrix, where n is the number of regions sampled, was constructed containing the regional sum of the cancer cell fractions for each subclone in the subtree and the regional sum of cancer cell fractions from subclones in the remaining tree. The regional cancer cell fraction matrix was multiplied by the transpose of itself to generate a 2×2 matrix for input (Dmat) into the quadprog function, solve·QP. The vector to be minimized (dvec) was obtained by multiplying the LOHHLA calculated HLA allele copy number for each region by the transpose of the regional cancer cell fraction matrix. Finally, the solve·QP function was called with Dmat and dvec, using a constraint matrix, Amat, such that all results had to be positive and a constraint vector, bvec, such that the estimated copy number of HLA allele for the remaining tree was at least 0.5. The errors between observed and predicted copy number values from placing LOH event on each branch were output and the solution providing the least error was selected.

Each mapped event was inspected and events that did not fit the phylogenetic tree or had large error values, either indicating the presence of an additional subclone or multiple independent HLA LOH events, were manually adjusted.

Assessing Significance of Focal and Arm-Level LOH

In order to assess whether HLA LOH occurred more than expected by chance, we considered whether each LOH event was focal or arm-level in nature. In brief, to classify LOH as arm-level or focal, we focused on the minor allele frequency across the genome. First, any segments (as predicted by ASCAT) with identical minor allele copy numbers were merged. Subsequently, segments that spanned >=75% the length of a given chromosome arm, were classified as 'arm-level', while segments that were <75% were considered focal.

To assess the significance of focal events, for each tumour, the proportion of the genome subject to focal minor allele loss was determined. This value was assumed to reflect the probability for focal minor allele loss in each tumour. Based on this probability, we generated an aberration state (loss or no loss) for each sample separately and determined the proportion of samples exhibiting loss. We repeated this process 10,000 times to obtain a background distribution reflecting the likelihood of observing losses given the probability of loss in each sample. A p-value reflecting the likelihood of observing the level of minor allele loss seen at the HLA locus was determined by counting the percentage of simulations showing a higher proportion loss than that observed.

The same procedure was conducted for arm-level events, using the observed frequency of arm-level allele specific loss in each tumour.

Mutational Signature Analysis

Mutational signatures were estimated using the deconstructSigs R package as previously described (Jamal-Hanjani, 2017).

Assessing Whether Neoantigens Preferentially Bind to Loss HLA Alleles

To assess whether neoantigens preferentially bind to lost HLA alleles, we focused on tumours exhibiting 6 distinct HLA alleles (i.e. no homozygosity for any allele in the germline) and loss of one HLA haplotype (3 parental alleles) in at least one tumour region.

Neoantigens (as defined above), were ranked according to IC50 binding scores. Duplicate mutations were removed to ensure each neoantigen reflected the highest binding score (lowest IC50 value) for any given mutation. We further filtered the mutation list to only include subclonal mutations (defined as previously described (Jamal-Hanjani, 2017)) occurring in the tumour regions harboring loss events (>5% VAF). The number of subclonal neoantigens binding to each haplotype was then determined for each tumour. A paired wilcoxon test was used to compare the number of subclonal neoantigens binding to the lost haplotype compared to the kept haplotype.

PD-L1 Immunohistochemistry

Formalin-fixed, paraffin-embedded (FFPE) tissue sections of 4-um thickness were stained for PD-L1 with an anti-human PD-L1 rabbit monoclonal antibody (clone SP142; Ventana, Tucson, Ariz.) on an automated staining platform (Benchmark; Ventana) with the OptiView DAB IHC Detection Kit and the OptiView Amplification Kit (Ventana Medical Systems Inc.) in a GCP-compliant central laboratory (Targos Molecular Pathology GmbH). PD-L1 expression was evaluated on tumour cells and tumour-infiltrating immune cells. For tumour cells the proportion of PD-L1-positive cells was estimated as the percentage of total tumour cells. For tumour-infiltrating immune cells, the percentage of PD-L1-positive tumour-infiltrating immune cells occupying the tumour was recorded. Scoring was performed by a trained histopathologist [according to previously published scoring criteria (Herbst, 2014)].

RNA-Seq Expression Analysis Using TCGA

RNA-sequencing data was downloaded from the TCGA data portal. For each LUAD and LUSC sample, all available 'Level_3' gene-level data was obtained. The raw read counts were used as input into the R package DESeq2 for analysis.

An FDR cutoff of 0.05 was used to determine genes significantly differentially expressed.

Quantification and Statistical Analysis

All analysis was performed in the R statistical environment version >=3.2.1. All statistical tests were two-sided unless expressly stated and statistical significance was determined if P value was less than 0.05, unless otherwise stated. Comparisons were made using the Fisher's exact test FIG. 2B, as described above for FIG. 3, unpaired Wilcoxon test for FIG. 4A-C, and paired Wilcoxon test for FIG. 4D-E.

Data and Software Availability

The TRACERx 100 cohort comprises the first 100 patients prospectively analysed by the lung TRACERx study (https://clinicaltrials.gov/ct2/show/NCT01888601, approved by an independent Research Ethics Committee, 13/LO/1546) and mirrors the prospective 100 patient cohort described in (Jamal-Hanjani, 2017).

Sequence data is available at the European Genome-phenome Archive (EGA), which is hosted by the The European Bioinformatics Institute (EBI) and the Centre for Genomic Regulation (CRG), under accession numbers EGAS00001002247 (primary tumour data).

Further information about EGA can be found at https://ega-archive.org (the European Genome-phenome Archive of human data consented for biomedical research).

TCGA tumour and matched germline exome sequencing BAM files for both lung adenocarcinoma (LUAD, n=397) and lung squamous cell carcinoma (LUSC, n=350), were obtained from the Cancer Genome Atlas (TCGA, http://cancergenome.nih.gov/) via https://cghub.ucsc.edu. The data was processed as previously described (Jamal Hanjani, 2017).

Results

Inferences of HLA LOH and Imbalance in Tumour Samples Using LOHHLA

In order to determine allele specific copy number, the majority of copy number tools rely on the relative coverage and variant allele frequency of single nucleotide polymorphisms (SNPs) in the tumour and matched normal across the genome or exome (Van Loo; Shen, 2016; Carter, 2012). However, inferring copy number status at the HLA locus is problematic due to poor coverage and the polymorphic nature of the region. SNPs cannot readily be identified at the HLA locus using sequencing data that has been aligned to the human reference genome as reads that are highly polymorphic will not align and will therefore be discarded. Indeed, despite being one of the most polymorphic regions of the human genome, an average of less than 1 (mean 0.84, range 0-7) informative heterozygous SNP in the three HLA class I genes was identified in 97 patients from the TRACERx cohort (Jamal-Hanjani, 2017) using the state-of-the-art SNP caller Platypus (Rimmer, 2014). These data suggest that conventional copy number calling algorithms are not suited to directly infer haplotype specific copy number of the HLA locus.

We reasoned that, by leveraging the reads that map specifically to an individual's germline HLA alleles rather than the human reference genome, it would be possible to accurately determine HLA haplotype specific copy number. To achieve this, we developed LOHHLA (FIG. 1A). Implementation of LOHHLA relies upon five steps. Firstly, tumour and germline reads that map to the HLA region of the genome and chromosome 6, including contigs, are extracted. Secondly, tumour and germline HLA allele specific .bam files are generated by aligning reads to patient-specific HLA alleles (obtained from HLA serotyping or an inference tool, e.g. Polysolver (Shukla, 2015) or Optitype (Szolek)). Thirdly, polymorphic sites between homologous HLA alleles are identified. Fourth, tumour coverage relative to germline (log R) and b-allele frequencies (BAF) are inferred at each HLA locus, making use of identified polymorphic sites. Finally, HLA allele specific copy number, accounting for tumour purity and ploidy (obtained from a copy number caller e.g. ASCAT (Van Loo, 2010) or FACETs (Shen, 2016) is determined for each HLA gene.

To the best of our knowledge, no other method currently exists to infer haplotype specific copy number of the HLA locus, and as such, there is no gold-standard method with which we can compare LOHHLA copy number estimation or inference of which HLA haplotype is subject to loss.

Figure 2:
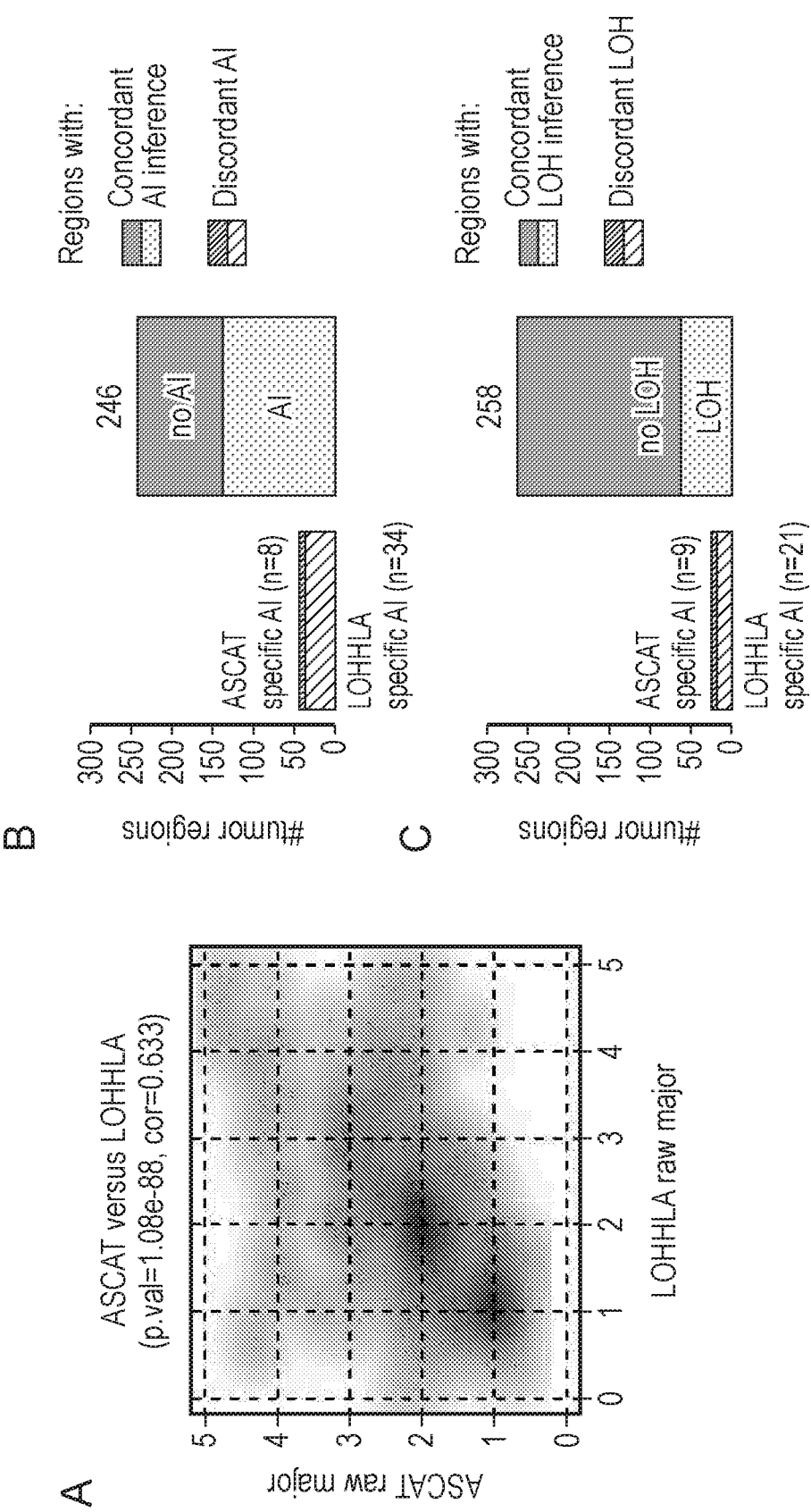
FIG. 2: Comparison of LOHHLA and ASCAT, related to FIG. 1. A) Plot illustrating comparison of ASCAT major copy number and LOHHLA major copy number. B-C) Summary of concordant and discordant tumour regions in terms of allelic imbalance (B) and LOH (C). D) Schematic illustrating how ASCAT cannot directly infer HLA copy number or which HLA allele is subject to loss. By contrast, LOHHLA uses SNPs covering HLA genes to directly infer HLA copy number.
Figure 2:
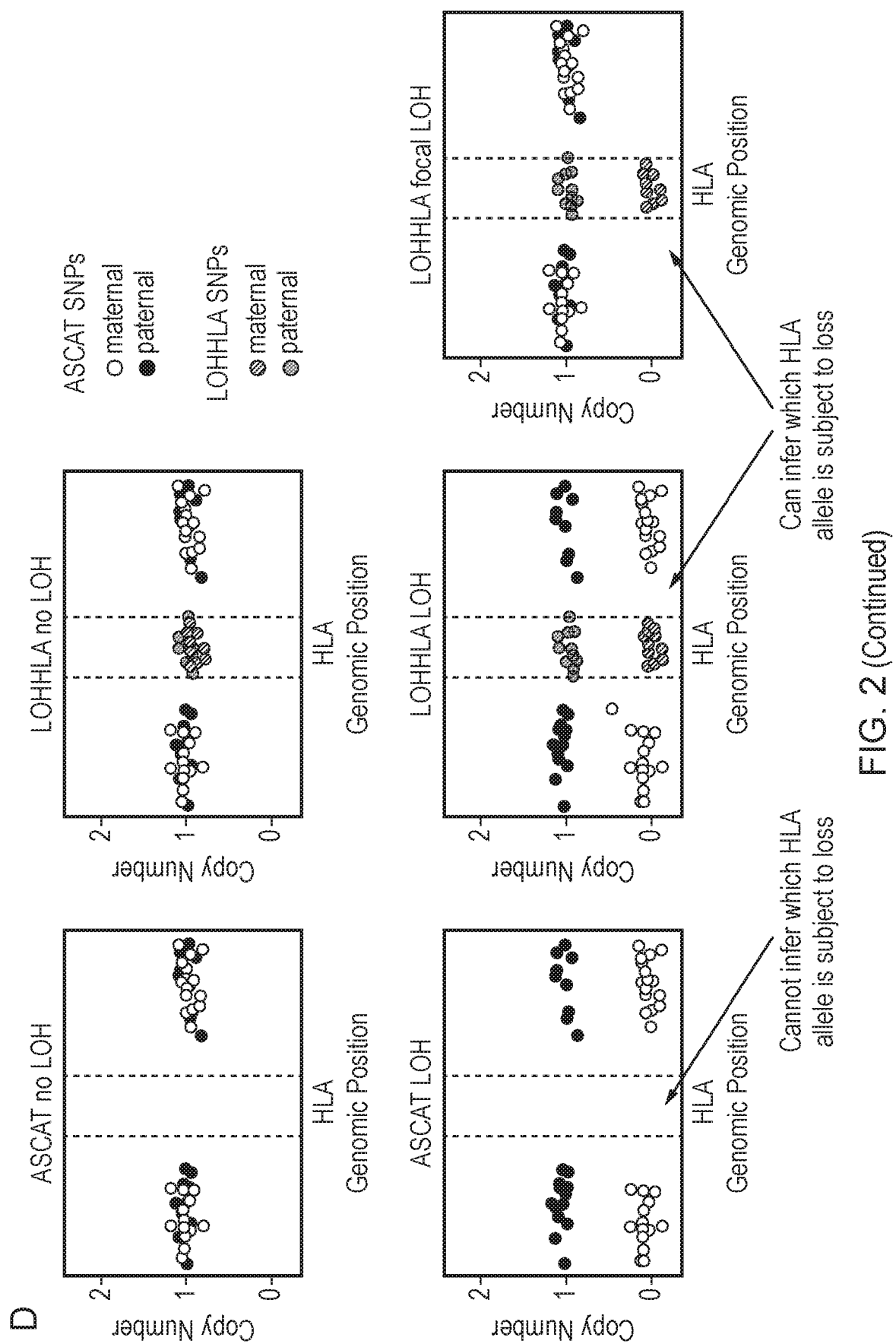

Therefore, to test the accuracy of HLA copy number estimation, we made the assumption that genomic segments adjacent to the HLA locus will often exhibit the same copy number profile as the HLA locus itself, which holds for cases without a highly focal HLA event (FIG. 2D). We used ASCAT (Van Loo, 2010) to estimate the frequency of allelic imbalance and LOH in the genomic regions surrounding the HLA locus in 303 TRACERx NSCLC exomes from 97 patients (Jamal-Hanjani, 2017) and compared these to LOHHLA copy number estimation. Notably, given that ASCAT is not designed to infer which HLA haplotype is subject to loss or imbalance, for this analysis, we could only compare whether ASCAT and LOHHLA exhibited concordant copy number profiles not whether concordant haplotypes were predicted to be lost.

Figure 10:
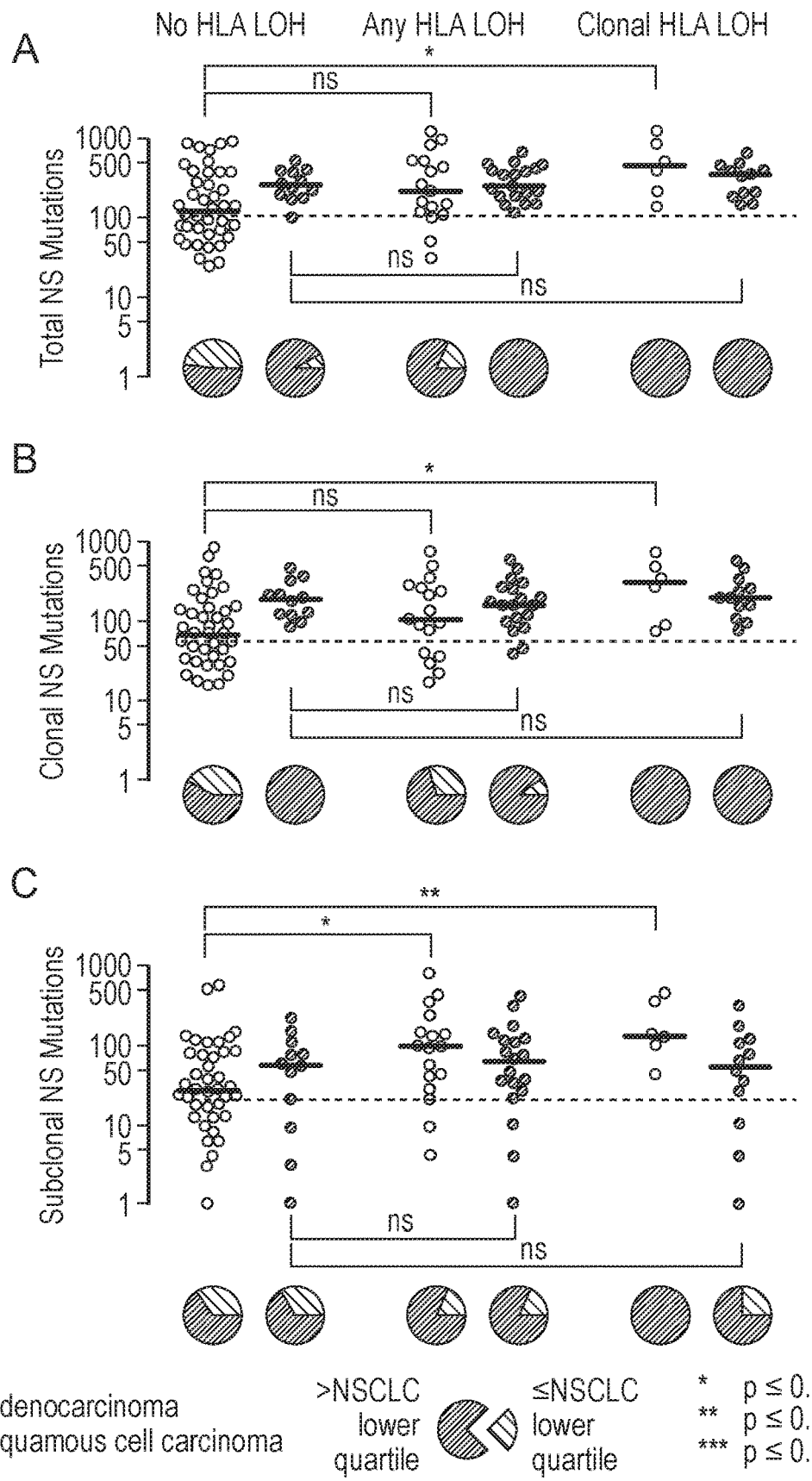
FIG. 10: Non-synonymous Mutational Burden Associates with HLA LOH and Neoantigens More Frequently Bind the Lost Allele. (A) The total number of nonsynonymous mutations is plotted across different categories of HLA LOH for lung adenocarcinoma (light blue) and lung squamous cell carcinomas (magenta). Tumours could either be classified as having no HLA LOH, any HLA LOH event, without taking into account the timing of the event, subclonal HLA LOH, or clonal HLA LOH. The lowest total non-synonymous mutation quartile is indicated by the dashed red line and the proportion of tumours with a total non-synonymous mutational burden greater or less than that is indicated by the pie charts for each HLA LOH classification group. (B) The number of clonal non-synonymous mutations is plotted across different categories of HLA LOH for lung adenocarcinoma (light blue) and lung squamous cell carcinomas (magenta). The lowest clonal non-synonymous mutation quartile is indicated by the dashed red line and the proportion of tumours with a clonal non-synonymous mutational burden greater or less than that is indicated by the pie charts for each HLA LOH classification group. (C) The number of subclonal non-synonymous mutations is plotted across different categories of HLA LOH for lung adenocarcinoma (light blue) and lung squamous cell carcinomas (magenta). The lowest subclonal non-synonymous mutation quartile is indicated by the dashed red line and the proportion of tumours with a subclonal non-synonymous mutational burden greater or less than that is indicated by the pie charts for each HLA LOH classification group. (D) The number of non-synonymous mutations found in the clone harbouring the HLA LOH event compared to the number of non-synonymous mutations in the clone from the alternative branch without HLA LOH. (E) The number of subclonal neoantigens predicted to bind to either the lost HLA allele or the kept HLA allele is indicated for all NSCLC tumours exhibiting HLA LOH, all lung adenocarcinoma tumours with HLA LOH, and all lung squamous tumours with HLA LOH. The p-value is calculated using a paired wilcoxon test. (F) The total number of mutations predicted to result in a binder to the lost allele is shown for all patients with at least one HLA LOH event. The mutation clonality is also indicated as either clonal (light blue) or subclonal (light red).
Figure 10:
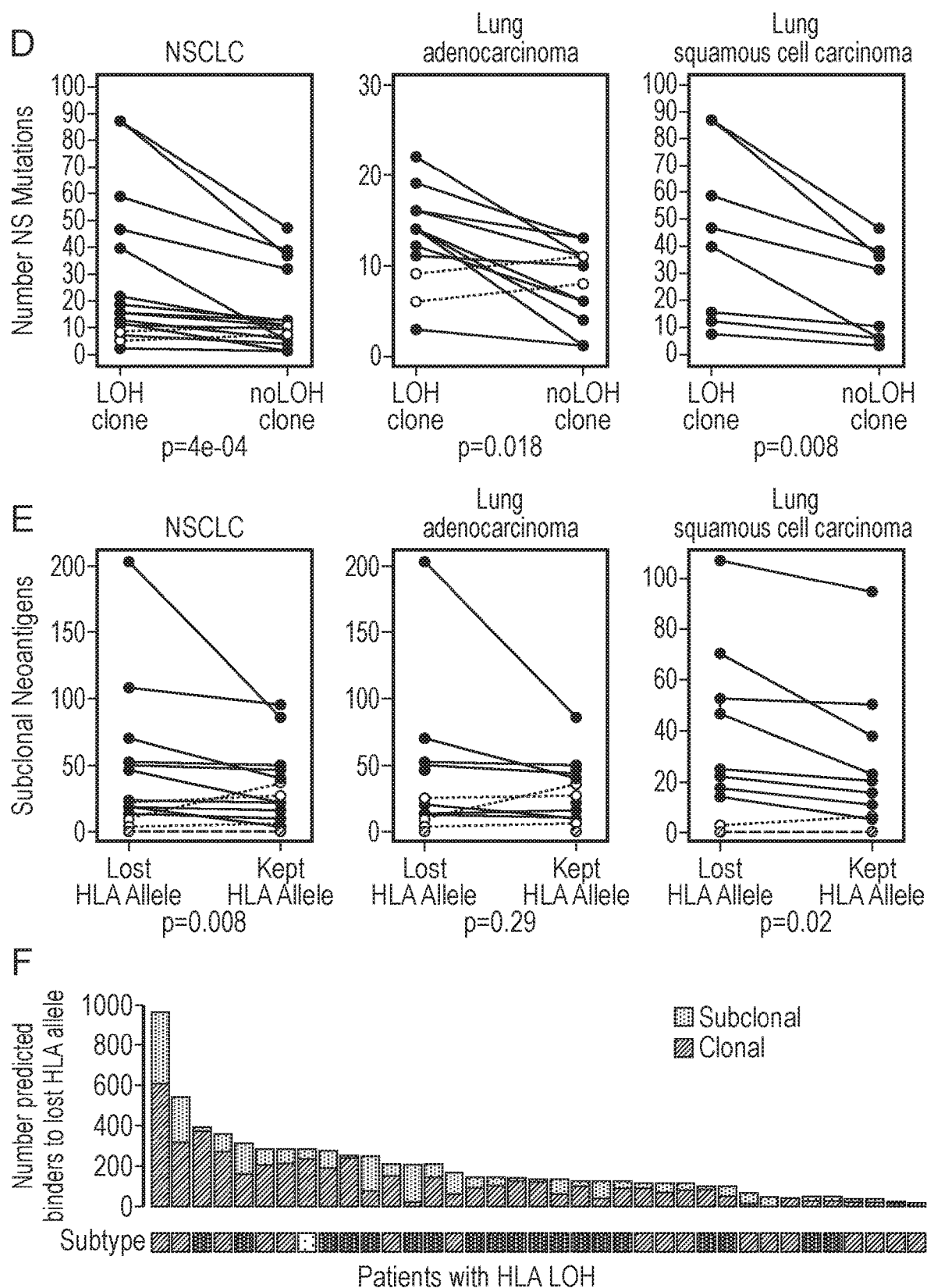

We observed a highly significant relationship between the minor and major allele copy number estimates obtained from LOHHLA and ASCAT ($P<0.001$, rho=0.70, Spearman's rank test, FIG. 1B, FIG. 2A), supporting the utility of LOHHLA to accurately estimate copy number and LOH. We found concordant allelic imbalance estimates in 246/288 tumour regions (FIG. 10 and FIG. 2B-C). Thirty four additional of allelic imbalance in tumour regions were uncovered using LOHHLA while only 8 tumour regions exhibited evidence of allelic imbalance using ASCAT and not LOHHLA. In many cases, the discrepancies between ASCAT and LOHHLA could be explained by the fact that, as discussed, ASCAT cannot directly infer haplotype specific copy number at the HLA locus and thus the copy number of either the 5' or 3' adjacent segment is erroneously assumed to cover the HLA locus (FIG. 2D).

Concordant LOH inference was observed in 264/288 tumour regions, with additional LOH defined by LOHHLA identified in 21 tumour regions, while only 9 tumour regions were identified as harboring a lost haplotype by ASCAT and not LOHHLA (FIG. 1D and FIG. 2C).

Figure 3:
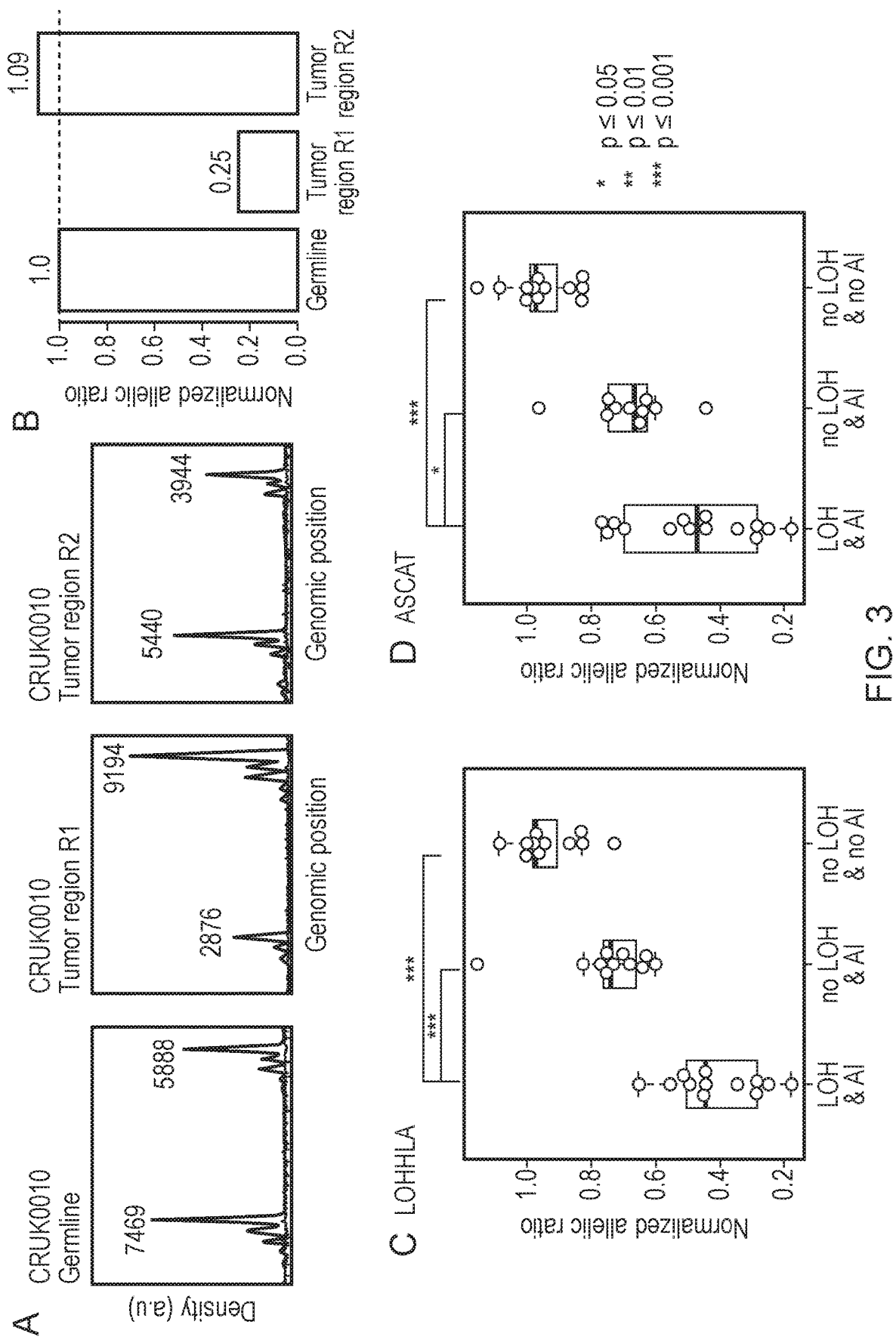
FIG. 3: Validation of LOHHLA using fragment analysis, related to FIG. 1. A) Area under the curve of each allele using the Applied Biosystems software GeneMapper v5 for germline and tumour regions R1 and R2 in CRUK0010. B) Normalized allelic ratio determined using the formula (At/Bt)/(An/Bn). Notably, region R1 shows clear evidence of allelic imbalance and likely LOH, while region R2 appears similar to germline. C) Normalized allelic ratio for tumour regions showing either LOH and allelic imbalance; no LOH but allelic imbalance; or no LOH or allelic imbalance classified by LOHHLA. Notably, the outlier tumour with a high normalized allelic ratio has been classified as exhibiting mirrored subclonal allelic imbalance by LOHHLA. D) Normalized allelic ratio for tumour regions showing either LOH and allelic imbalance; no LOH but allelic imbalance; or no LOH or allelic imbalance classified by ASCAT. Normalized allelic ratio for tumour regions showing either LOH and allelic imbalance; no LOH but allelic imbalance; or no LOH or allelic imbalance classified by TITAN (E and G) and Sequenza (F and H), P-values correspond to Wilcoxon rank sum test.
Figure 3:
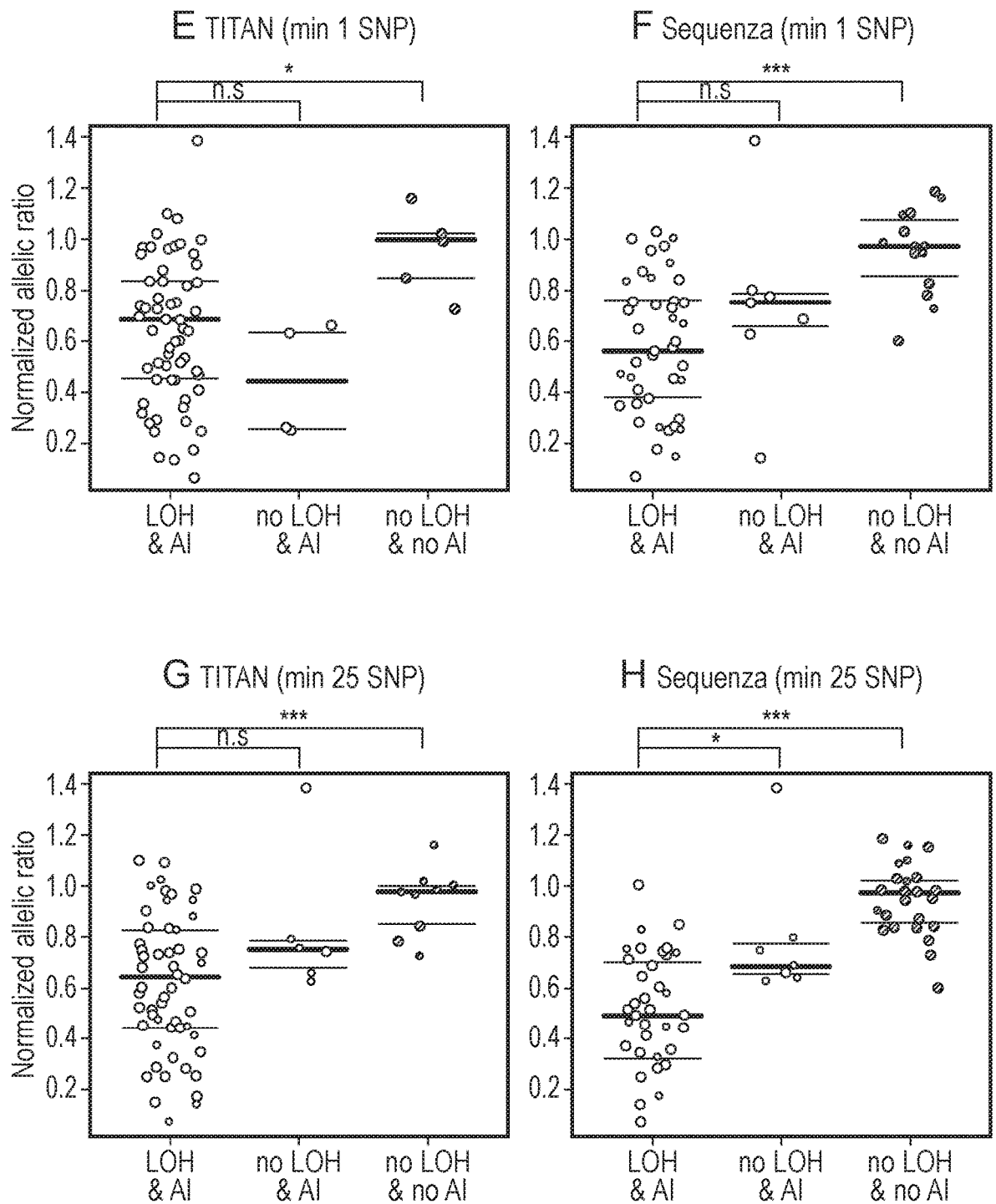

To further validate our approach, we performed fragment analysis of highly polymorphic stretches of DNA in close proximity to the HLA locus in 82 tumour regions from 27 tumours (FIG. 3). Tumour regions analyzed were either predicted to have all loci (HLA-A, HLA-B and HLA-C) subject to LOH, or no loci affected. Supporting the utility of LOHHLA to accurately classify LOH, we observed significant differences in normalized allelic ratio between tumours classified as exhibiting either LOH, allelic imbalance without LOH, or no observable imbalance ($p=1.07e-19$ [LOH versus no imbalance], $p=4.57e-05$ [LOH versus allelic imbalance], FIG. 3). Furthermore, the distinction between these three categories was clearer using LOHHLA than the copy number tools ASCAT (Van Loo, 2010), Sequenza (Favero, 2015) or TITAN (Ha, 2014)

Taken together, these data suggest that LOHHLA is able to accurately infer both allelic imbalance and LOH in tumour samples. While it may be possible to infer whether the HLA locus is subject to allelic imbalance and/or LOH in the majority of cases using copy number tools such as ASCAT (Van Loo), LOHHLA provides additional sensitivity and specificity to detect these aberrations, even if they are highly focal. Crucially, LOHHLA also infers specifically which HLA allele homologue is subject to loss at each of the three HLA genes, which, to the best of our knowledge, is currently not possible with any other tool.

Prevalence and Timing of HLA Imbalance and Loss Across NSCLC

Figure 4:
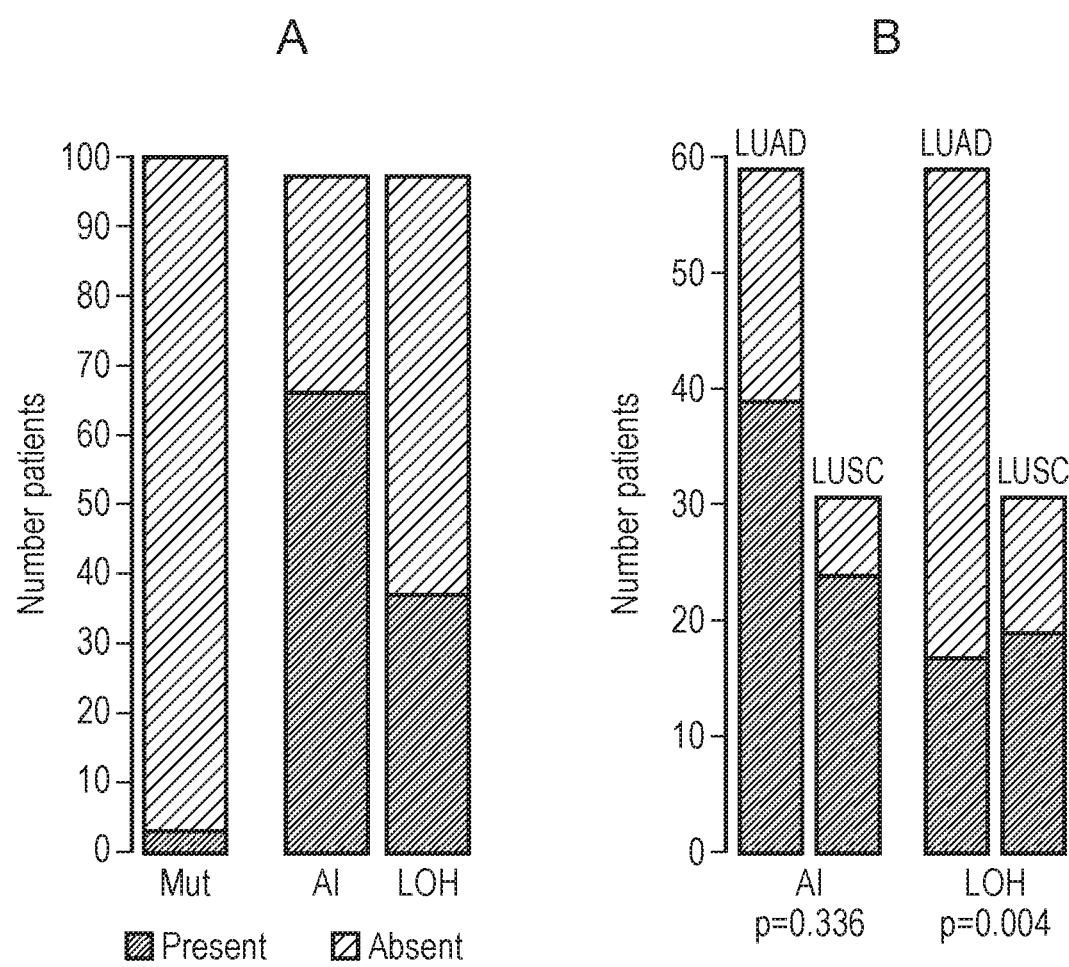
FIG. 4: Frequency and Timing of HLA LOH in NSCLC (A) The total number of TRACERx patients exhibiting an HLA non-synonymous mutation, HLA allelic imbalance, or LOH at the HLA locus is shown. (B) Proportion of HLA allelic imbalance and HLA LOH identified in NSCLC by sub-type. Enrichment significance was tested using a Fisher's Exact Test.

HLA mutations, which have the ability to disrupt neoantigen-MHC binding, have been previously described in many cancer types, including NSCLC (Shukla, 2015). However, despite being linked to cancer and immune escape, mutations in HLA genes are infrequently detected (Lawrence, 2014; Shukla, 2015). In our cohort of 100 TRACERx patients, only tumours from three patients harbored nonsynonymous mutations in HLA genes using Polysolver (Shukla, 2015) (FIG. 4). One lung adenocarcinoma tumour had also acquired a mutation in β-2 microglobulin (B2m), which is vital for MHC class I expression and peptide binding stability. No further mutations predicted to disrupt antigen presentation or the MHC class I complex were identified in this cohort. Likewise, a broader study of 174 lung squamous cell and 223 lung adenocarcinoma patients from TCGA only classified 8% and 5% of tumours as harboring HLA mutations, respectively (Shukla, 2015).

In 19/32 (61%) of lung squamous cell carcinomas and 17/59 (29%) of lung adenocarcinomas, LOHHLA identified HLA LOH, where either one maternal or paternal HLA allele was lost, resulting in HLA homozygosity. Just as HLA mutations occur more frequently in lung squamous cell carcinomas (Shukla, 2015), we also observed an enrichment for HLA LOH in lung squamous cell carcinomas as compared to lung adenocarcinomas (p=0.004) (FIG. 4A-B). The increased frequency with which HLA LOH occurs and the possibility of previously antigenic peptides no longer being presented on the lost allele suggests that HLA LOH has the capacity to be a more prevalent mechanism of immune disruption than HLA or B2M mutations.

Figure 5:
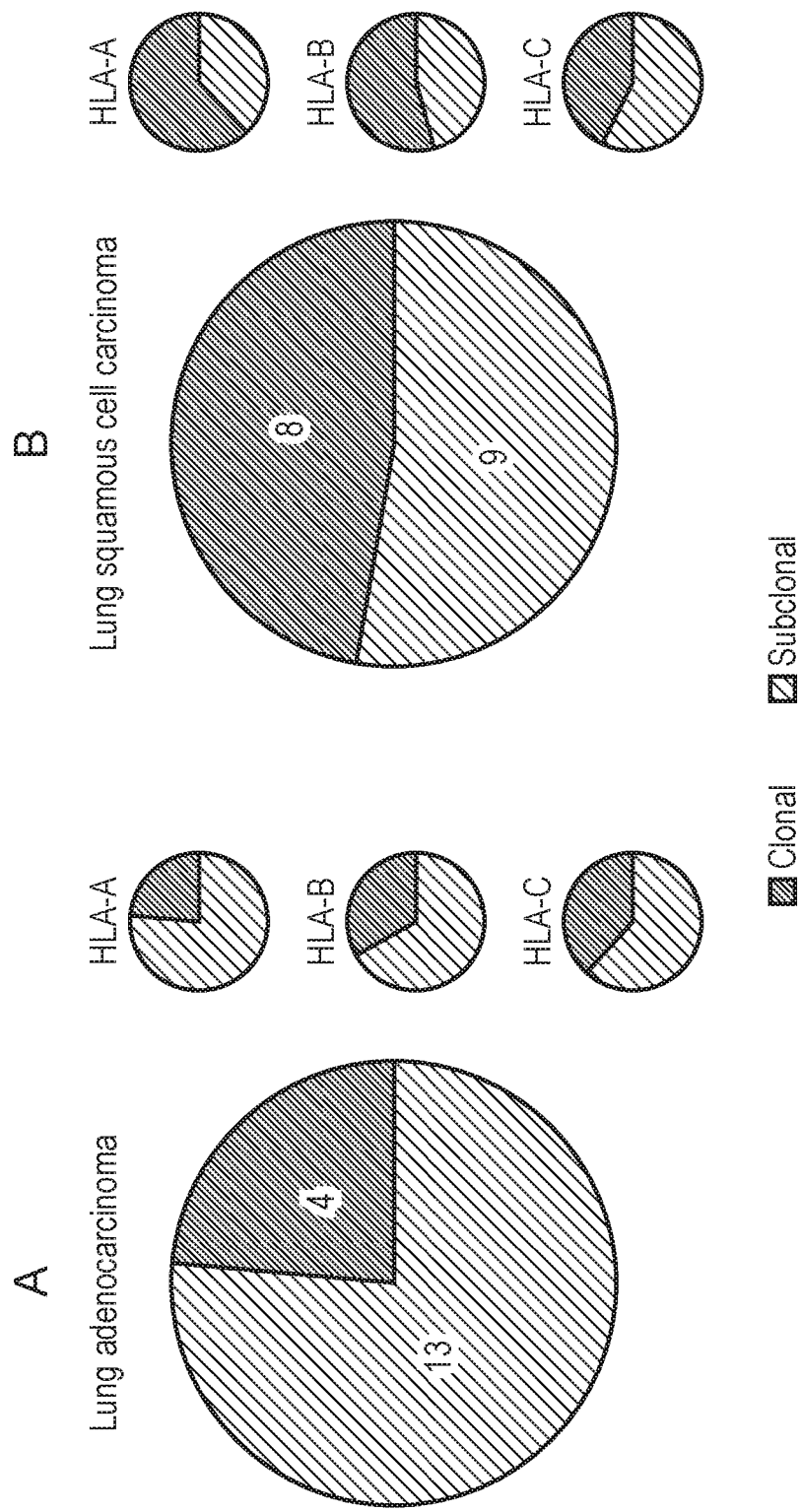
FIG. 5: Frequency and Timing of HLA LOH in NSCLC (A-B) Pie charts show the timing of HLA LOH events using multi-region information for lung adenocarcinoma (A) lung squamous cell carcinomas (B). Events at individual HLA A/B/C loci were considered clonal if they were found in every region considered and subclonal if they were found in only a subset of tumour regions. A patient sample was considered to have clonal HLA LOH if all of the individual loci lost in that patient occurred clonally. Two lung squamous cell carcinoma patients with only a single region available for copy number analysis are not shown.

To investigate whether HLA allele specific loss was an early event in the tumour's evolution present clonally in every cancer cell, or whether it was present subclonally, in only a subset of cancer cells, indicating an occurrence later in evolution and potentially in response to a shift in the equilibrium between immune recognition and evasion, we utilized the high-depth and multi-region nature of the TRACERx dataset. HLA LOH appeared to frequently occur subclonally in both histological subtypes, with 13/17 lung adenocarcinoma and 9/17 lung squamous cell carcinomas exhibiting loss of an HLA allele in a subset of cancer cells (FIG. 5A-B). Phylogenetic analysis permitted us to map HLA LOH events to probable subclones from the tumour's evolutionary tree (FIG. 6-7) (Jamal-Hanjani, 2017) These data suggest the selective pressure from the immune system may increase as the tumour develops and also that without multi-region sequencing, the prevalence of HLA LOH may be significantly underestimated.

To shed further light on the timing of HLA LOH in NSCLC tumour evolution, we obtained sequencing data for 37 NSCLC primary tumours with matched brain metastases (Brastianos, 2015). Consistent with data from early stage NSCLC, we identified HLA LOH in 17/37 (46%) tumours and found that the LOH event occurred subclonally in 11/17 (65%) cases (FIG. 7G). Furthermore, when we compared primary and metastatic samples taken from the same patient, we observed an enrichment of HLA LOH in metastatic sites compared to the matched primary tumour (P=0.08), with seven patients harboring HLA LOH in the metastatic sample alone and only one patient where the converse was observed, with HLA LOH in the primary tumour alone (FIG. 7H). These results support the notion of HLA LOH occurring later in cancer evolution, and indicate that there may be selection for immune evasive mechanisms in late stage disease.

HLA Loss is Positively Selected in NSCLC

Figure 8:
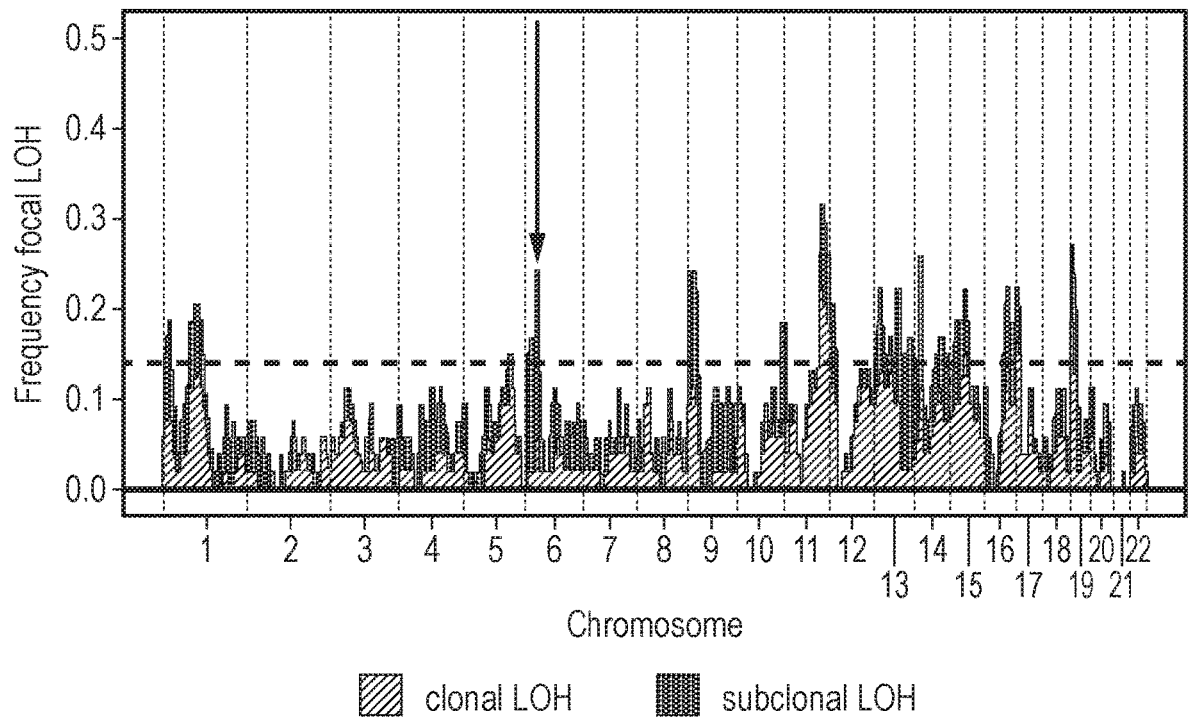
FIG. 8: HLA LOH reflects selection in NSCLC. Frequency of focal LOH in lung adenocarcinoma (A) and lung squamous cell carcinoma (B). Focal LOH is defined as <75% of a chromosome arm. Arrow indicates location of HLA locus. Horizontal dashed line depicts significant focal LOH at p=0.05, using simulations. Clonal LOH is shown in blue, with subclonal LOH shown in red. Chromosome arm LOH and focal subclonal LOH is shown in FIG. 11. (C) Parallel evolution of HLA LOH, with allele specific HLA loss shown on phylogenetic trees.
Figure 8:
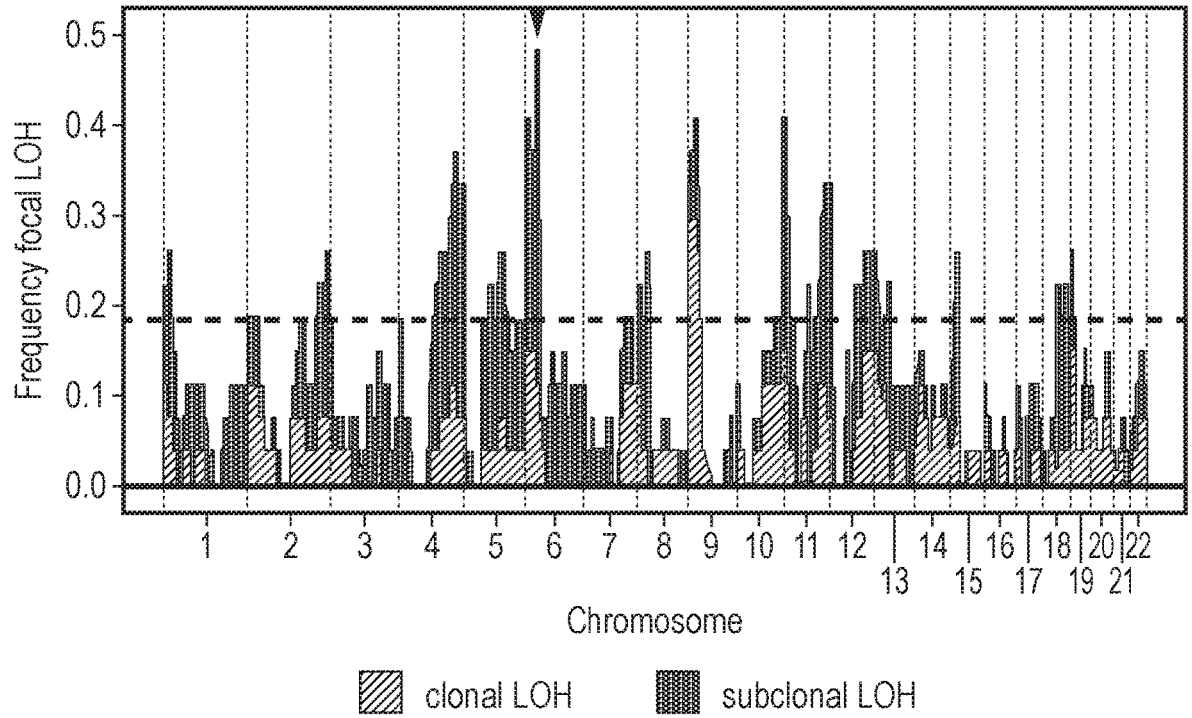
Figure 8:
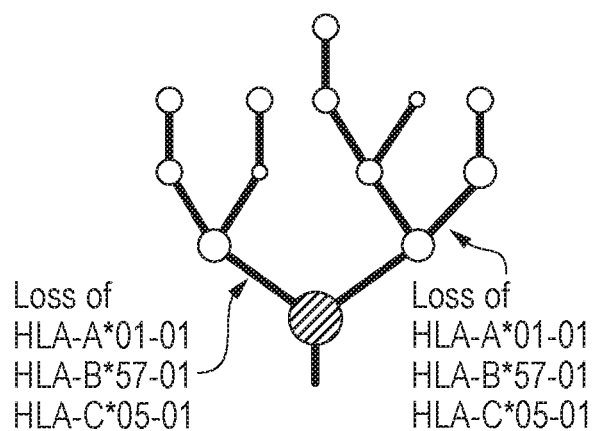
Figure 8:
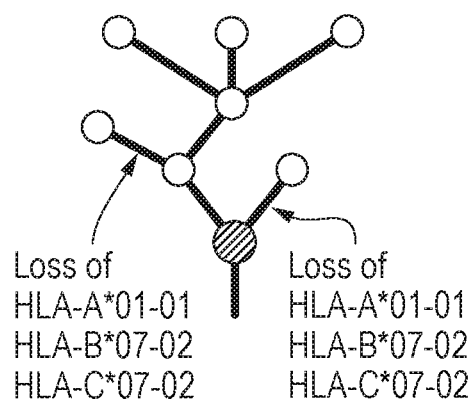
Figure 8:
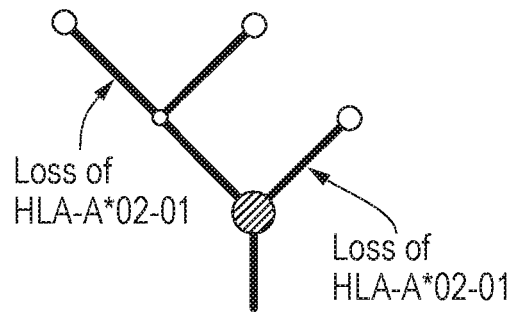
Figure 8:
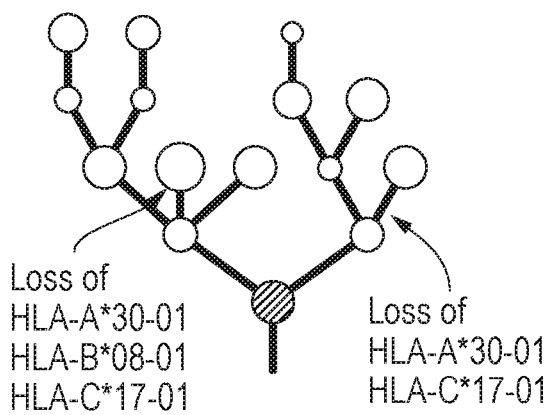
Figure 9:
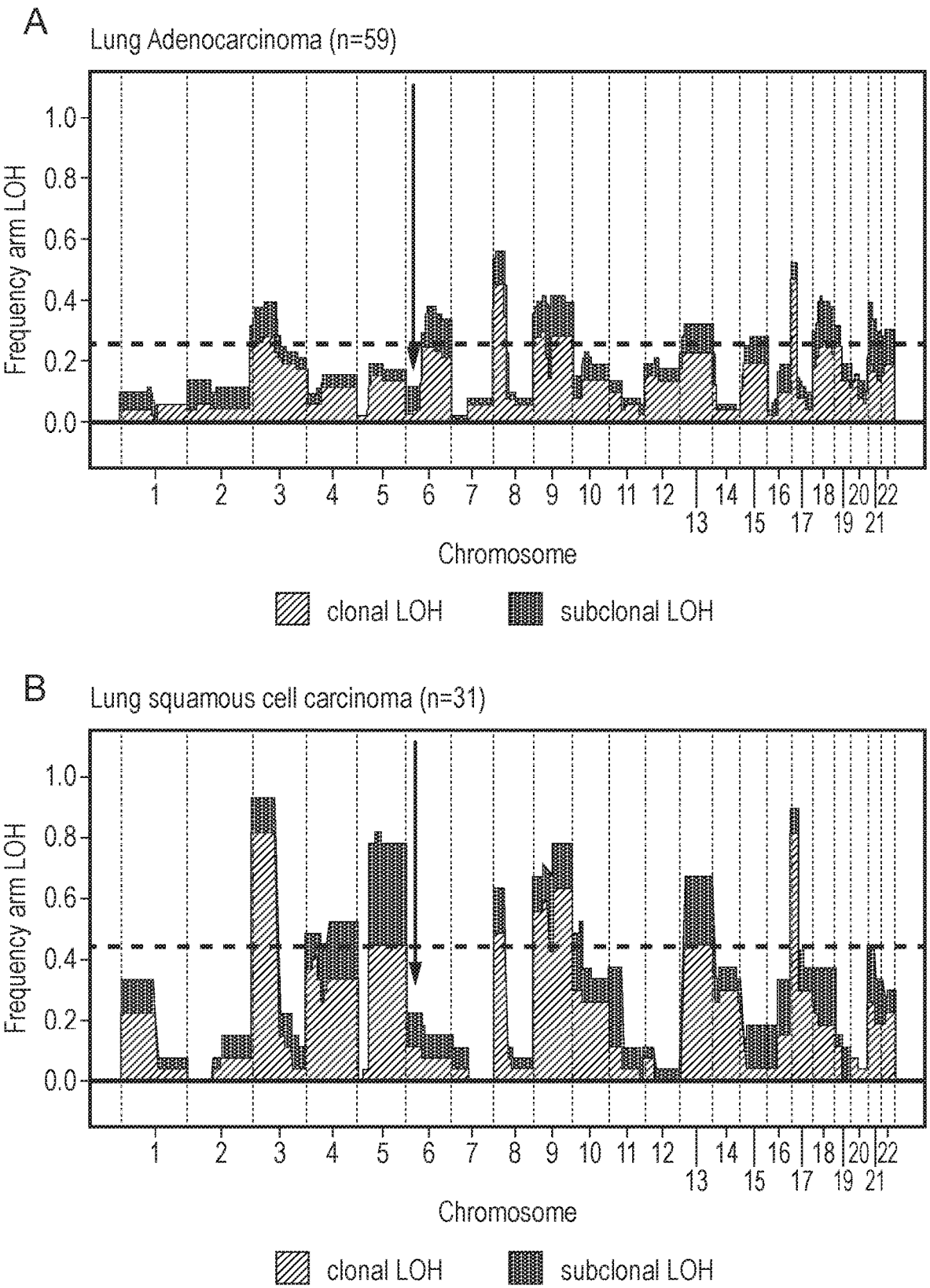
FIG. 9: Arm-level and focal subclonal LOH across the genome, related to FIG. 8. A-B) Arm-level LOH across the genome for lung adenocarcinoma (A) and lung squamous cell carcinoma (B). Arm-level LOH is defined as >75% of a chromosome arm. Arrow indicates location of HLA locus. Horizontal dashed line depicts significant focal LOH at p=0.05, using simulations. Clonal LOH is shown in blue, with subclonal LOH shown in red. C-D) Focal subclonal LOH across the genome for lung adenocarcinoma (C) and lung squamous cell carcinoma (D). Focal LOH is defined as <75% of a chromosome arm. Arrow indicates location of HLA locus.
Figure 9:
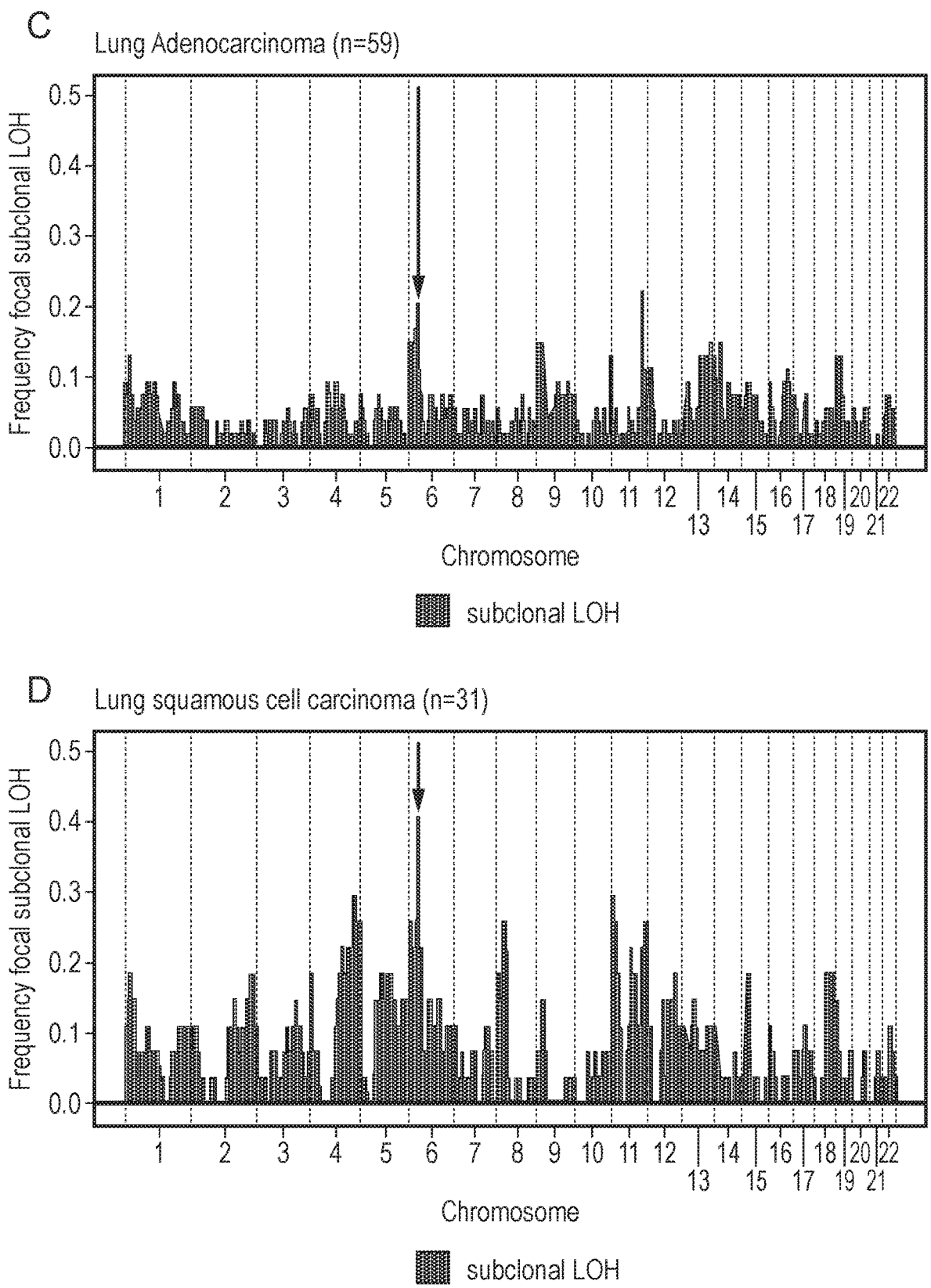

Given the relevance to immune evasion and high incidence of both clonal and subclonal LOH in HLA genes, we asked whether HLA LOH was significantly more frequent than expected by chance. Taking the frequency of LOH in every tumour into account, we simulated the expected frequencies of both focal and arm-level events. The observed frequency of focal, but not arm-level, HLA LOH occurred at a significantly greater frequency than expected by chance (FIG. 8, P<0.001, and FIG. 9). Indeed, we observed a clear peak in focal LOH centered around the HLA locus for both histological subtypes, strongly suggesting the HLA locus is subject to selective pressure during NSCLC evolution. This peak was more pronounced when restricting the analysis to subclonal LOH (FIG. 9), consistent with strong selection pressures later in tumour evolution.

Figure 6:
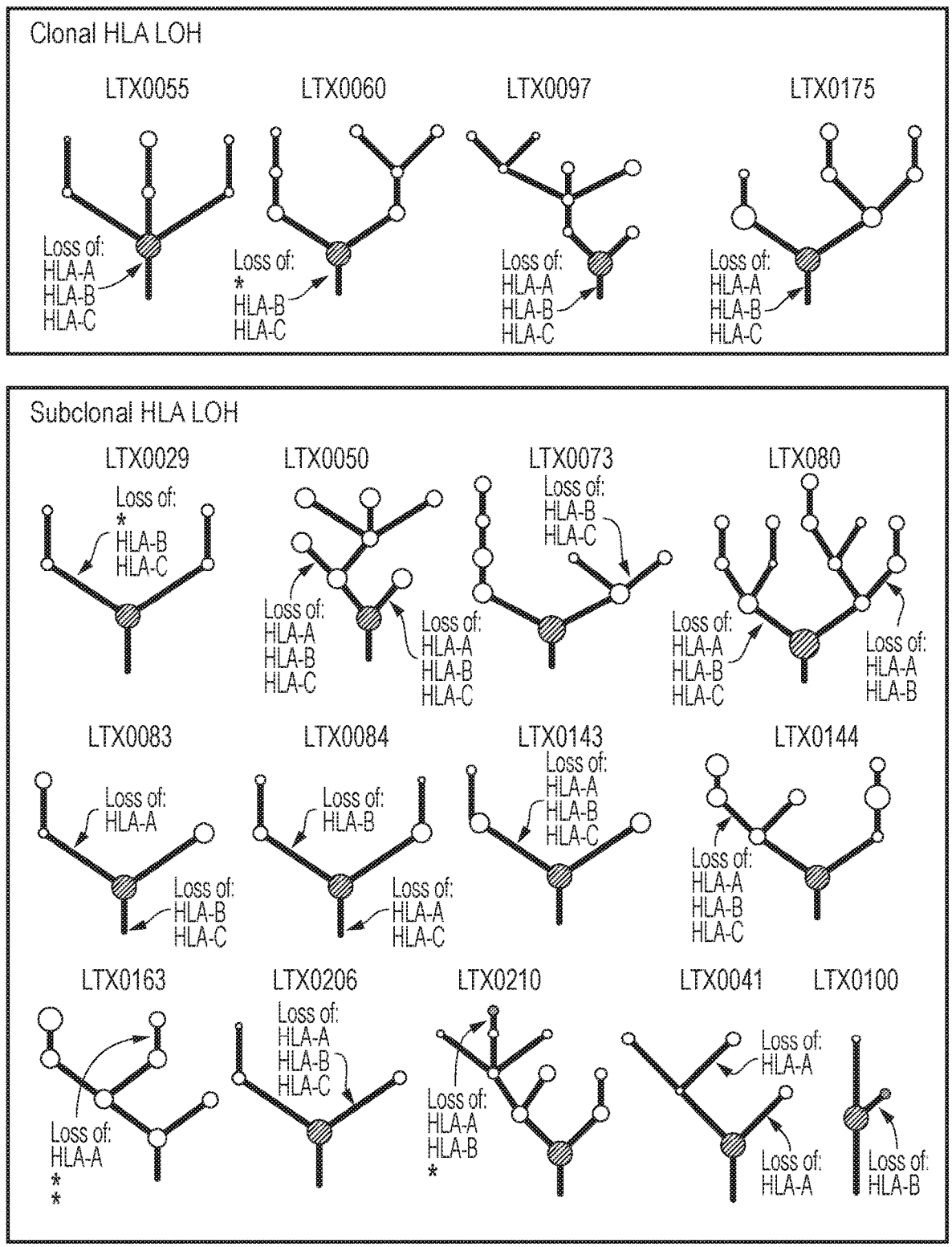
FIG. 6: Frequency and Timing of HLA LOH in NSCLC. Phylogenetic trees for each lung adenocarcinoma tumour showing evidence of HLA LOH have been annotated with the most likely timing of the HLA LOH event. Homozygous HLA alleles, where HLA LOH is not feasible, are indicated by an asterisk. Clusters of the phylogenetic tree are indicated as clonal (blue) or subclonal (red). In cases where the HLA LOH event did not map to a possible clone on the phylogenetic tree, an additional grey subclone was included.
Figure 7:
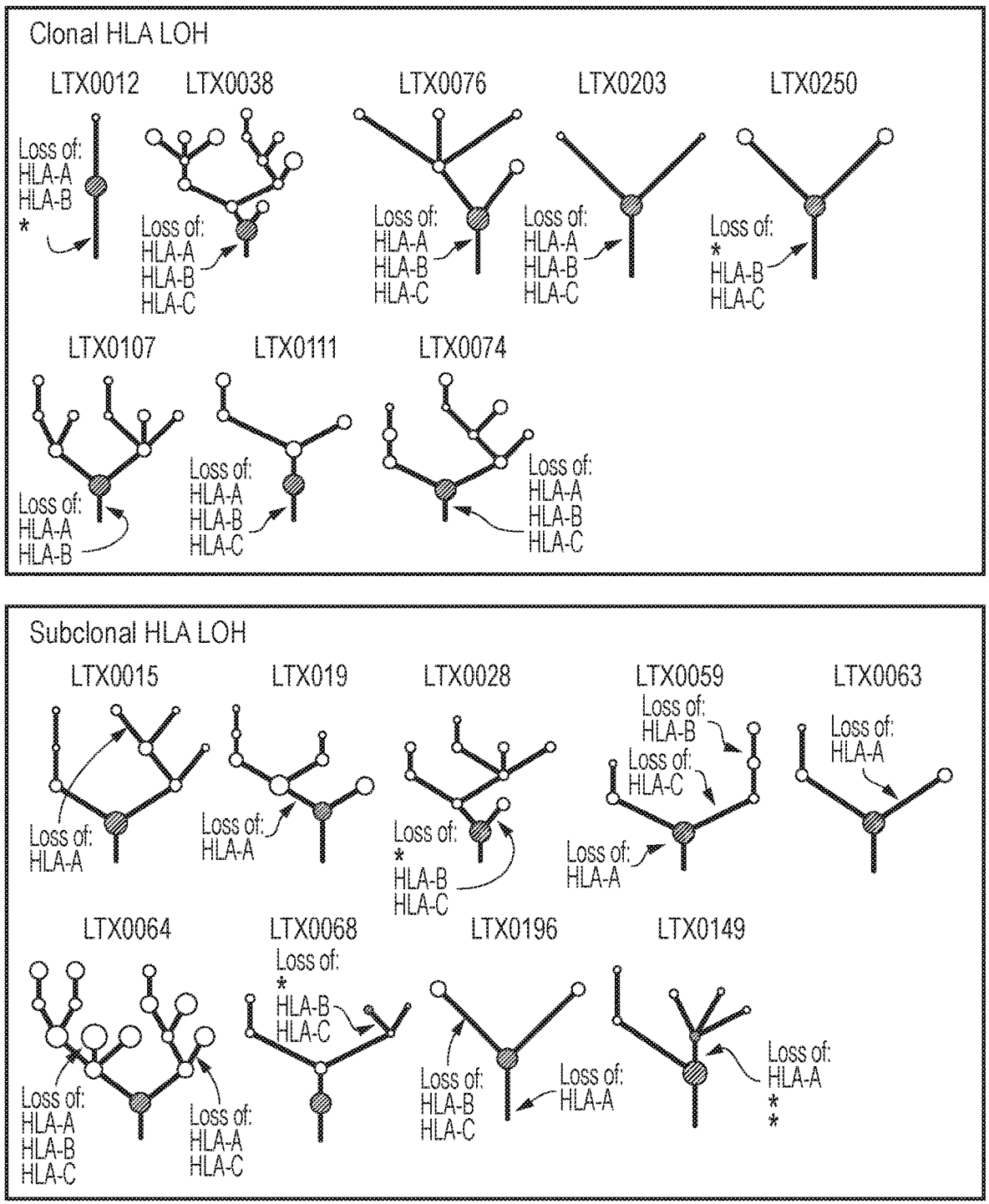
FIG. 7: Frequency and Timing of HLA LOH in NSCLC; Phylogenetic trees for each lung squamous cell carcinoma tumour showing evidence of HLA LOH have been annotated with the most likely timing of the HLA LOH event. Homozygous HLA alleles, where HLA LOH is not feasible, are indicated by an asterisk. Clusters of the phylogenetic tree are indicated as clonal (blue) or subclonal (red). In cases where the HLA LOH event did not map to a possible clone on the phylogenetic tree, an additional grey subclone was included. (G) Number of NSCLC patients with paired primary/brain metastasis sequencing data available exhibiting no HLA LOH (grey), HLA LOH in both the primary tumour and brain metastasis (green), HLA LOH only in the primary tumour (red), or HLA LOH only in the brain metastasis (blue). Patients with HLA LOH identified consistently across HLA loci in both the primary tumour and every brain metastases were considered to have clonal HLA LOH. Patients with inconsistent HLA loci subjected to LOH or those with HLA LOH identified in only a primary or brain metastasis sample were considered to have subclonal HLA LOH. (H) Timing of the HLA LOH events are shown. Clonal HLA LOH events occur in both the primary tumour sample and the brain metastases (green), whereas subclonal HLA LOH events either arise in the brain metastases (blue) or have occurred in a subclone of the primary tumour that does not seed the brain metastasis (red). Overall, an increase in HLA LOH is observed in the brain metastases samples as compared to the primary tumour (27% to 43%) and a corresponding decrease is observed in brain metastases samples exhibiting no HLA LOH (73% to 57%).
Figure 7:
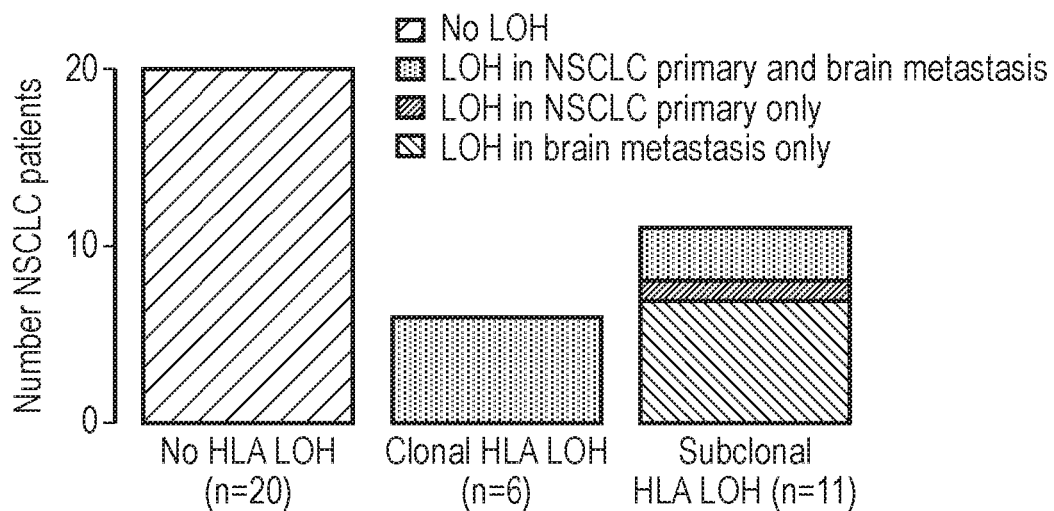
Figure 7:
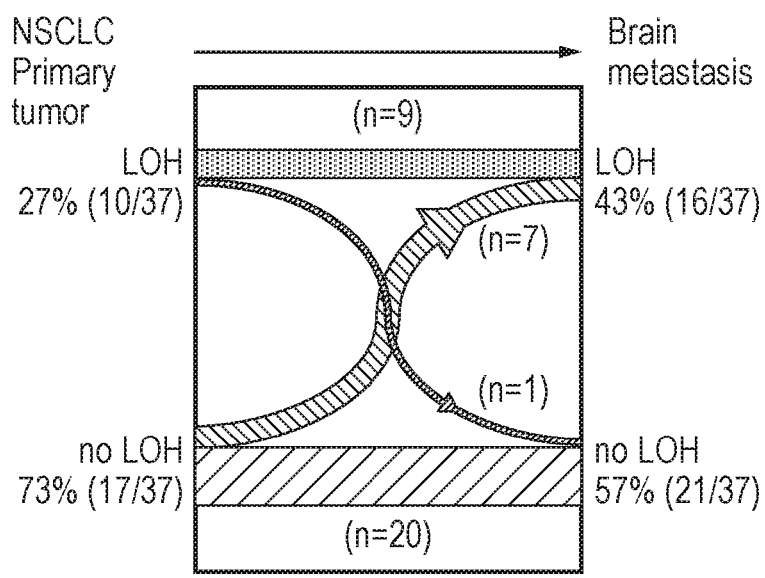

Moreover, in keeping with a strong selective pressure for HLA loss later in tumour evolution, in four tumours we observed losses of HLA haplotypes occurring as distinct events on separate branches of tumour's phylogenetic trees, indicative of parallel evolution with convergence upon HLA loss. For example, in LTX080 and LTX050, both lung adenocarcinomas, we found evidence of the same haplotype being lost within distinct subclones (FIG. 6 and FIG. 8C). Of note, in all four case where we observed parallel evolution, the same alleles were subject to loss on distinct branches, indicating that loss of these alleles specifically may have been required for for subclonal expansions. We also noted that in certain cases (for example, LTX041) only one HLA gene was subject allele specific loss, implying a selective benefit of perturbations to neo-antigen presentation associated with that gene specifically.

Taken together with the recently described significant mutation frequency in HLA genes across tumours (Shukla, 2015), these data implicate HLA LOH as a common mechanism of immune evasion in lung cancer evolution and, moreover, suggest the immune system acts as a strong selection pressure during branched tumour development.

It is also notable that while HLA LOH was identified in 37 tumours, we did not identify any tumours exhibiting homozygous deletions of HLA. Concordant with this observation, the variant allele frequencies of mutations that have been identified in HLA genes are indicative of a heterozygous state (Shukla, 2015). These data support the notion that a single copy of an HLA haplotype may be mandatory to avoid NK-mediated target cell lysis (Moretta, 2014).

HLA Loss Reflects Immune Editing and is Associated with an Enrichment of Subclonal Mutations Conceivably, if one of the homologous chromosomes harboring the HLA haplotypes were subject to copy number loss, the number of putative neoantigens presented to T cells would be reduced. Thus, we hypothesized that loss of an HLA haplotype may be permissive for subclonal expansions and would be associated with an elevated mutation/neo-antigen burden.

We first compared the number of non-synonymous mutations and neo-antigens present in tumour samples with and without LOH at the HLA locus, without taking into account timing or clonal nature of the HLA LOH event. While overall, we observed a significant increase in the number of non-synonymous mutations (FIG. 10A) and neo-antigens (FIG. 11A) in tumour samples exhibiting any HLA LOH, this did not remain significant when the subtypes were considered separately. (NSCLC p=0.016; lung adenocarcinoma p=0.07; lung squamous cell carcinoma p=0.82, wilcoxon test). Notably, however, we observed only 3/36 tumours with HLA LOH that exhibited a low mutational burden (as defined by the lowest quartile of NSCLC mutation burden), compared to 21/54 tumours without HLA LOH.

Figure 11:
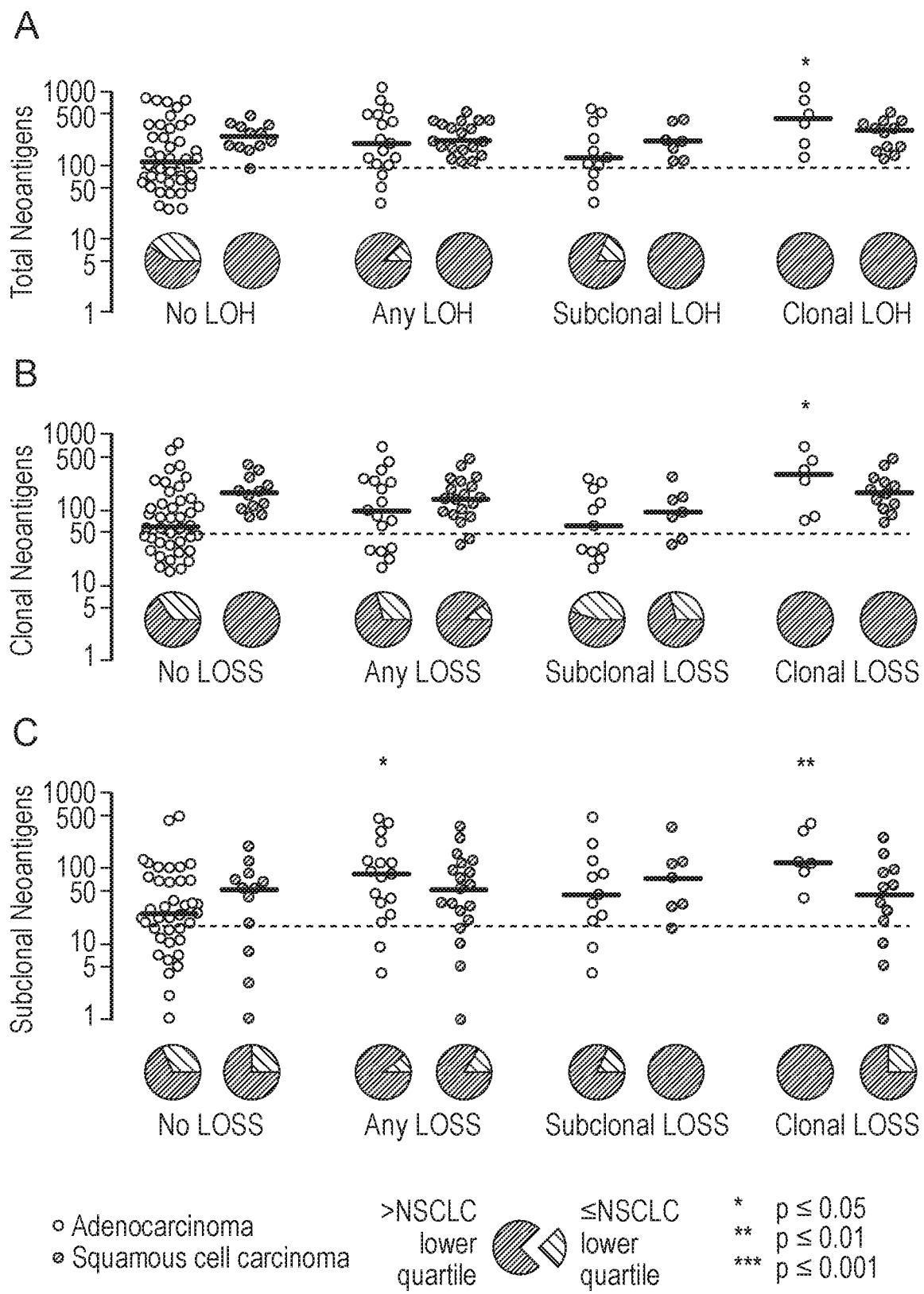
FIG. 11: Neoantigen and regional LOH associations, related to FIG. 10.
Figure 11:
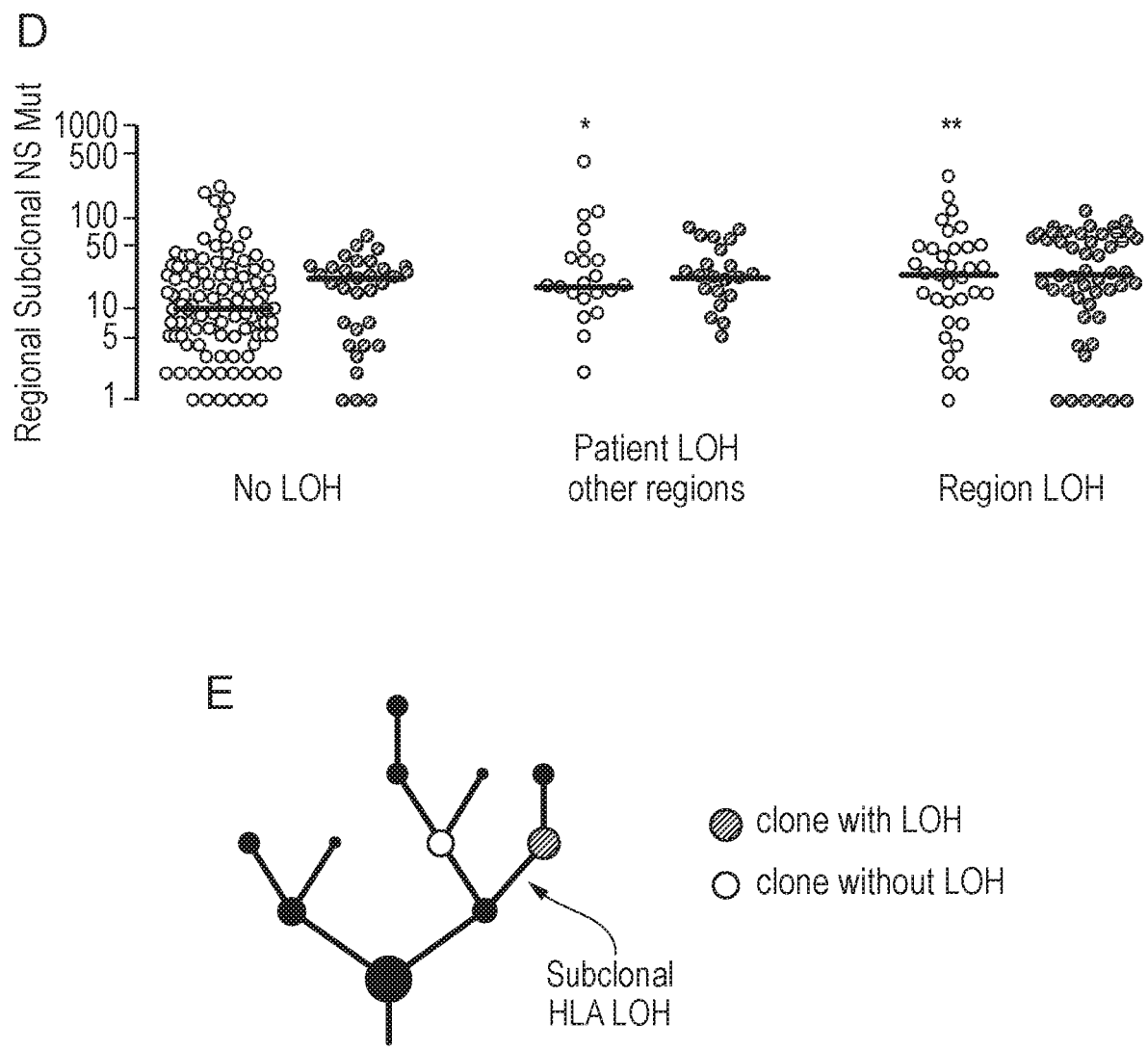

When we considered the clonal nature of mutations, we found that among tumours with HLA LOH there was a significant increase in the number of subclonal, but not clonal, non-synonymous mutations (FIG. 10B-C) (NSCLC p=0.008; lung adenocarcinoma p=0.01; lung squamous cell carcinoma p=0.6, wilcoxon test) and neo-antigens (FIG. 11B-C). This observation is consistent with HLA LOH frequently occurring as a branched, subclonal, event, and indicates that HLA LOH may allow for the accumulation of potentially antigenic subclonal mutations (FIG. 10C). Consistent with this, we found that when HLA LOH occurred as a clonal event, on the trunk of a tumour's phylogenetic tree, this was significantly associated with both an elevated clonal (NSCLC p=0.002; lung adenocarcinoma p=0.01; lung squamous cell carcinoma p=0.29, wilcoxon test) and subclonal (NSCLC p=0.03; lung adenocarcinoma p=0.004; lung squamous cell carcinoma p=0.89, wilcoxon test) non-synonymous mutation and neo-antigen burden (FIG. 10B, FIG. 11B).

When we considered HLA LOH events at the region-level, we also observed a significant increase in subclonal mutations between tumour regions exhibiting HLA loss compared to tumour regions from patients without any evidence for HLA LOH (FIG. 11D; NSCLC p=1.9e-05; lung adenocarcinoma p=0.009; lung squamous cell carcinoma p=0.07). Interestingly, even in tumour regions without HLA LOH, but evidence for HLA LOH in the tumour as a whole, we observed a significantly higher burden of subclonal mutations compared to tumour regions derived from tumours without any evidence for HLA LOH (FIG. 11D). Thus, while HLA LOH may allow for subsequent subclonal expansion, a tumour with a high mutational burden may be under increased selective pressure for the HLA LOH event.

We next considered the specific cancer subclones in which HLA LOH events occurred, allowing us to more directly assess the impact of HLA LOH on non-synonymous mutation and neoantigen burden in cancer cells (FIG. 11E). In tumours with subclonal HLA LOH, we directly compared the mutational burden of the cancer subclone harboring HLA loss with its sister subclone, descended from the same ancestral cancer cell, but without HLA loss. Subclones with HLA LOH consistently showed a higher non-synonymous mutational burden than their counterparts without HLA LOH regardless of histological subtype (FIG. 10D; NSCLC p=4e-04; lung adenocarcinoma p=0.018; lung squamous cell carcinoma p=0.008). Indeed, there were only two instances of the subclone with HLA LOH having fewer non-synonymous mutations than its sister subclone without HLA LOH. This result suggests that HLA LOH directly contributes to the observed increase in subclonal non-synonymous mutations among tumours harboring HLA LOH.

While there were only three instances of low mutational burden in tumours harboring an HLA LOH event (FIG. 10A) and an increase in mutation burden in subclones harboring HLA LOH was observed in both cancer types, we noted that a significant increase in non-synonymous mutation burden in tumour regions with loss of an HLA allele was only observed among the lung adenocarcinomas. This suggests that while HLA LOH may allow for acquisition of subclonal mutations, there are additional mechanisms in lung squamous carcinomas contributing to the observed high subclonal mutational burden in tumours without HLA LOH.

Figure 12:
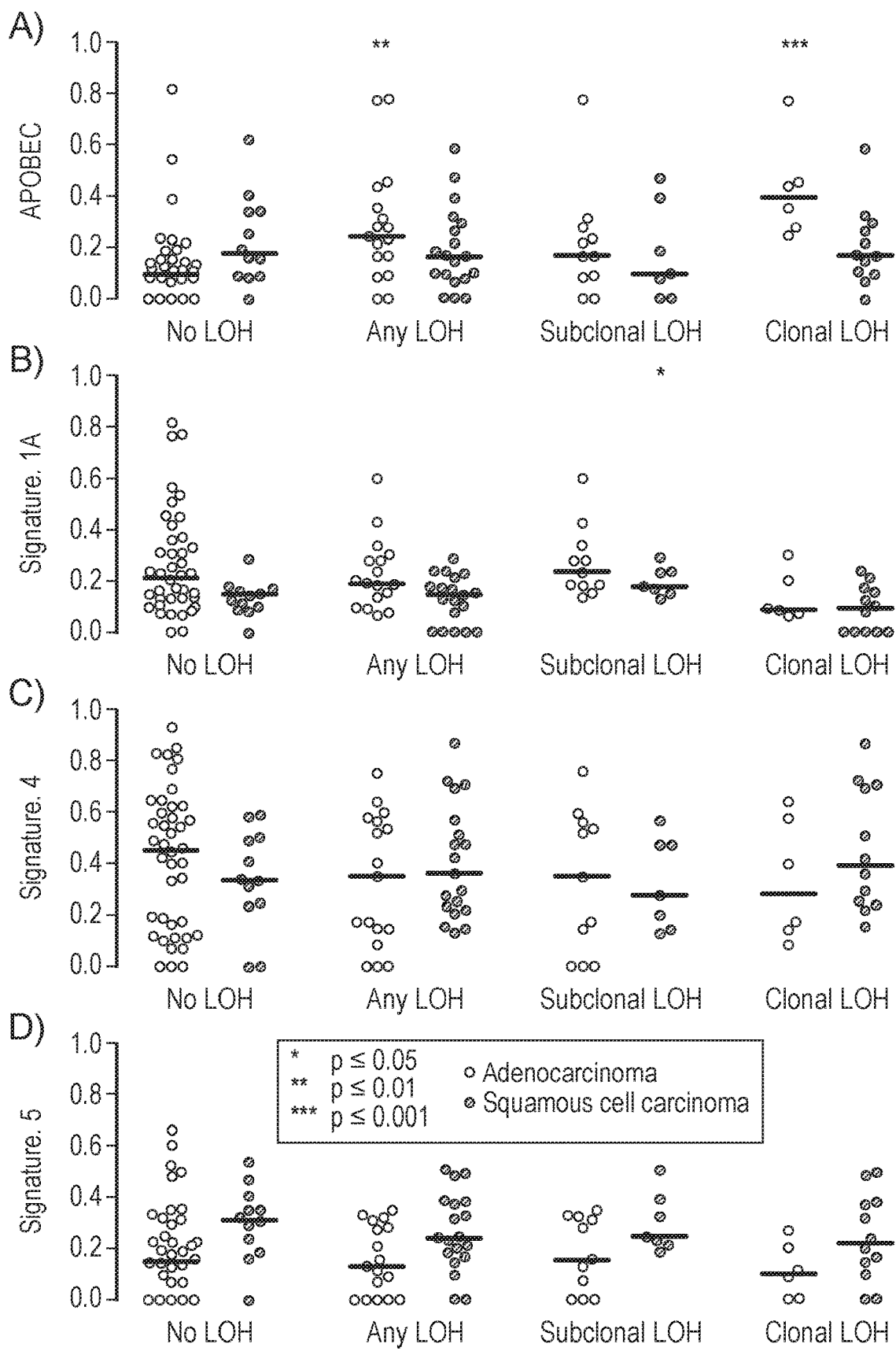
FIG. 12: Signature LOH associations, related to FIG. 10.

To address whether a particular mutational process contributes to the subclonal mutational burden present in tumours with HLA LOH, we interrogated the mutational signatures present in each tumour (Alexandrov, 2013; Rosenthal, 2015). Among lung adenocarcinoma tumours that exhibited any HLA LOH, we observed a significant increase in the APOBEC mutagenic signatures (Signature 2 and Signature 13) (NSCLC p=0.03; lung adenocarcinoma p=0.003, lung squamous cell carcinoma p=0.63); however, no other signature found in this cohort (Signatures 1A, 4, and 5) appeared to differentially contribute between groups (FIG. 12).

Only neoantigens binding to the kept HLA alleles will be presented to the immune system. Therefore, we reasoned that if HLA LOH reflects cancer immune-editing one would expect to observe an enrichment of subclonal neoantigens predicted to bind to the lost HLA alleles compared to the kept HLA alleles. We therefore further investigated tumours with 6 distinct HLA alleles and loss of one HLA haplotype (3 alleles) in at least one tumour region (n=20; 9 lung adenocarcinomas and 11 lung squamous cell carcinoma). Consistent with LOH at the HLA locus representing immune editing and facilitating accumulation of subclonal neoantigens, we observed a significant enrichment for subclonal neoantigens predicted to bind to the lost HLA alleles compared to the kept alleles (FIG. 10E) (P=0.0083, paired wilcoxon test). This remained significant when restricting the analysis to lung squamous cell carcinomas, but not lung adenocarcinomas (lung adenocarcinoma, P=0.29; lung squamous cell carcinoma, P=0.02). In one tumour, LTX083, a lung adenocarcinoma, we observed a total of 1220 mutations predicted to yield neoantigens, of which 92% were predicted to bind to lost HLA alleles.

To determine more generally the impact HLA LOH could have on which neoantigens are presented to the immune system, we identified neoantigens predicted to bind to lost alleles in the full cohort of 37 patients exhibiting any HLA LOH (FIG. 10F). We found that all patients harbored mutations predicted to bind to a now lost HLA allele, highlighting the potential impact HLA LOH could have on the targeting of putative neo-antigens in a clinical setting, such as through personalized neoantigen vaccine approaches (Ott, 2017; Sahin, 2017). Notably, this analysis would not be possible without HLA haplotype specific copy number estimates.

HLA Loss and Immune Phenotype

Next, to investigate whether HLA loss is associated with a specific tumour microenvironment, we performed immunohistochemistry analysis to determine the expression of PDL1 on both tumour and immune cells. PDL1 is a ligand to the immune inhibitory receptor PD1 and its expression may reflect a cancer adaptive immune response to an active immune system.

We found tumours exhibiting clonal HLA LOH were characterized by significantly elevated PDL1 staining of immune cells compared to tumours without any HLA LOH (P=0.029), and a trend was observed for elevated PDL1 staining on tumour cells (P=0.14). These data are consistent with the notion that HLA LOH may facilitate immune escape in response to an active immune microenvironment.

Finally, to validate our findings in a larger cohort and to explore whether HLA LOH is associated with an immune phenotype, we obtained 383 lung adenocarcinomas and 309 lung squamous-cell carcinomas samples from TCGA (Campbell, 2016).

In keeping with results from the TRACERx cohort, we found HLA LOH was highly prevalent in lung squamous-cell carcinomas (133/309) and lung adenocarcinomas (118/383) tumours, again being a more common event in lung squamous cell carcinomas (p=0.001, Fisher's exact test) (FIG. 13A). Due to the increased sample size from TCGA, we could also further analyze samples that had HLA LOH at a single locus (56 lung squamous cell carcinoma, 56 lung adenocarcinoma) or HLA LOH at all three HLA loci (77 lung squamous cell carcinoma, 62 lung adenocarcinoma). In agreement with the TRACERx samples, a significantly higher non-synonymous mutation burden was observed in lung adenocarcinomas tumours exhibiting HLA LOH (p=0.0001, wilcoxon test), regardless of whether the HLA LOH affected a single loci (p=0.002, wilcoxon test) or all three HLA loci (p=0.003, wilcoxon test) (FIG. 13B). Notably, for this dataset, where RNA-seq was available, we observed no significant difference in RNAseq expression of HLA-A, B or C between tumours with and without HLA-LOH indicating that RNA, without considering haplotype-specificity using LOHHLA, cannot be used to reliably identify HLA LOH.

Previous work has identified immune signatures indicative of immune activity and/or immune cell infiltrates (Rooney, 2015; Li, 2016; Davoli, 2017). By using these signatures, we were able to investigate whether HLA loss was associated with a specific immune phenotype. In lung adenocarcinoma with HLA LOH at all three loci, we observed an increase in abundance of CD8+ T cells, as estimated by a previously published method (Li) (p=0.04, wilcoxon test). Additionally, in both lung adenocarcinoma and lung squamous cell carcinomas with HLA LOH, we identified a significantly elevated cytolytic activity score, which measures the levels of two genes upregulated upon CD8+ T cell activation, granzyme A (GZMA) and perforin (PRF1) (Rooney) (FIG. 13C). In lung adenocarcinoma with HLA LOH at all three loci, we observed an increase in abundance of CD8+ T cells and expression profiles associated with improved checkpoint blockade response (Li, 2016; Rooney, 2015; Tumeh, 2014; Herbst, 2014; Ribas, 2015; Piha-Paul, 2016). Additionally, we identified an increase in NK cells, suggesting that HLA LOH alone may interrupt inhibitory NK cell/MHC interactions (FIG. 13C). Differential expression analysis between tumours with and without LOH confirmed an increase of PD-L1 and effector molecules such as granzymes-A, B, and -H, as well as STAT1 and IFNγ, in lung adenocarcinoma with HLA LOH but not lung squamous cell carcinoma. These data suggest that lung adenocarcinoma tumours with HLA loss have a more active immune microenvironment and disruption of antigen presentation may act as a mechanism to evade the immune system.

TABLE S1

Immune genes significantly differentially expressed in lung adenocarcinomas with HLA LOH vs without HLA LOH

|       | baseMean    | log2FoldChar | lfcSE      | stat       | pvalue     | padj       |
|-------|-------------|--------------|------------|------------|------------|------------|
| ADAR  | 20464.572   | 0.33681769   | 0.07050847 | 4.77698168 | 1.78E−06   | 0.00023037 |
| CD244 | 80.3637882  | 0.4386209    | 0.15169315 | 2.89150098 | 0.00383406 | 0.03555357 |
| CD274 | 252.875369  | 0.62413258   | 0.182343   | 3.4228492  | 0.00061968 | 0.01092229 |
| CISH  | 2152.3247   | −0.5647881   | 0.13152013 | −4.2943097 | 1.75E−05   | 0.00107987 |
| CNTFR | 16.4832332  | −0.930897    | 0.2251708  | −4.1341818 | 3.56E−05   | 0.00167619 |
| CXCL10| 1661.47782  | 0.51766283   | 0.18737132 | 2.76276452 | 0.00573141 | 0.04635113 |
| GZMA  | 513.167711  | 0.68095869   | 0.16875497 | 4.03519182 | 5.46E−05   | 0.0022004  |
| GZMB  | 483.606115  | 0.57112356   | 0.17806044 | 3.20747029 | 0.00133908 | 0.01792377 |
| GZMH  | 192.868787  | 0.50567793   | 0.17441457 | 2.89928727 | 0.00374012 | 0.03500216 |
| HHLA2 | 1420.84224  | −0.830894    | 0.24216229 | −3.4311453 | 0.00060104 | 0.01074405 |
| HLA-DQB1 | 12945.44 | −0.562477   | 0.1703199  | −3.3024737 | 0.00095836 | 0.01432935 |
| IFNG  | 38.6691528  | 0.59658884   | 0.21148721 | 2.82092158 | 0.00478859 | 0.0411964  |
| IFRD1 | 1773.18959  | 0.30982523   | 0.11285137 | 2.74542723 | 0.00604322 | 0.04773899 |
| IL15  | 223.10475   | 0.44811921   | 0.13461896 | 3.32879715 | 0.00087222 | 0.01355629 |
| IL1A  | 54.8220652  | 0.8953501    | 0.20896873 | 4.2846128  | 1.83E−05   | 0.00109258 |
| IL1B  | 346.227047  | 0.62701377   | 0.16223619 | 3.86482063 | 0.00011117 | 0.00354474 |
| IL2RB | 1121.20854  | 0.39996941   | 0.13922619 | 2.872803   | 0.00406848 | 0.03699801 |
| IRF1  | 3852.92659  | 0.39739594   | 0.11506885 | 3.45354929 | 0.00055326 | 0.01013419 |
| IRF4  | 646.735229  | 0.49456082   | 0.1754994  | 2.81802001 | 0.00483208 | 0.04136758 |
| MADCAM1 | 9.08894517 | −0.5386424 | 0.19674534 | −2.7377645 | 0.00618584 | 0.04846157 |
| MPL   | 32.644779   | −0.31813     | 0.11368205 | −2.7984185 | 0.00513535 | 0.04315725 |
| NR4A1 | 6647.98795  | −0.557312    | 0.17719956 | −3.1451096 | 0.00166025 | 0.02061118 |
| PVR   | 2921.01052  | 0.25504895   | 0.09367721 | 2.72263614 | 0.00647633 | 0.04996622 |
| SP110 | 1343.37583  | 0.23814933   | 0.08717816 | 2.73175438 | 0.00629981 | 0.04891736 |
| STAT1 | 16843.0562  | 0.36611007   | 0.11898785 | 3.07686942 | 0.00209187 | 0.0239596  |
| TAP1  | 9613.85234  | 0.36988624   | 0.13172484 | 2.80802204 | 0.00498468 | 0.04220568 |
| TNFSF13 | 3083.20997 | −0.3707851 | 0.1037302  | −3.5745142 | 0.00035088 | 0.00751138 |
| ULBP1 | 80.3432407  | 0.51683211   | 0.17451923 | 2.96146224 | 0.00306182 | 0.03082616 |

Discussion

Figure 14:
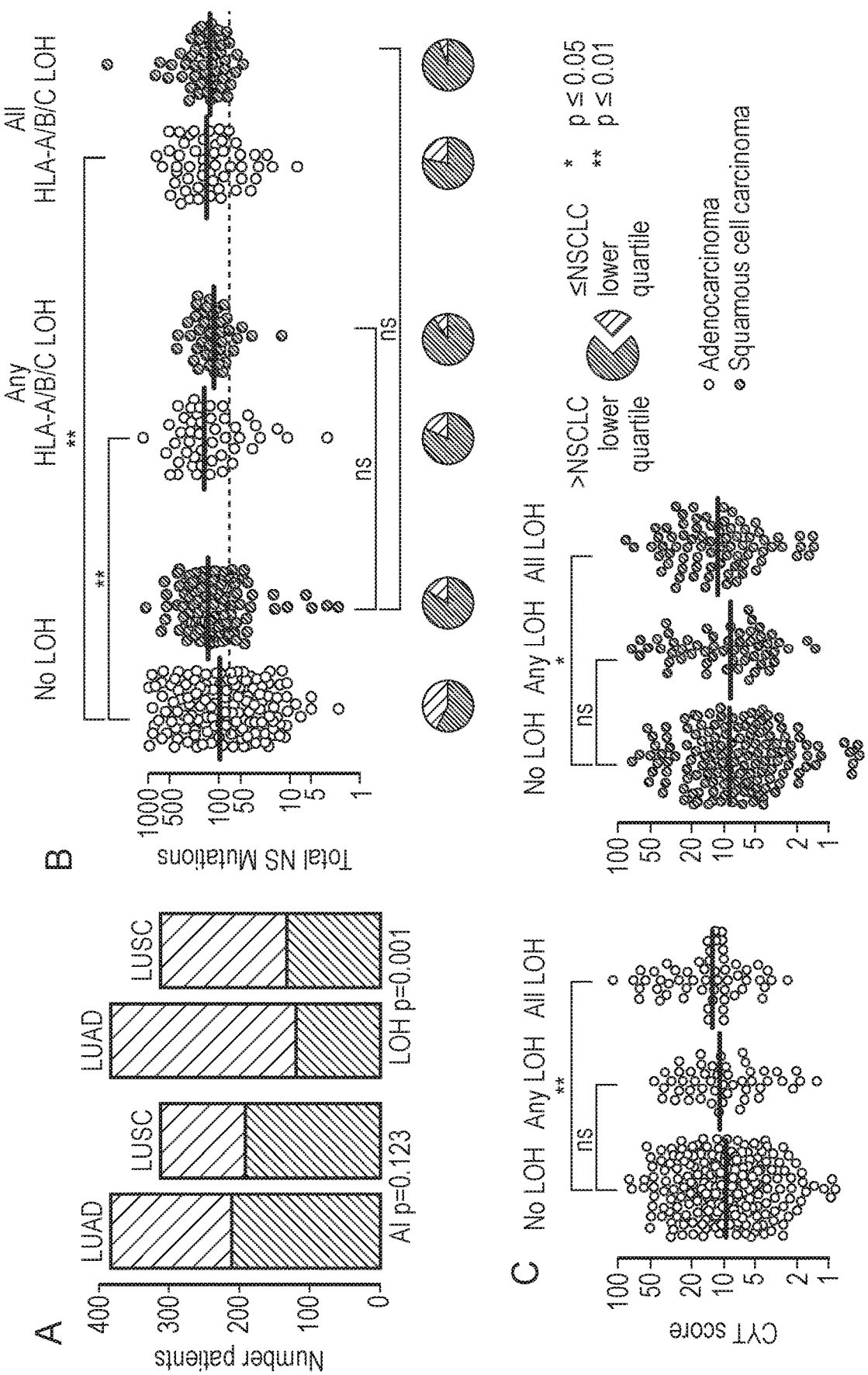
FIG. 14: Associations of HLA Allelic Imbalance and HLA LOH in TCGA data. (A) Proportion of HLA allelic imbalance and HLA LOH identified in NSCLC by sub-type. Enrichment significance was tested using a Fisher's Exact Test. (B) The total number of non-synonymous mutations is plotted across different categories of HLA LOH for lung adenocarcinoma (light blue) and lung squamous cell carcinomas (magenta). Tumours could either be classified as having no HLA LOH, HLA LOH at either the HLA-A, HLA-B, or HLA-C locus or HLA LOH at all HLA class I three loci. The lowest total non-synonymous mutation quartile is indicated by the dashed red line and the proportion of tumours with a total non-synonymous mutational burden greater or less than that is indicated by the pie charts for each HLA LOH classification group. (C) Cytolytic activity (CYT) scores, defined as the log-average (geometric mean) of GZMA and PRF1 expression in transcripts per million (TPM), is shown for lung adenocarcinoma (light blue) and lung squamous cell carcinomas (magenta).
Figure 15:
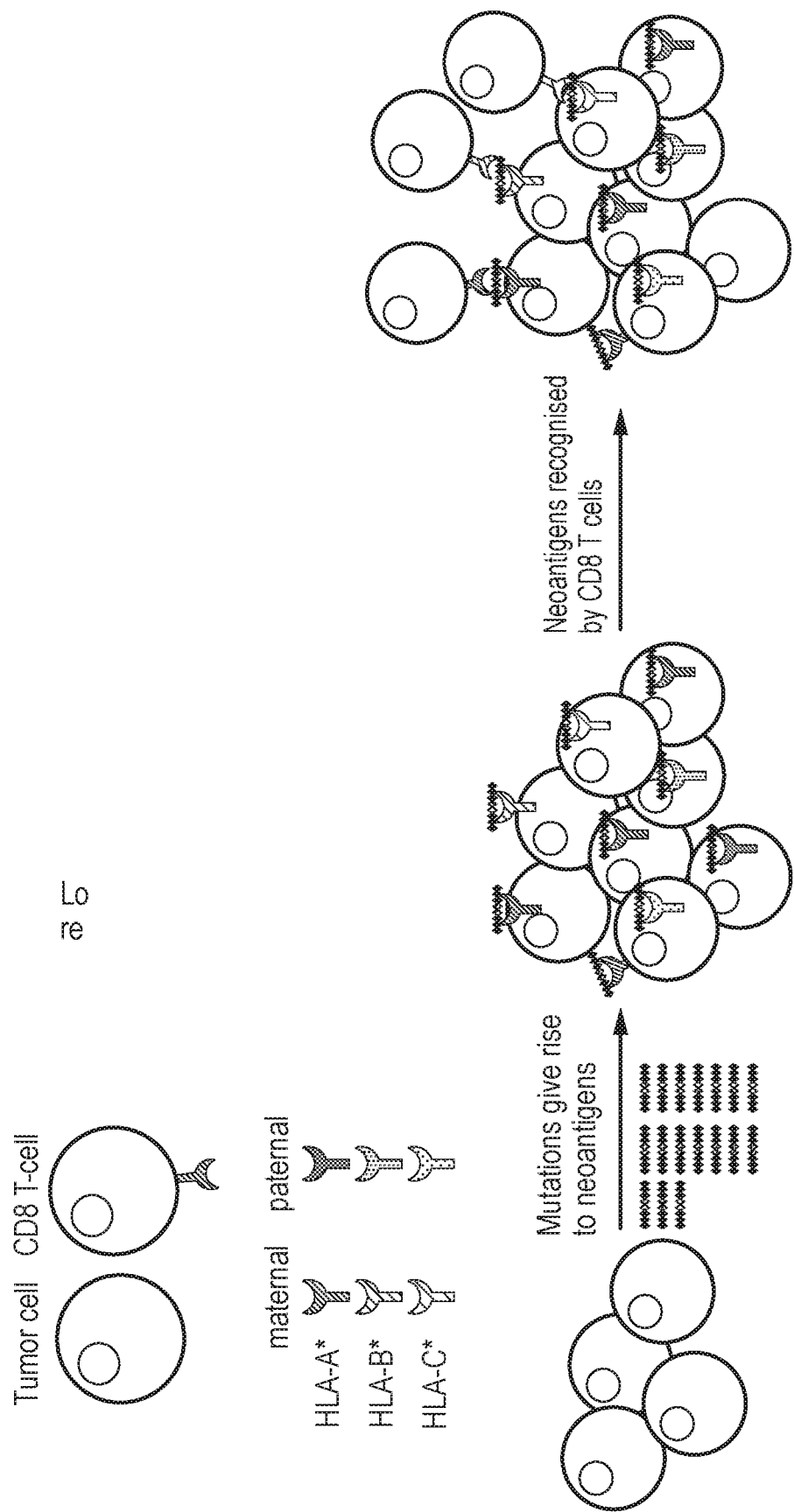
FIG. 15: Model of HLA allele specific loss in NSCLC. Model illustrating how HLA LOH may lead to immune escape in tumours. During tumour evolution, the accumulation of neoantigens may induce local immune infiltrates, including CD8 T-cells. Local immune infiltrates act as a selection barrier for tumours. Subclones with HLA LOH may be selected as these can evade killing by avoiding CD8 T-cell recognition. Alternatively, other subclones may evade killing by release of immune inhibitory molecules.
Figure 15:
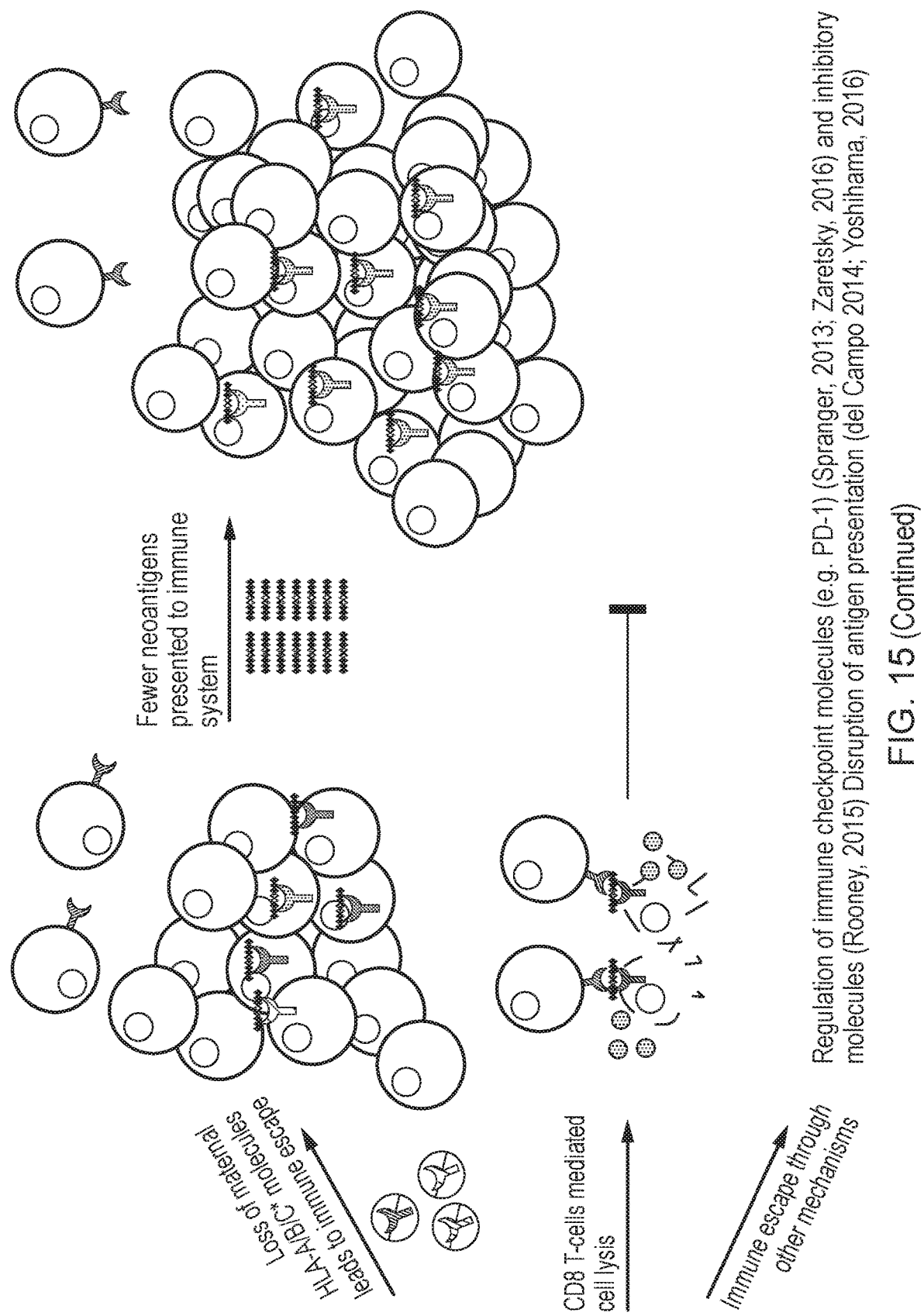

Losing the ability to present productive tumour neoantigens could result in evasion from immune predation. An integral part of neoantigen presentation is the HLA class I molecule, which presents epitopes to T-cells on the cell surface. Thus, loss of an HLA allele, resulting in HLA homozygosity, may be a mechanism of immune escape (FIG. 14).

However, the polymorphic nature of the HLA locus precludes accurate copy number calling using conventional copy number tools. Here we present LOHHLA, a tool to systematically evaluate the prevalence and importance of HLA loss in lung cancer evolution using next-generation sequencing data (FIG. 1).

We evaluated the performance of LOHHLA using two independent methods. We found LOHHLA LOH and allelic imbalance estimates were consistently in agreement with those inferred from adjacent genomic segments using the state of the art copy number tool ASCAT (Van Loo, 2010). Fragment analyses of polymorphic stretches of DNA validated the accuracy of LOHHLA. Importantly, LOHHLA is also able to determine which specific HLA haplotype is subject to copy number loss, which is not possible using conventional copy number tools.

Using LOHHLA, we find that HLA loss occurs in 40% of early-stage NSCLCs. The focal nature and high frequency, beyond that expected using simulations, suggest HLA LOH and immune-editing is strongly selected for in NSCLC evolution. The subclonal frequency of HLA loss, occurring in a subset of cancer cells on the branches of tumour's phylogenetic trees, suggests it is often a later event in tumour evolution and that the local, region-specific, immune microenvironment may act as a key selective force in shaping branched tumour evolution. Consistent with this, in four tumours, we observed evidence for parallel evolution of HLA loss, suggesting that escape from immune predation represents a significant constraint to tumour evolution. These results have parallels with observations in HIV whereby patients with homozygous HLA alleles exhibit rapid progression to AIDS compared to patients with heterozygous HLA alleles (Martin and Carrington, 2013).

In both lung adenocarcinomas and lung squamous cell carcinomas, subclones harboring HLA LOH were associated with a significantly elevated subclonal non-synonymous mutation/neoantigen burden compared to subclones descended from the same ancestral cancer cell but without HLA LOH. Moreover, HLA LOH was associated with RNA signatures of immune activation, and tumours with HLA LOH were found to exhibit an enrichment of neoantigens predicted to bind to the lost HLA alleles These data suggest that loss of HLA alleles, under the selective pressure of immune predation, may be permissive for subclonal expansions and result in previously antigenic mutations becoming effectively invisible to the immune system.

The high mutational load and low levels of HLA expression in lung squamous cell tumours (McGranahan, 2016), even in tumours without HLA LOH suggests alternative mechanisms of immune evasion, such as up-regulation of immune suppressive molecules (e.g. PD-1, LAG3) (Spranger 2013) and/or disruption of neoantigen presentation through other mechanisms (e.g. mutations to B2M or NLRC5) (del Campo 2014; Yoshihama, 2016) may occur in this subset of cancers. In this regard, we note that LOHHLA could be extended to perform haplotype specific copy number on any genomic segment that has been subject to haplotyping. For instance, if HLA class II typing has been performed, LOHHLA can be implemented to assess the extent to which loss of HLA class II occurs in tumour evolution, and which haplotype is subject to loss.

In conclusion, LOHHLA enables accurate estimation of haplotype specific HLA loss, revealing that HLA LOH is a common feature of NSCLC, facilitating immune escape and subclonal genome evolution.

Example 2

The LOHHLA algorithm can also be implemented to explore HLA class II LOH.

Figure 16:
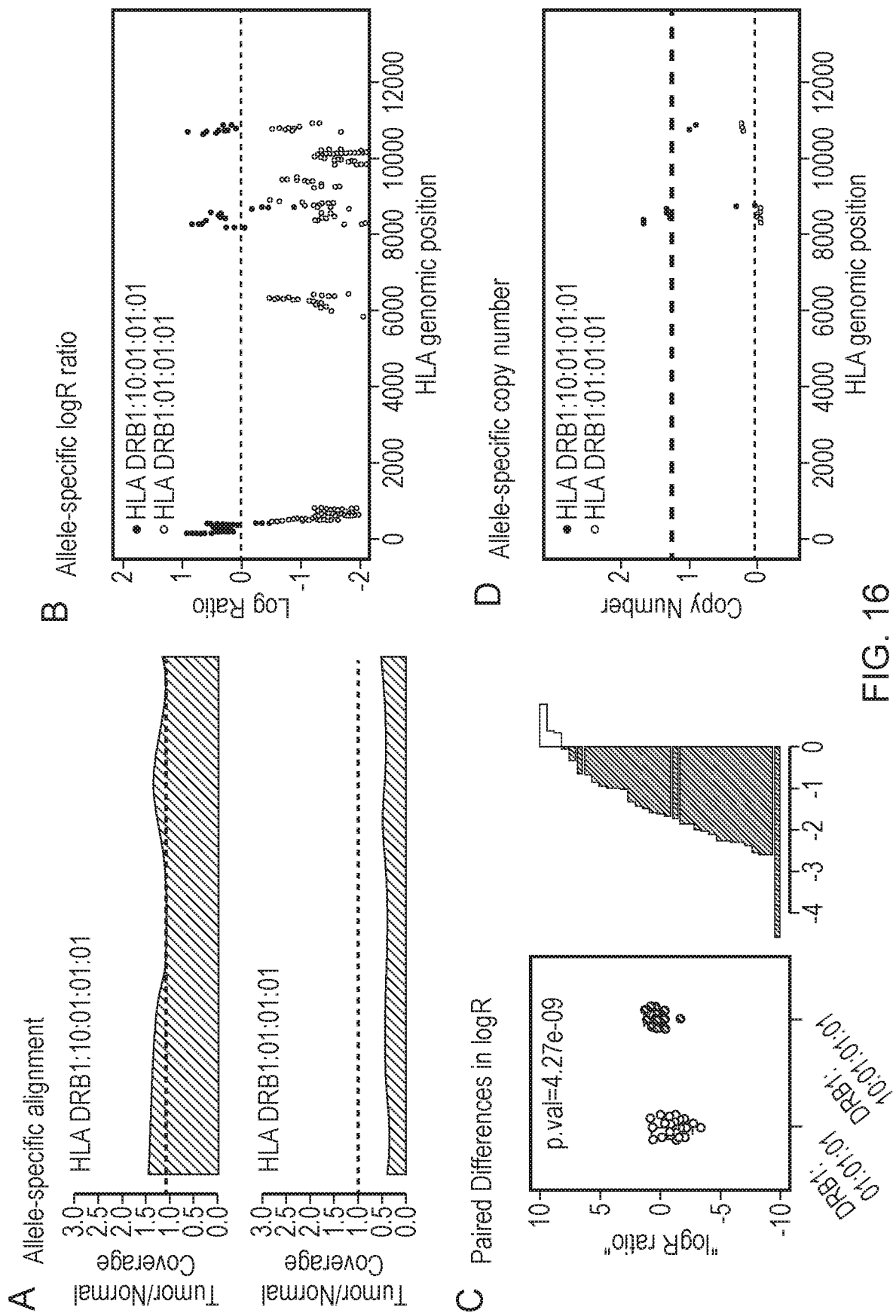
FIG. 16: Application of LOHHLA for inference of HLA class II Allele specific copy number in a tumour. A) Allele specific alignment of LOHHLA for HLA-DRB1 allele. B) Allele specific log R ratio for the two HLA DRB1 alleles C) Paired difference in log R at identified heterozygous positions. D) HLA DRB1 allele specific copy number. Notably HLA DRB1:01:01:01 is identified as present at zero copies, indicating an HLA loss event.

As illustrated in FIG. 16, provided HLA class II typing has been performed, LOHHLA enables assessment of allele specific copy number. In this case, HLA tying of the HLA-DRB1 locus was performed using xHLA [Xie, PMDI: 28674023] and revealed that the patient harboured two distinct alleles, DRB1:10:01:01:01 and DRB1:01:01:01.

Alignment of normal and tumour sequence reads to the patient specific HLA-alleles using LOHHLA (as outlined in Example 1) demonstrates imbalance of HLA-alleles (FIG. 16-A-C). Incorporation of purity and ploidy estimates reveals loss of HLA-DRB1:01:01:01, with one copy of HLA-DRB1:10:01:01:01 remaining.

REFERENCES

Alexandrov, L. B., Nik-Zainal, S., Wedge, D. C., Aparicio, S. A., Behjati, S., Biankin, A. V., Bignell, G. R., Bolli, N., Borg, A., Borresen-Dale, A. L., et al. (2013). Signatures of mutational processes in human cancer. Nature 500, 415-421.

Andreatta, M., and Nielsen, M. (2016). Gapped sequence alignment using artificial neural networks: application to the MHC class I system. Bioinformatics 32, 511-517.

Brown, S. D., Warren, R. L., Gibb, E. A., Martin, S. D., Spinelli, J. J., Nelson, B. H., and Holt, R. A. (2014). Neo-antigens predicted by tumour genome meta-analysis correlate with increased patient survival. Genome research 24, 743-750.

Campbell, J. D., Alexandrov, A., Kim, J., Wala, J., Berger, A. H., Pedamallu, C. S., Shukla, S. A., Guo, G., Brooks, A. N., Murray, B. A., et al. (2016). Distinct patterns of somatic genome alterations in lung adenocarcinomas and squamous cell carcinomas. Nature genetics 48, 607-616.

Campoli, M., and Ferrone, S. (2008). HLA antigen changes in malignant cells: epigenetic mechanisms and biologic significance. Oncogene 27, 5869-5885.

Carter, S. L., Cibulskis, K., Heiman, E., McKenna, A., Shen, H., Zack, T., Laird, P. W., Onofrio, R. C., Winckler, W., Weir, B. A., et al. (2012). Absolute quantification of somatic DNA alterations in human cancer. Nature biotechnology 30, 413-421.

Davoli, T., Uno, H., Wooten, E. C., and Elledge, S. J. (2017). Tumour aneuploidy correlates with markers of immune evasion and with reduced response to immunotherapy. Science (New York, N.Y. 355.

del Campo, A. B., Kyte, J. A., Carretero, J., Zinchencko, S., Mendez, R., Gonzalez-Aseguinolaza, G., Ruiz-Cabello, F., Aamdal, S., Gaudernack, G., Garrido, F., et al. (2014). Immune escape of cancer cells with beta2-microglobulin loss over the course of metastatic melanoma. Int J Cancer 134, 102-113.

Hanahan, D., and Weinberg, R. A. (2011). Hallmarks of cancer: the next generation. Cell 144, 646-674.

Hicklin, D. J., Marincola, F. M., and Ferrone, S. (1999). HLA class I antigen downregulation in human cancers: T-cell immunotherapy revives an old story. Mol Med Today 5, 178-186.

Hoof, I., Peters, B., Sidney, J., Pedersen, L. E., Sette, A., Lund, O., Buus, S., and Nielsen, M. (2009). NetMHCpan, a method for MHC class I binding prediction beyond humans. Immunogenetics 61, 1-13.

Jamal-Hanjani, M., Wilson, G. A., McGranahan, N., Birkbak, N. J., Watkins, T. B. K., Veeriah, S., Shafi, S., Johnson, D. H., Mitter, R., Rosenthal, R., et al. (2017). Tracking the Evolution of Non-Small-Cell Lung Cancer. The New England journal of medicine 376, 2109-2121.

Langmead, B., and Salzberg, S. L. (2012). Fast gapped-read alignment with Bowtie 2. Nat Methods 9, 357-359.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Li, B., Severson, E., Pignon, J. C., Zhao, H., Li, T., Novak, J., Jiang, P., Shen, H., Aster, J. C., Rodig, S., et al. (2016). Comprehensive analyses of tumour immunity: implications for cancer immunotherapy. Genome biology 17, 174.

Li, H., and Durbin, R. (2009). Fast and accurate short read alignment with Burrows-Wheeler transform. Bioinformatics 25, 1754-1760.

Martin, M. P., and Carrington, M. (2013). Immunogenetics of HIV disease. Immunological reviews 254, 245-264.

McGranahan, N., Furness, A. J., Rosenthal, R., Ramskov, S., Lyngaa, R., Saini, S. K., Jamal-Hanjani, M., Wilson, G. A., Birkbak, N. J., Hiley, C. T., et al. (2016). Clonal neoantigens elicit T cell immunoreactivity and sensitivity to immune checkpoint blockade. Science (New York, N.Y. 351, 1463-1469.

Mehta, A. M., Jordanova, E. S., Kenter, G. G., Ferrone, S., and Fleuren, G. J. (2008). Association of antigen processing machinery and HLA class I defects with clinicopathological outcome in cervical carcinoma. Cancer Immunol Immunother 57, 197-206.

Moretta, L., Montaldo, E., Vacca, P., Del Zotto, G., Moretta, F., Merli, P., Locatelli, F., and Mingari, M. C. (2014). Human natural killer cells: origin, receptors, function, and clinical applications. Int Arch Allergy Immunol 164, 253-264.

Nielsen, M., Lundegaard, C., Worning, P., Lauemoller, S. L., Lamberth, K., Buus, S., Brunak, S., and Lund, O. (2003). Reliable prediction of T-cell epitopes using neural networks with novel sequence representations. Protein Sci 12, 1007-1017.

Ott, P. A., Hu, Z., Keskin, D. B., Shukla, S. A., Sun, J., Bozym, D. J., Zhang, W., Luoma, A., Giobbie-Hurder, A., Peter, L., et al. (2017). An immunogenic personal neoantigen vaccine for patients with melanoma. Nature.

Rimmer, A., Phan, H., Mathieson, I., Iqbal, Z., Twigg, S. R., Consortium, W. G. S., Wilkie, A. O., McVean, G., and Lunter, G. (2014). Integrating mapping-, assembly- and haplotype-based approaches for calling variants in clinical sequencing applications. Nature genetics 46, 912-918.

Rizvi, N. A., Hellmann, M. D., Snyder, A., Kvistborg, P., Makarov, V., Havel, J. J., Lee, W., Yuan, J., Wong, P., Ho, T. S., et al. (2015). Cancer immunology. Mutational landscape determines sensitivity to PD-1 blockade in non-small cell lung cancer. Science (New York, N.Y. 348, 124-128.

Rooney, M. S., Shukla, S. A., Wu, C. J., Getz, G., and Hacohen, N. (2015). Molecular and genetic properties of tumours associated with local immune cytolytic activity. Cell 160, 48-61.

Rosenthal, R., McGranahan, N., Herrero, J., Taylor, B. S., and Swanton, C. (2016). deconstructSigs: delineating mutational processes in single tumours distinguishes DNA repair deficiencies and patterns of carcinoma evolution. Genome biology 17, 31.

Sahin, U., Derhovanessian, E., Miller, M., Kloke, B. P., Simon, P., Lower, M., Bukur, V., Tadmor, A. D., Luxemburger, U., Schrors, B., et al. (2017). Personalized RNA mutanome vaccines mobilize polyspecific therapeutic immunity against cancer. Nature.

Schumacher, T. N., and Schreiber, R. D. (2015). Neoantigens in cancer immunotherapy. Science (New York, N.Y. 348, 69-74.

Shen, R., and Seshan, V. E. (2016). FACETS: allele-specific copy number and clonal heterogenity analysis tool for high-throughput DNA sequencing. Nucleic Acids Res 44, e131.

Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nature biotechnology 33, 1152-1158.

Snyder, A., Makarov, V., Merghoub, T., Yuan, J., Zaretsky, J. M., Desrichard, A., Walsh, L. A., Postow, M. A., Wong, P., Ho, T. S., et al. (2014). Genetic basis for clinical response to CTLA-4 blockade in melanoma. The New England journal of medicine 371, 2189-2199.

Spranger, S., Spaapen, R. M., Zha, Y., Williams, J., Meng, Y., Ha, T. T., and Gajewski, T. F. (2013). Up-regulation of PD-L1, IDO, and T(regs) in the melanoma tumour microenvironment is driven by CD8(+) T cells. Sci Transl Med 5, 200ra116.

Szolek, A., Schubert, B., Mohr, C., Sturm, M., Feldhahn, M., and Kohlbacher, O. (2014). OptiType: precision HLA typing from next-generation sequencing data. Bioinformatics 30, 3310-3316.

Tran, E., Robbins, P. F., Lu, Y. C., Prickett, T. D., Gartner, J. J., Jia, L., Pasetto, A., Zheng, Z., Ray, S., Groh, E. M., et al. (2016). T-Cell Transfer Therapy Targeting Mutant KRAS in Cancer. The New England journal of medicine 375, 2255-2262.

Van Allen, E. M., Miao, D., Schilling, B., Shukla, S. A., Blank, C., Zimmer, L., Sucker, A., Hillen, U., Foppen, M. H., Goldinger, S. M., et al. (2015). Genomic correlates of response to CTLA-4 blockade in metastatic melanoma. Science (New York, N.Y. 350, 207-211.

Van Loo, P., Nordgard, S. H., Lingjaerde, O. C., Russnes, H. G., Rye, I. H., Sun, W., Weigman, V. J., Marynen, P., Zetterberg, A., Naume, B., et al. (2010). Allele-specific copy number analysis of tumours. Proceedings of the National Academy of Sciences of the United States of America 107, 16910-16915.

Yoshihama, S., Roszik, J., Downs, I., Meissner, T. B., Vijayan, S., Chapuy, B., Sidiq, T., Shipp, M. A., Lizee, G. A., and Kobayashi, K. S. (2016). NLRC5/MHC class I transactivator is a target for immune evasion in cancer. Proceedings of the National Academy of Sciences of the United States of America 113, 5999-6004.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of treating cancer in a subject, comprising administering to said subject a therapy targeting a neoantigen that is predicted to be presented by an HLA molecule encoded by an HLA allele which has been determined not to have been lost in a tumour in said subject, wherein determination of whether said HLA allele has been lost comprises the steps of:

aligning HLA allele sequence information from a tumour sample from said subject with an HLA allele reference sequence which is based on said subject's HLA type; and determining the specific copy number of said HLA allele in said tumour.

2. The method according to claim 1 wherein determination of whether said HLA allele has been lost is carried out by a sequence-based method.

3. The method according to claim 2 wherein the sequence-based method is carried out on HLA sequence information from the tumour sample from the subject.

4. The method according to any one of claim 1 wherein said neoantigen is a clonal neoantigen.

5. The method according to claim 1, wherein administering said therapy to said subject comprises administering to said subject:
   (i) a neoantigen that is predicted to be presented by an HLA molecule encoded by an HLA allele which has been determined not to have been lost in said tumour;
   (ii) an immune cell which recognises a neoantigen that is predicted to be presented by an HLA molecule encoded by an HLA allele which has been determined not to have been lost in said tumour; or
   (iii) an antibody which recognises a neoantigen that is predicted to be presented by an HLA molecule encoded by an HLA allele which has been determined not to have been lost in said tumour.

6. The method according to claim 5 wherein the immune cell is a T cell, B cell or dendritic cell.

7. The method according to claim 5 wherein the antibody is a monoclonal antibody.

8. The method according to claim 1 wherein the cancer is selected from bladder cancer, gastric cancer, oesophageal cancer, breast cancer, colorectal cancer, cervical cancer, ovarian cancer, endometrial cancer, kidney cancer (renal cell), lung cancer (small cell, non-small cell and mesothelioma), brain cancer (gliomas, astrocytomas, glioblastomas), melanoma, lymphoma, small bowel cancers (duodenal and jejunal), leukemia, pancreatic cancer, hepatobiliary tumours, germ cell cancers, prostate cancer, head and neck cancers, thyroid cancer and sarcomas.

9. The method according to claim 8 wherein the cancer is lung cancer.

10. The method according to claim 1 wherein the subject is a human.

11. The method of claim 1, wherein whether said HLA allele is lost has been determined by a method that comprises determining the specific copy number of said HLA allele in said tumour by a method that comprises one or more of the following steps:
   (i) determining mismatch positions in homologous HLA alleles, and determining mismatch coverage for each HLA allele;
   (ii) determining the ratio and allele frequency of each HLA allele based on mismatches and coverage determined in step (i):
   (iii) determining the copy number of each HLA allele in the tumour sample based on the ratio and allele frequency determined in step (ii).

12. The method of treating cancer in a subject, according to claim 1, wherein said method comprises the following steps:
   (a) selecting a neo-antigen that is predicted to be presented by an HLA molecule encoded by an HLA allele which has been determined not to have been lost in a tumour in said subject by the following method:
      (i) aligning HLA allele sequence information from a tumour sample from the subject with an HLA allele reference sequence which is based on said subject's HLA type;
      (ii) determining mismatch positions in homologous HLA alleles, and determining mismatch coverage for each HLA allele;
      (iii) determining the ratio and allele frequency of each HLA allele based on mismatches and coverage determined in step (ii);
      (iv) determining the copy number of each HLA allele in the tumour sample based on the ratio and allele frequency determined in step (iii); and
   (b) administering to said subject:
      (i) a neoantigen that is predicted to be presented by an HLA molecule encoded by an HLA allele which has been determined in step (a) not to have been lost in a tumour;
      (ii) an immune cell which recognises a neoantigen that is predicted to be presented by an HLA molecule encoded by an HLA allele which has been determined in step (a) not to have been lost in a tumour; or
      (iii) an antibody which recognises a neoantigen that is predicted to be presented by an HLA molecule encoded by an HLA allele which has been determined in step (a) not to have been lost in a tumour.

\* \* \* \* \*